(12) United States Patent
Mei et al.

(10) Patent No.: US 11,879,098 B2
(45) Date of Patent: *Jan. 23, 2024

(54) HIGH TRANSPARENCY ELECTROCHROMIC POLYMERS

(71) Applicant: AMBILIGHT INC., Grand Cayman (KY)

(72) Inventors: Jianguo Mei, West Lafayette, IN (US); Vaidehi Pandit, West Lafayette, IN (US); Zhiyang Wang, West Lafayette, IN (US)

(73) Assignee: AMBILIGHT INC., Grand Cayman (KY)

( * ) Notice: Subject to any disclaimer, the term of this patent is extended or adjusted under 35 U.S.C. 154(b) by 27 days.

This patent is subject to a terminal disclaimer.

(21) Appl. No.: 17/668,300

(22) Filed: Feb. 9, 2022

(65) Prior Publication Data
US 2023/0303913 A1  Sep. 28, 2023

(51) Int. Cl.
*C09K 9/02* (2006.01)
*C08G 61/12* (2006.01)

(52) U.S. Cl.
CPC ............ *C09K 9/02* (2013.01); *C08G 61/126* (2013.01); *C08G 2261/124* (2013.01); *C08G 2261/1412* (2013.01); *C08G 2261/1424* (2013.01); *C08G 2261/18* (2013.01); *C08G 2261/228* (2013.01); *C08G 2261/312* (2013.01); *C08G 2261/3221* (2013.01); *C08G 2261/3223* (2013.01); *C08G 2261/3241* (2013.01); *C08G 2261/3247* (2013.01); *C08G 2261/54* (2013.01); *C09K 2211/145* (2013.01); *C09K 2211/1425* (2013.01); *C09K 2211/1458* (2013.01); *C09K 2211/1466* (2013.01)

(58) Field of Classification Search
CPC ....................................................... C09K 9/02
See application file for complete search history.

(56) References Cited

U.S. PATENT DOCUMENTS

| 10,955,717 B1 | 3/2021 | Chen et al. |
| 2007/0008603 A1 | 1/2007 | Sotzing et al. |
| 2007/0191576 A1 | 8/2007 | Sotzing |

(Continued)

FOREIGN PATENT DOCUMENTS

| CN | 103483391 A | 1/2014 | |
| CN | 112126043 A * | 12/2020 | ........... C08G 61/126 |

(Continued)

OTHER PUBLICATIONS

Zheng, et al. "A novel self-healing electrochromic film based on a triphenylamine cross-linked polymer." Polymer Chemistry 8.45 (2017): 6981-6988.*

(Continued)

*Primary Examiner* — Shane Fang

(57) ABSTRACT

An electrochromic polymer is comprised of a repeat unit comprising one or more meta-conjugated linkers (MCLs) and one or more aromatic moieties (Ars). Each of the one or more MCLs is partially conjugated with the one or more Ars at meta positions of the MCLs to form a polymer backbone of the electrochromic polymer. The electrochromic polymer undergoes an optical switching and a color change in an electrochromic device, which shows a high transparency and a high optical contrast.

13 Claims, 9 Drawing Sheets

(56) References Cited

U.S. PATENT DOCUMENTS

| | | | |
|---|---|---|---|
| 2008/0100213 A1 | 5/2008 | Iwakuma et al. | |
| 2011/0288253 A1 | 11/2011 | Reynolds et al. | |
| 2012/0108778 A1* | 5/2012 | Amb .................. | C09K 9/02 |
| | | | 427/458 |
| 2019/0016852 A1 | 1/2019 | Mei et al. | |
| 2020/0387040 A1 | 12/2020 | He et al. | |
| 2022/0017689 A1 | 1/2022 | You et al. | |

FOREIGN PATENT DOCUMENTS

| | | |
|---|---|---|
| CN | 112126043 A | 12/2020 |
| WO | 2021/242267 A1 | 12/2021 |

OTHER PUBLICATIONS

Li, et al. "Structural effects of dibromocarbazoles on direct arylation polycondensation with 3, 4-ethylenedioxythiophene." Polymer Chemistry 7.18 (2016): 3165-3171.*

Yu, et al. "Preparation and characterization of a class of self-doping aromatic polyoxadiazole electrochromic materials." Journal of Applied Polymer Science 137.45 (2020): 49406.*

Machine translation of CN-112126043-A.*

Aubert, et al. "Copolymers of 3, 4-ethylenedioxythiophene and of pyridine alternated with fluorene or phenylene units: Synthesis, optical properties, and devices." Macromolecules 37.11 (2004): 4087-4098.*

Stalder, et al. "n-Type conjugated polyisoindigos." Macromolecules 44.16 (2011): 6303-6310.*

Zhang, et al. "Colorless-to-colorful switching electrochromic polyimides with very high contrast ratio." Nature communications 10.1 (2019): 1-8.*

Gaupp et al., Multichromic Copolymers Based on 3,6-Bis(2-(3,4-ethylenedioxythiophene))-N-alkylcarbazole Derivatives, Macromolecules, vol. 36, No. 17, Jul. 22, 2003 [retrieved on Jun. 23, 2022] Retrieved from the Internet: <URL: https://pubs.acs.org/doi/pdf/10.1021/ma034493e>. pp. 6305-6315.

Written Opinion of the International Searching Authority and International Search Report for PCT Application No. PCT/US2022/016609 dated Aug. 1, 2022 (14 pages).

Written Opinion of the International Searching Authority and International Search Report for PCT Application No. PCT/US22/30049 dated Oct. 13, 2022 (13 pages).

Yu, et al. "Preparation and characterization of a class of self-doping aromatic polyoxadiazole electrochromic materials." Journals Applied Polymer Science 137.45 (2020): 49406.

Non-Final Office Action for U.S. Appl. No. 17/748,383 dated Sep. 29, 2022 (26 pages).

* cited by examiner

HIGH TRANSPARENCY ELECTROCHROMIC POLYMERS

The present disclosure is related to a new type of electrochromic polymers that comprise meta-conjugated linkers and aromatic moieties, which present a high transparency in the visible light region in the neutral state. The polymers become highly absorbing in the visible light and near-infrared region and thus colored when their films are being oxidized. A device incorporating such conjugated electrochromic polymer films with a high optical contrast and a high transmittance is also disclosed.

BACKGROUND

Electrochromic devices allow to adjust light transmittance and control solar-heat gain. In comparison with inorganic-based electrochromic devices made through the vacuum sputtering process, polymer-based electrochromic windows can be manufactured through roll-to-roll coating and lamination. It thus renders a low-cost production and manufacturing flexibility. Polymer based electrochromic devices are typically composed of conjugated electrochromic polymers (ECPs), which feature fully conjugated polymer backbone made of $sp^2$ hybridized carbons. Conventionally, ECPs typically have strong absorbance in the visible light region and are thus colored in their neutral state. When they are oxidized, their absorption is shifted toward near-infrared (near-IR) region and they become transmissive in the visible light region. However, the oxidized polymers still have weak absorption in the visible light region, leading to residue colors. The problem becomes more severe when the polymer films are thick. As a result, it negatively impacts optical contrast of the polymers. Furthermore, it limits the highest optical transmittance an electrochromic conjugated polymer can achieve. In addition, conventional ECPs in the neutral state blocks visible light through the film and allow near-IR light passing through; While in the transmissive state, it allows visible light passing through and blocks near-IR light. This combination is not effective for thermal management and control the solar-heat gain (SHG). SHG describes the way radiation from the sun is turned into heat through a window product.

SUMMARY

The present disclosure is related to a new type of electrochromic polymer. The disclosed polymer backbone comprises a repeat unit comprising one or more meta-conjugated linkers (MCLs) and one or more aromatic moieties (Ars). Each of the one or more MCLs is partially conjugated with the one or more Ars at meta positions of the one or more MCLs to form the polymer backbone of an electrochromic polymer. In some embodiments, the electrochromic polymer is anodically-coloring electrochromic polymer (AC-ECP), becoming colored when it is oxidized.

In some embodiments, the electrochromic polymer has an absorption onset ($\lambda_c$, the wavelength at higher than which the polymer has no photon absorption) at 480 nm or less in the neutral state. In some embodiments, the electrochromic polymer has an absorption onset at 450 nm or less in the neutral state. In some embodiments, the electrochromic polymer has an absorption onset at 400 nm or less in the neutral state. In some embodiments, the absorption maxima ($\lambda_{max}$, the wavelength at which the polymer has its strongest photon absorption) are less than 420 nm in the neutral state. In some embodiments, the electrochromic polymer is colorless or yellow in the neutral state, while it is colored and visible and near-infrared absorbing in the oxidized state. The oxidized electrochromic polymer has an absorption coefficient larger than $10^4$ cm$^{-1}$ in the visible and/or near-IR region and thus colored in the oxidized state.

In spite of their high bandgaps, the disclosed ECPs still have relatively low oxidation potential in the ranges of 0.1-1.5 V inclusive versus Ag/AgCl electrode in some embodiments.

The MCL comprises at least one of an aromatic ring structure, or a fused aromatic ring structure, or the combinations thereof. The aromatic structure comprises a benzene or heterocyclic structure. The fused aromatic ring comprises a fused benzene structure or a fused heterocyclic structures or a fused benzene and heterocyclic ring structure.

In some embodiments, for the disclosed ECPs, the MCLs and the Ars are arranged in an alternative or random fashion with a general formula of

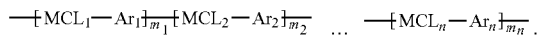

In the structures here, each of n and $m_1$, $m_2$, ..., $m_n$ is an integer higher than 0. The MCLs (or Ars) can be the same as or different from each other.

In some embodiments, the MCL and its meta-positions comprise

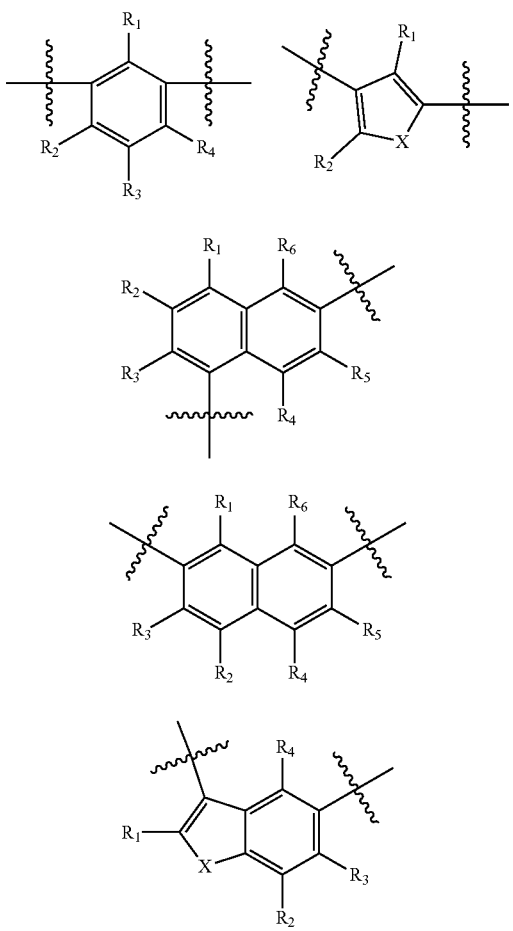

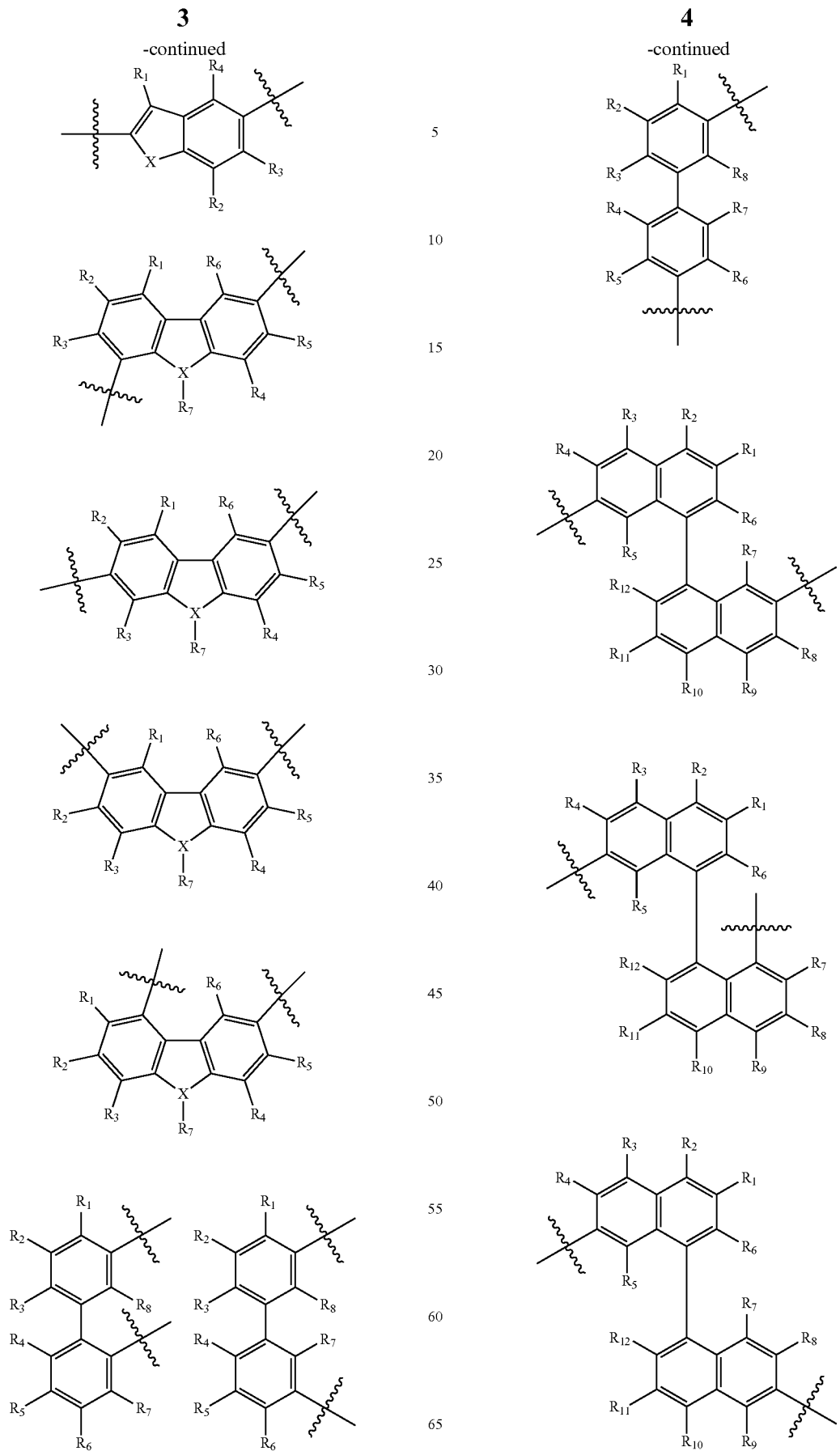

-continued
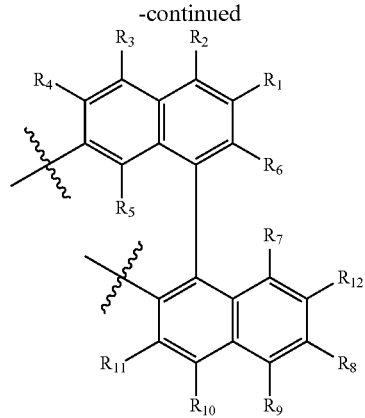
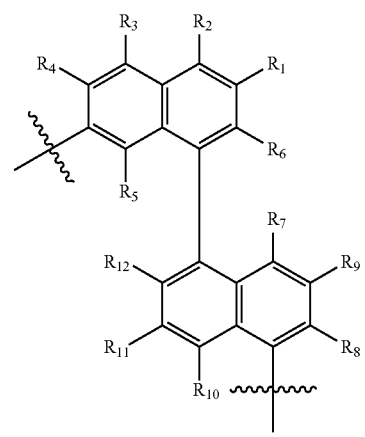
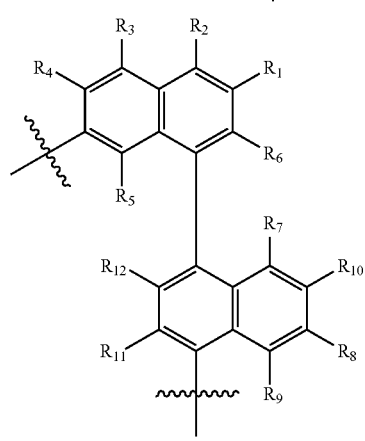
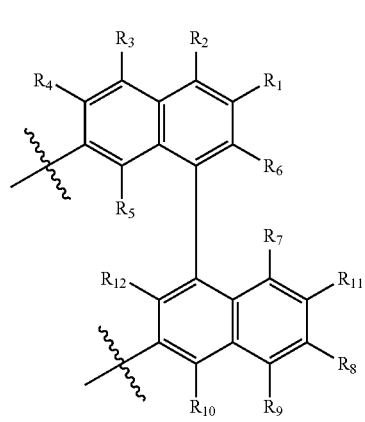
-continued
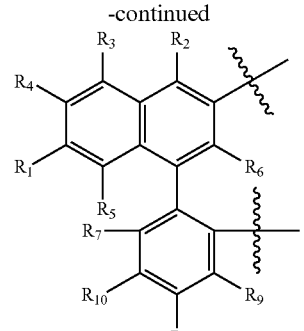
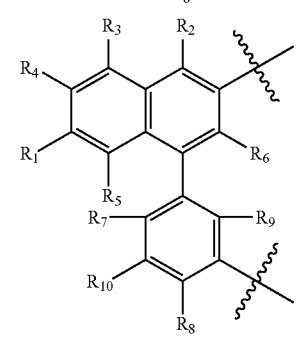
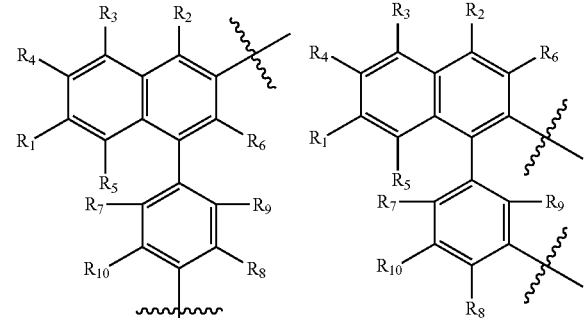
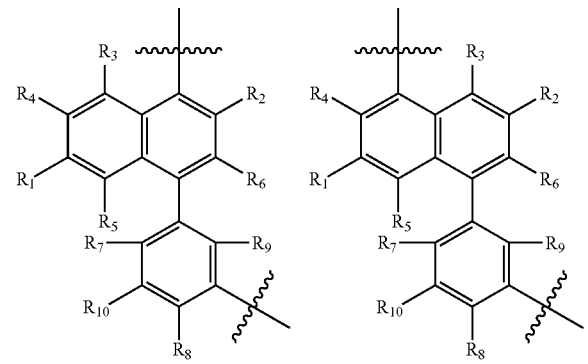
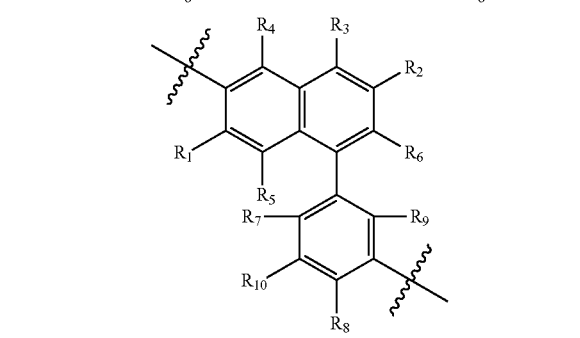

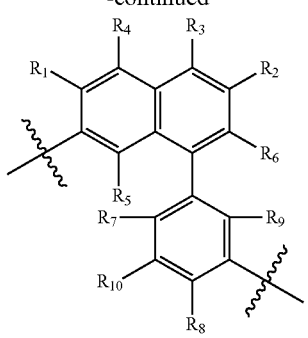
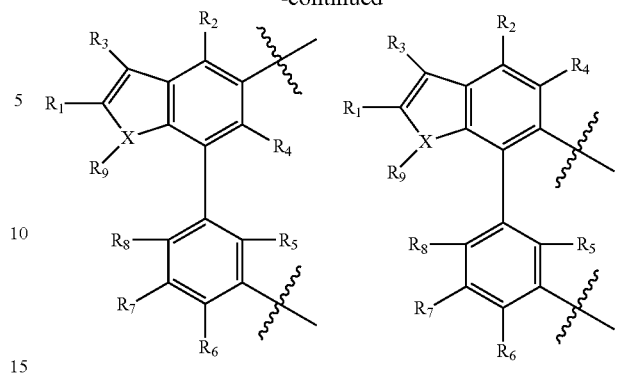
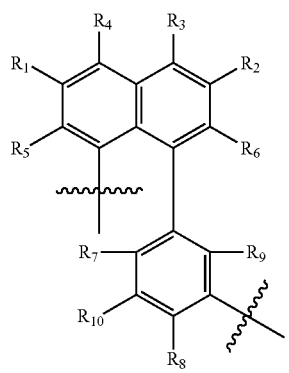
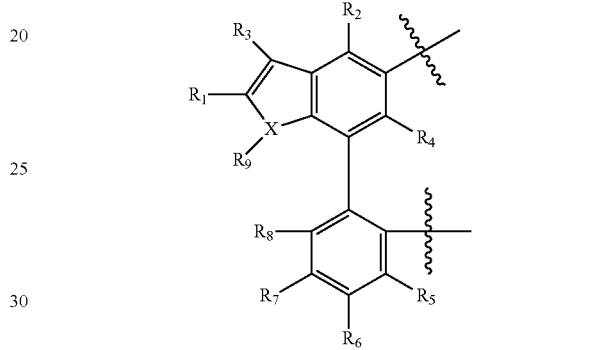
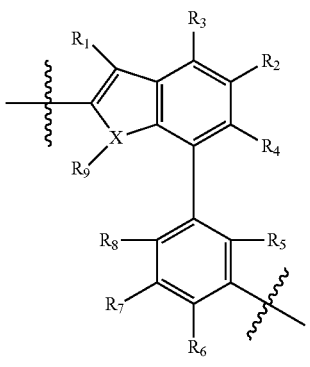
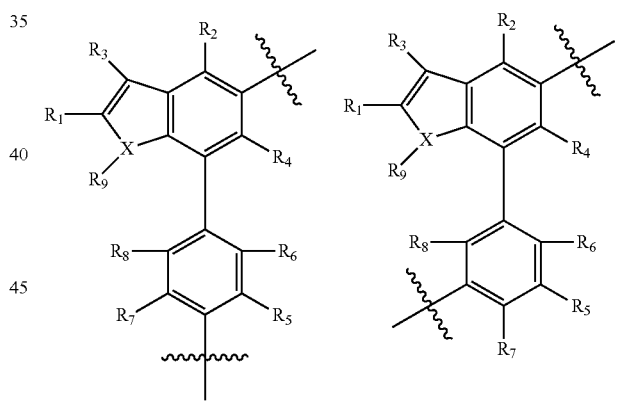
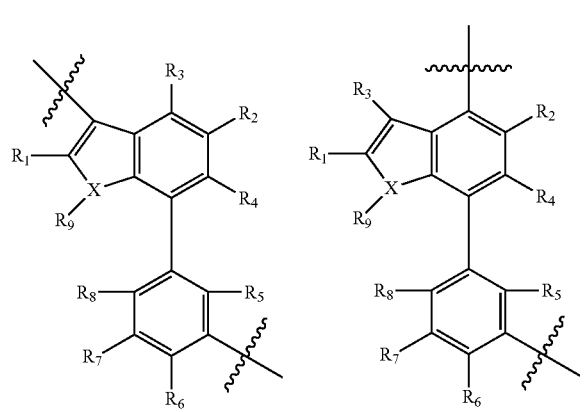
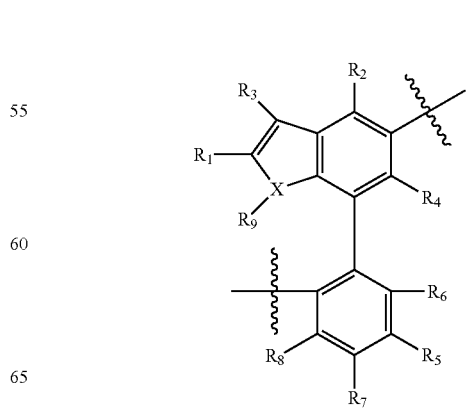

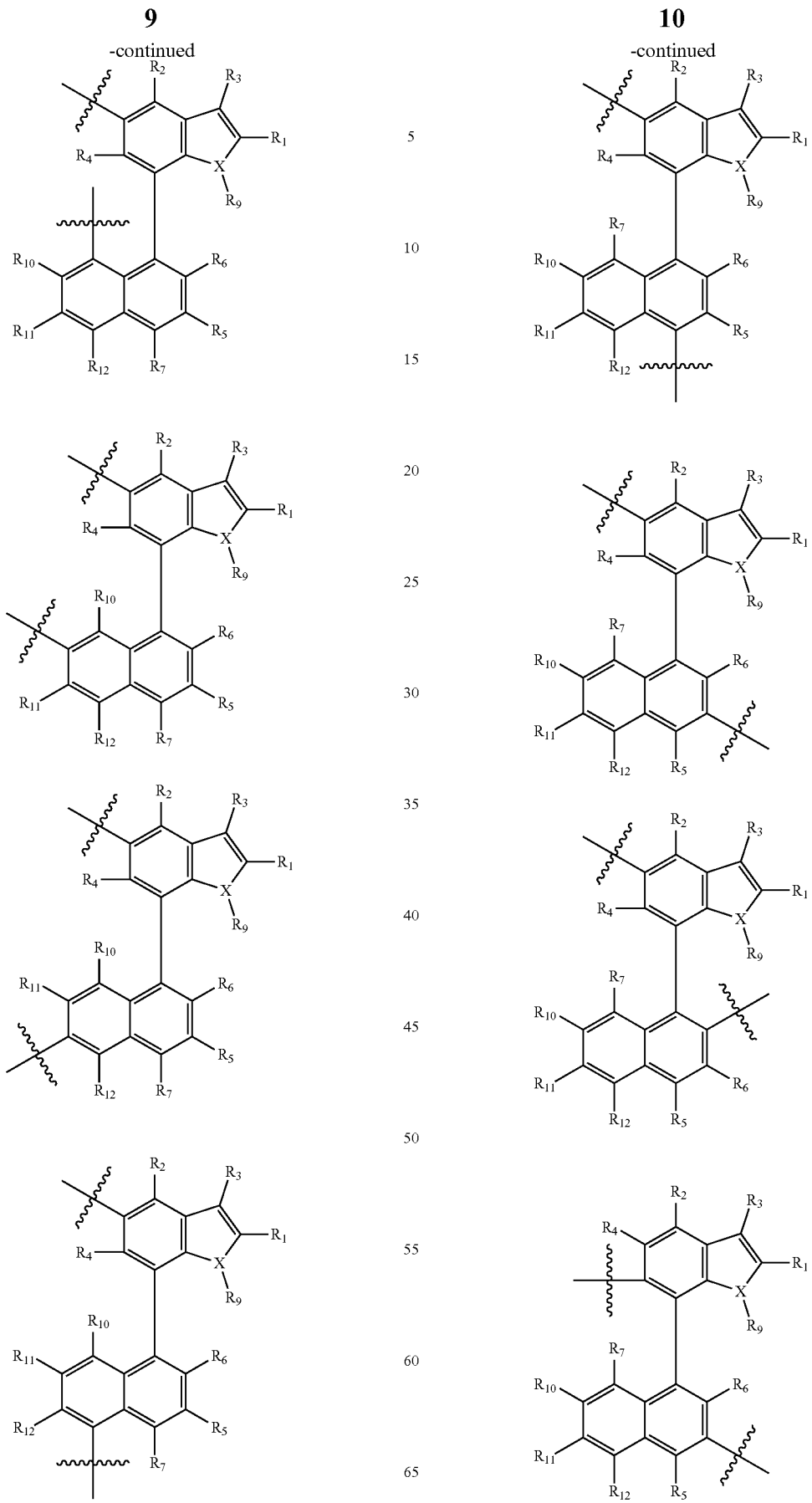

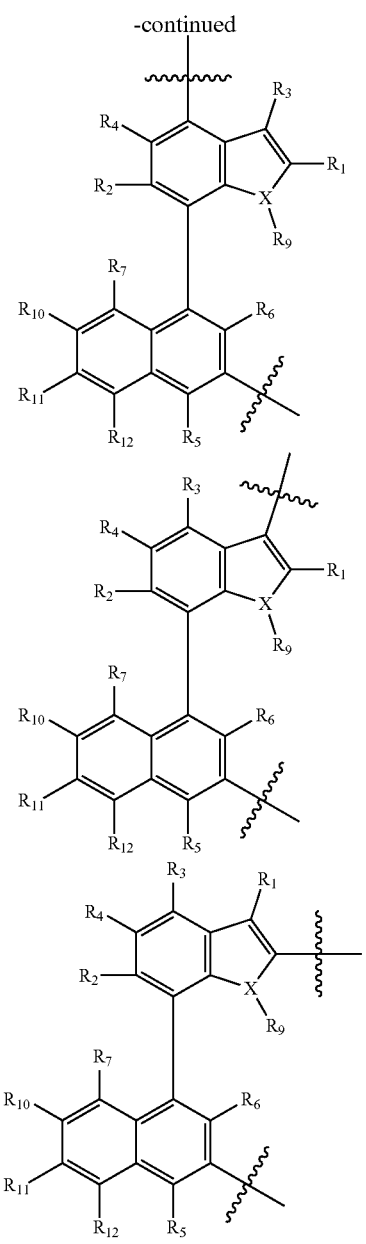

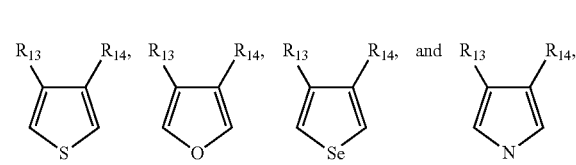

wherein each of the wavy lines represents meta-positions to link adjacent Ar units; X is S, Se, N, or O; $R_1$-$R_{12}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{15}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

In some embodiments, an Ar comprises one of a thiophene-based unit, a furan-based unit, a selenophene-based unit, or a pyrrole-based unit respectively with a formula of or any combination thereof, wherein each of $R_{13}$ and $R_{14}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{15}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

In some embodiments, the thiophene-based unit comprises a formula of

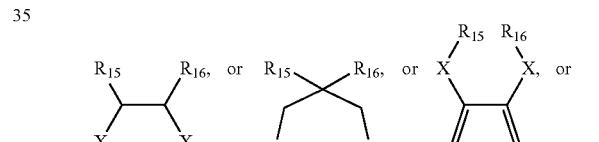

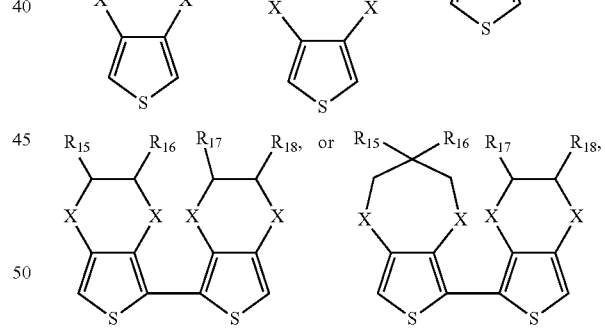

or

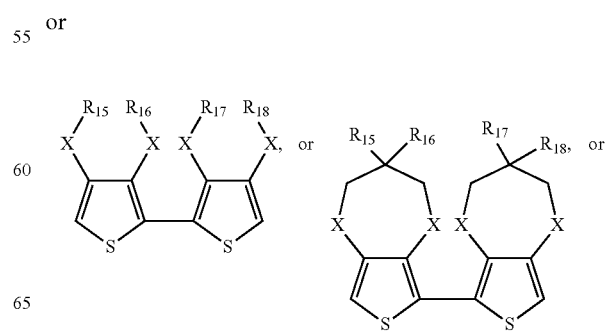

-continued

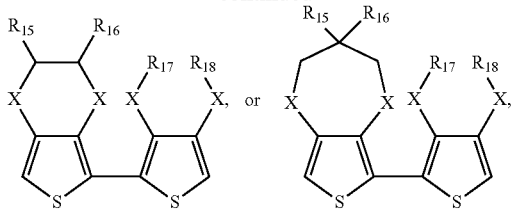

or a combination thereof,
wherein X is S, Se, N, or O; each of $R_{15}$-$R_{18}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{15}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

In some embodiments, X in the thiophene-based unit is O.

In some embodiments, the disclosed ECPs comprise a formula of

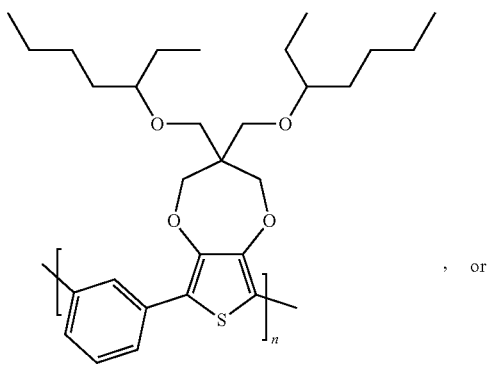

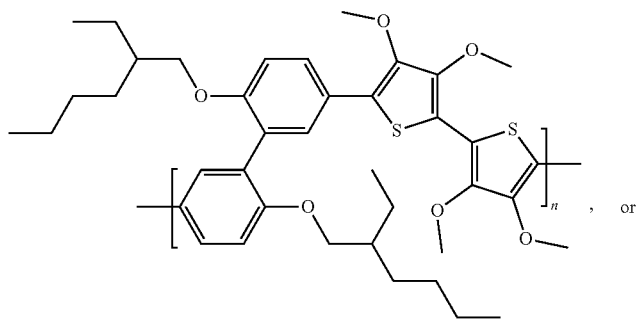

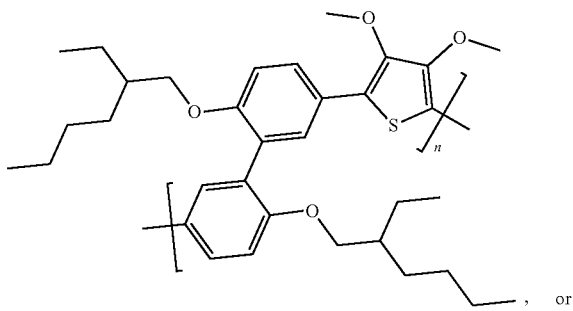

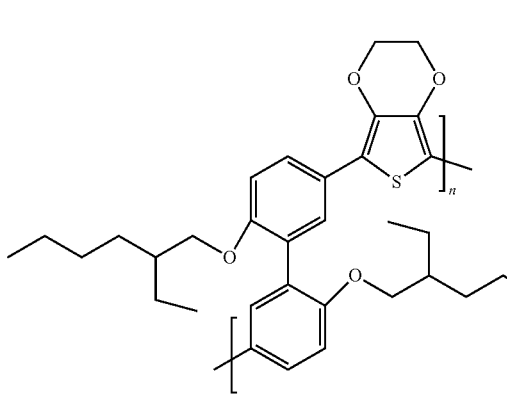

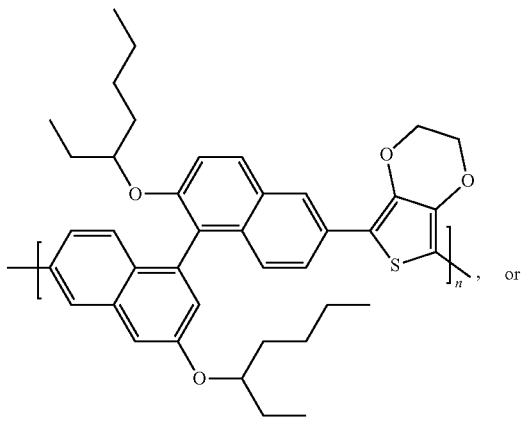

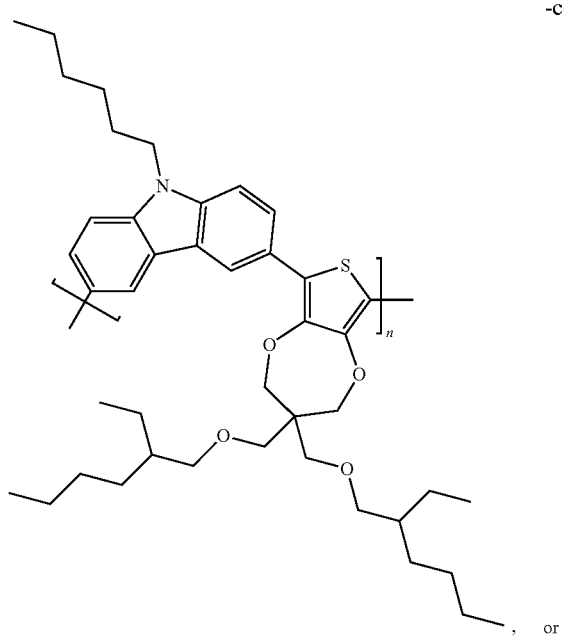
, or
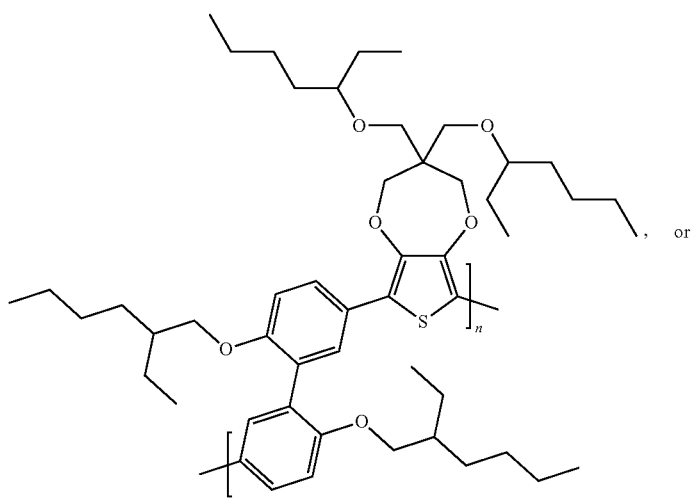
, or
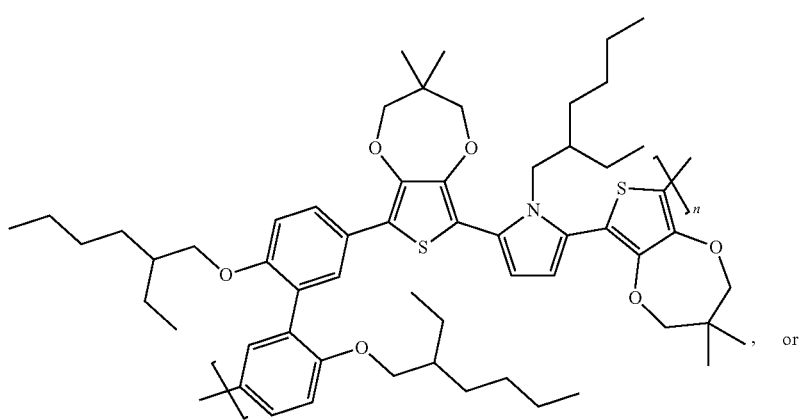
, or

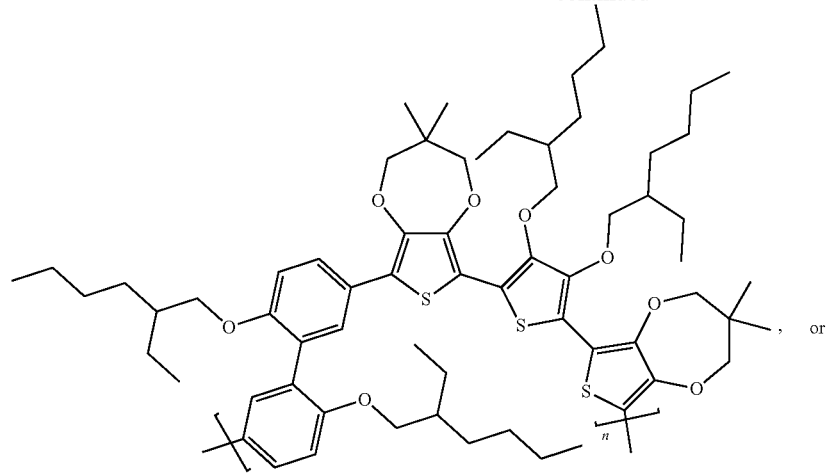
, or
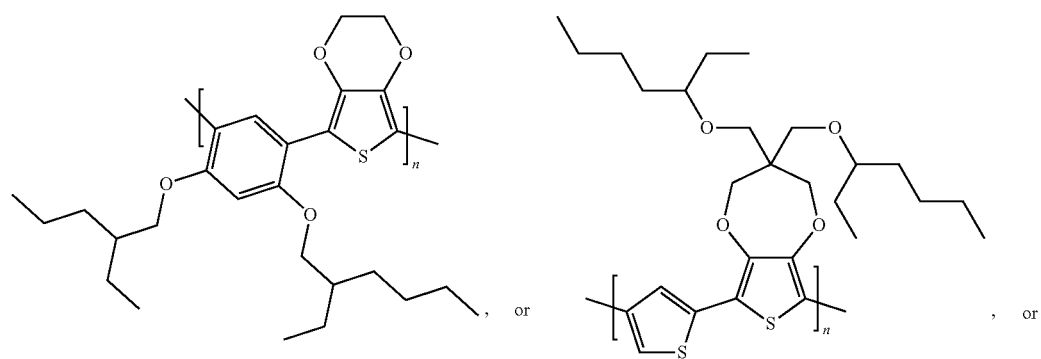
, or
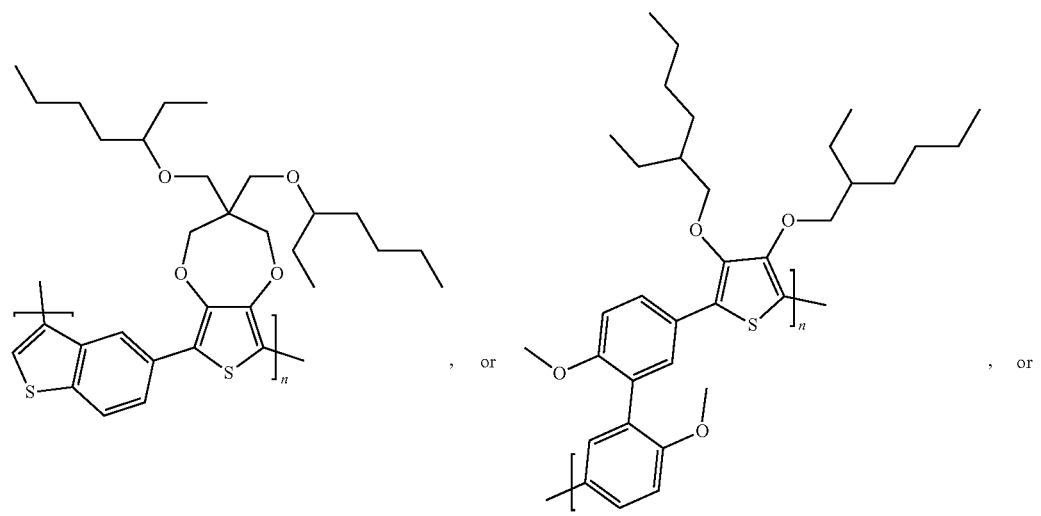
, or

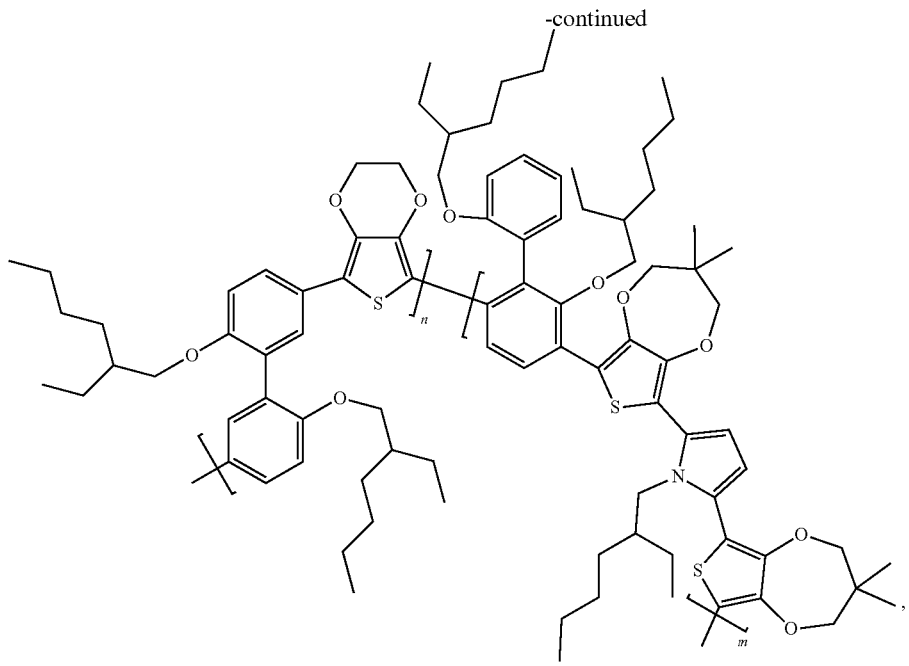

wherein n, and m are integers greater than 0.

In another aspect, an electrochromic polymer is provided. The electrochromic polymer includes a polymer backbone having one or more MCLs and one or more Ars. The electrochromic polymer has a transmittance of at least 60% in the visible light range (e.g., 450-750 nm) in a neutral state, and is colored and near-IR absorbing in an oxidized state.

In some embodiments, the electrochromic polymer is transparent in the visible light range in the neutral state.

In some embodiments, the one or more MCLs and the one or more Ars are coupled to each other alternatively or randomly such that a MCL is partially conjugated with an Ar at meta positions of the MCL.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings below. For the purpose of illustrating the invention, the drawings show aspects of one or more embodiments of the invention. However, it should be understood that the present invention is not limited to the precise arrangements and instrumentalities shown in the drawings.

DETAILED DESCRIPTION OF EMBODIMENTS

In the following description, certain specific details are set forth in order to provide a thorough understanding of various embodiments of the invention. However, one skilled in the art will understand that the invention may be practiced without these details. Moreover, while various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Unless the context requires otherwise, throughout the present specification and claims, the word "comprise" and variations thereof, such as "comprises" and "comprising" are to be construed in an open, inclusive sense, that is as "including, but not limited to." Recitation of numeric ranges of values throughout the specification is intended to serve as a shorthand notation of referring individually to each separate value falling within the range inclusive of the values defining the range, and each separate value is incorporated in the specification as it was individually recited herein. Additionally, the singular forms "a" "an", and "the" include plural referents unless the context clearly dictates otherwise.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment, but maybe in some instances. Furthermore, the particular features, structures, or characteristics may be combined in any suitable manner in one or more embodiments.

The present disclosure is related to a new type of electrochromic polymers. In some embodiments, the new type of electrochromic polymers may exhibits colorless-to-colored anodically coloring. The electrochromic polymers are called anodically coloring conjugated electrochromic polymers (AC-ECPs) with a repeat unit comprising one or more meta-conjugated linkers (MCLs) and one or more aromatic moieties (Ars), where meta-conjugation is introduced along the polymer backbone through the use of the MCL. Each of the one or more MCLs is partially conjugated with the one or more Ars at meta positions of the one or more MCLs to form the polymer backbone of the electrochromic polymer.

Figure 1A:
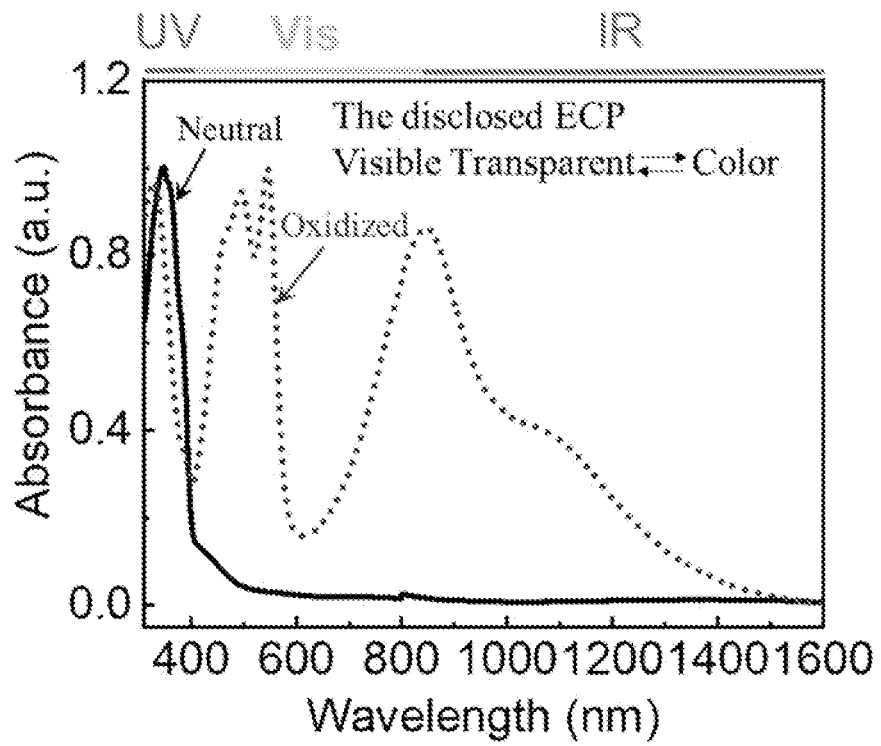
FIGS. 1(A)-(B) are diagrams representing the different color changing mechanisms of the disclosed ECP (FIG. 1(A)) compared to conventional ECP (FIG. 1(B)).
Figure 1B:
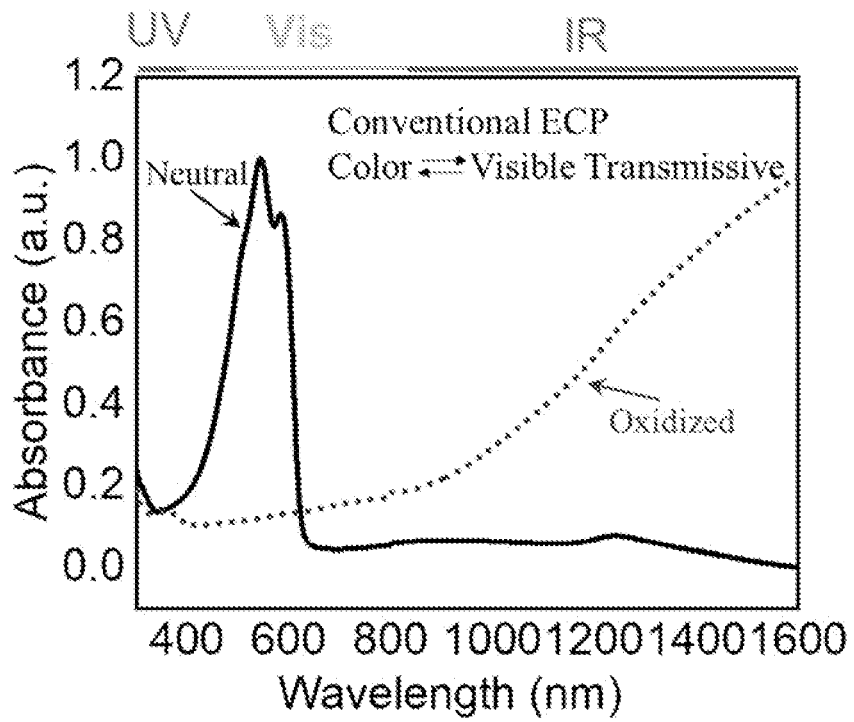

As illustrated in FIG. 1, conventional conjugated ECPs (FIG. 1(B)) are fully conjugated and have strong absorbance in the visible light region and are thus colored in their neutral state, while when oxidized (oxidized state), their absorption is shifted toward near-IR region and they become transmissive. However, the oxidized polymers still have weak absorption in the visible light region, leading to residue colors. On the other hand, as illustrated for one example disclosed ECP in FIG. 1(A), the ECP exhibits substantially no absorption after 400 nm in the neutral state and has several absorption peaks in visible light range and the near infrared range in the oxidized state, demonstrating coloring in the visible light range and near-infrared absorbing.

The disclosed ECPs allows passing or blocking of visible light and near-IR light to be synchronized, which is in one embodiment very useful in an electrochromic window for the management of solar heat gain. The disclosed ECPs are transparent in the neutral state, and are colored and IR-absorbing in the oxidized state, which are highly desired in order to achieve a high optical contrast, a high transmittance and a synergistic solar-heat gain.

The disclosed ECPs are transparent in the visible light region in the neutral state and are colored in the oxidized state. For example, the disclosed ECPs may have a transmittance of at least 60% in the visible light range (e.g., 450-750 nm) in the neutral state. In some embodiments, the disclosed ECPs may have a transmittance of at least 65%, 70%, 75%, 80%, 85%, 90%, 92%, 95%, 98%, or above in the range of 450-750 nm in the neutral state. In some embodiments, the disclosed ECPs are transparent in the visible light range in the neutral state. In the oxidized state, the disclosed ECPs have absorption in the visible light range (e.g., about 360 to 750 nm) and the near-IR range (e.g., about 750 to 1600 nanometers), thereby being colored and near-infrared absorbing.

The disclosed ECP has UV absorption. In some embodiments, the electrochromic polymer has an absorption onset ($\lambda_c$, the wavelength at higher than which the polymer has no photon absorption) at 480 nm or less in the neutral state. In some embodiments, the electrochromic polymer has an absorption onset at 450 nm or less or 400 nm or less in the neutral state. The absorption onset values of the neutral state spectra are defined as the x-intercept of the tangent line on the inflection point for the absorption peak of the neutral state spectra. In some embodiments, the absorption maxima ($\lambda_{max}$, the wavelength at which the polymer has its strongest photon absorption) are less than 420 nm in the neutral state. In some embodiments, the electrochromic polymer is colorless (e.g., no absorbance in 400-750 nm) or yellow (e.g., tailing absorption in 400-500 nm, or 400-480 nm, or 400-450 nm) in the neutral state and is colored and visible and near-IR absorbing in the oxidized state. The oxidized electrochromic polymer has an absorption coefficient larger than $10^4$ cm$^{-1}$ in the visible and/or near-IR region and thus colored in the oxidized state. In some embodiments, the disclosed AC-ECP has an energy bandgap equal to or higher than 2.5 eV and less than 4.0 eV in the neutral state. In some embodiments, the disclosed AC-ECP has an energy bandgap equal to or higher than 2.6, 2.7, 2.8, 2.9, or 3.0 eV and less than 4.0 eV in the neutral state.

Due to substantial lack of absorbance in the visible light range in the neutral state and high absorbance in the visible light range in the oxidized state, the disclosed ECPs demonstrate high optical contrast and high optical transmittance when comparing with conventional ECPs. In spite of their high bandgaps, the disclosed ECPs have relatively low oxidation potential in the ranges of 0.1-1.5 V inclusive versus Ag/AgCl electrode in some embodiments. The relatively low oxidation potential can benefit cycling durability of ECPs. Thus, the disclosed ECPs can be successfully incorporated into a device with a good cycling stability/reliability and a high optical contrast.

The MCL comprises at least one of an aromatic ring structure, or a fused aromatic ring structure, or the combinations thereof. The aromatic ring structure comprises a benzene or heterocyclic structure. The fused aromatic ring structure comprises a fused benzene structure or a fused heterocyclic structures or a fused benzene and heterocyclic ring structure. In some embodiments, the MCL comprises at least one of benzene, or naphthalene, or five-membered heterocycle, or benzene fused five-membered heterocycle, or a combination of these structures. Side chains or aromatic side chains can also be introduced onto the MCL to adjust its performance, for example, solubility or processability or stability.

In some embodiments, the MCLs and the Ars are arranged in an alternative or random fashion with a general formula of

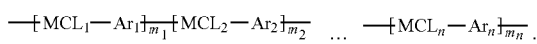

In the structure here, each of n and $m_1, m_2, \ldots, m_n$ is an integer higher than 0. Ar is an aromatic moiety, which may include one or more aromatic ring structures. Each of the MCLs (or Ars) can be the same as or different from each other.

Meta-conjugation is introduced in the polymer backbone through the use of the one or more MCLs. Each of the one or more MCLs is partially conjugated in the polymer backbone by connecting with Ar(s) through its meta-positions. For example, the meta-positions are two positions of the aromatic ring structure or a fused aromatic ring structure of the MCLs. When the meta-positions are connected, the pi electrons from an aromatic ring structure or a fused aromatic ring structure cannot be fully delocalized to another adjacently-connected unit through p-orbitals.

In some embodiments, an aromatic core comprises a benzene ring structure or a five-membered heterocyclic structure, and the aromatic core is substituted at meta-positions, which are the 1- and 3-positions on the aromatic ring. In some embodiments, the aromatic core structure comprises naphthalene, and the aromatic core is substituted at meta-positions, which are the 1- and 3-, or 1- and 4-, or 1- and 6-positions on naphthalene. In some embodiments, the aromatic core structure comprises benzene fused with a five-membered heterocycle, and the aromatic core is substituted at meta-positions, which are the 1- and 3-, or 1- and 5-positions on the benzene fused heterocycle.

Example structures of the MCL and its meta-positions may include:

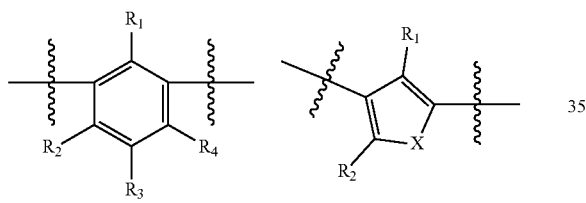

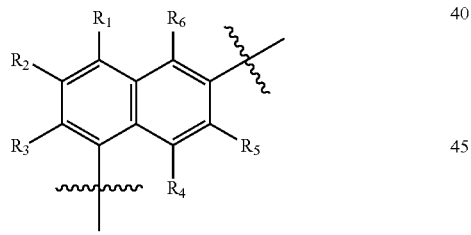

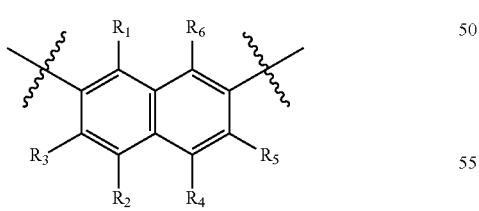

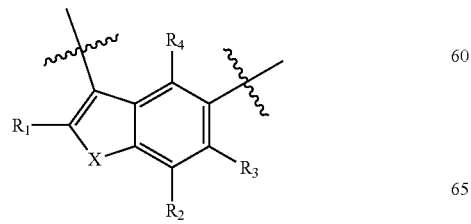

-continued

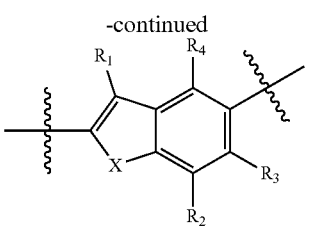

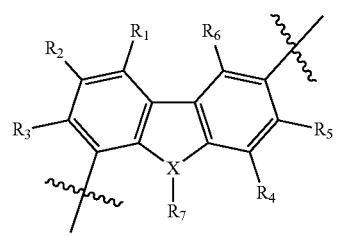

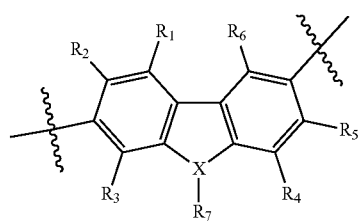

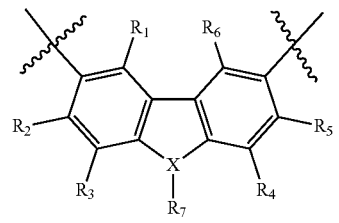

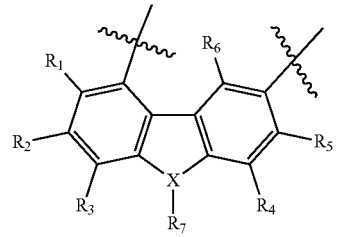

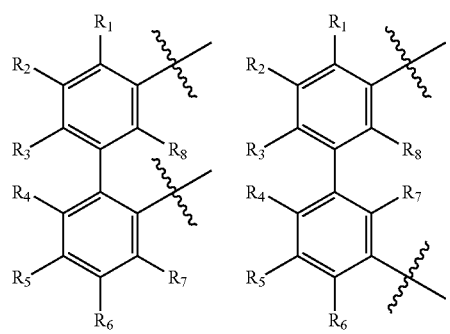

-continued
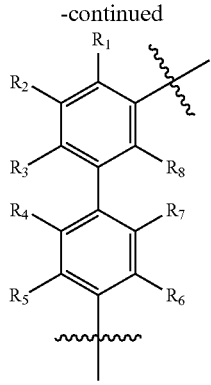
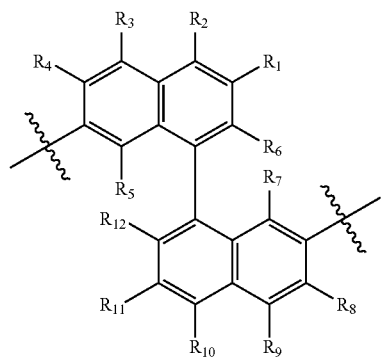
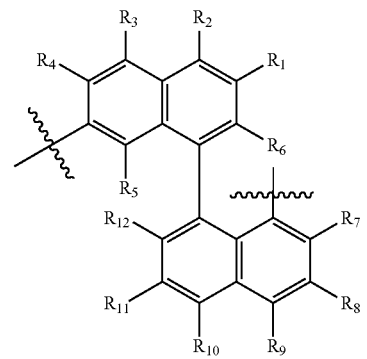
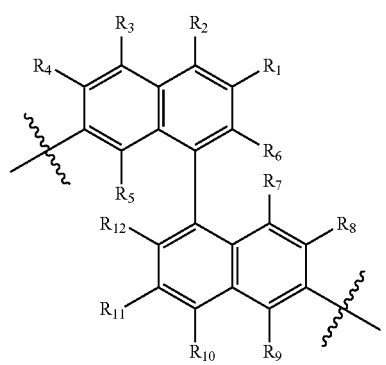
-continued
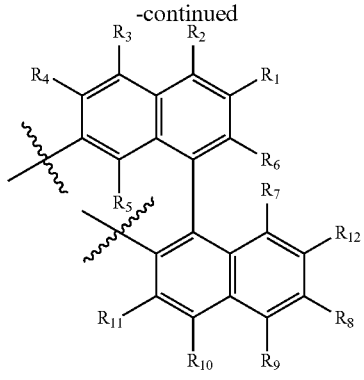
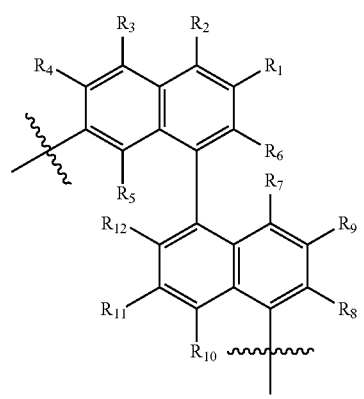
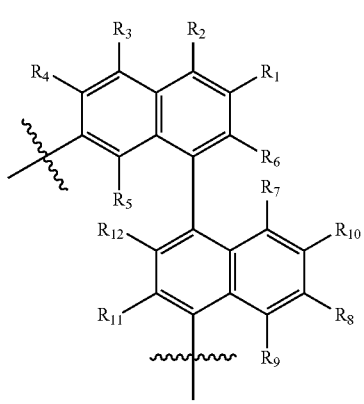
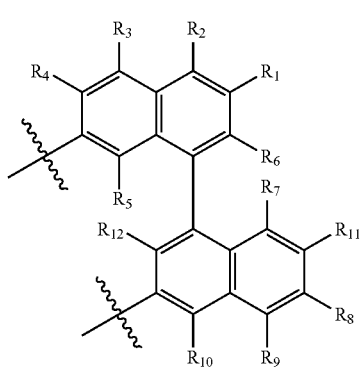

-continued
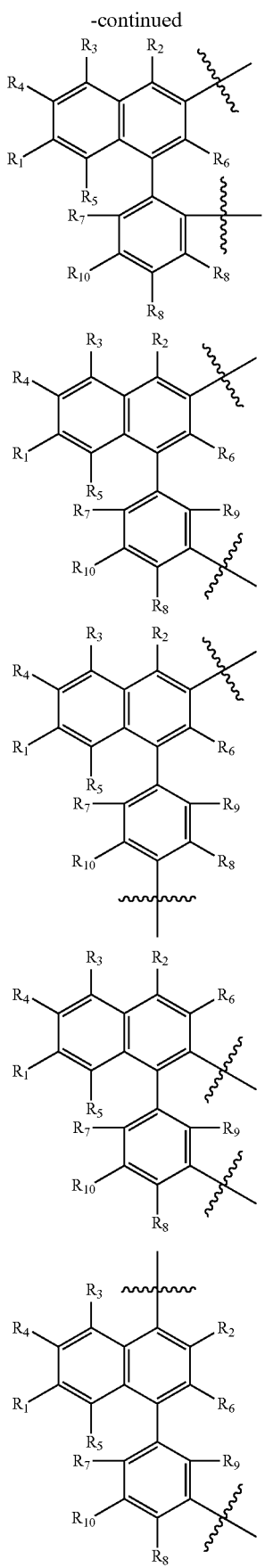
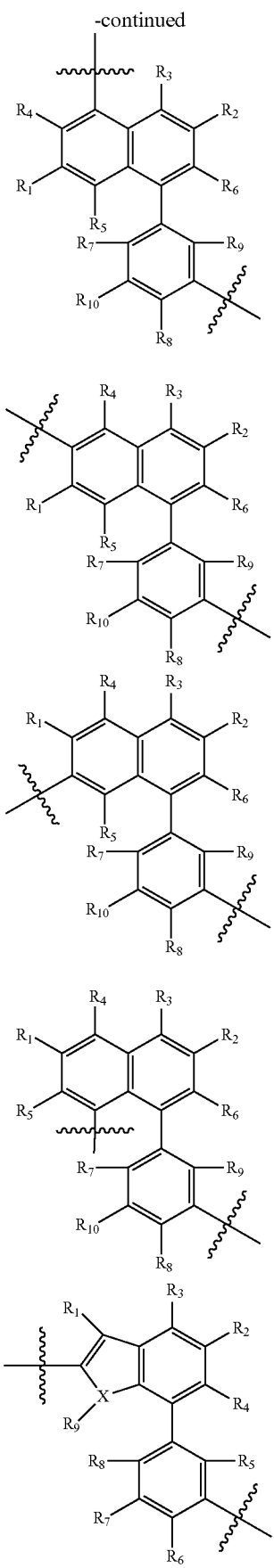

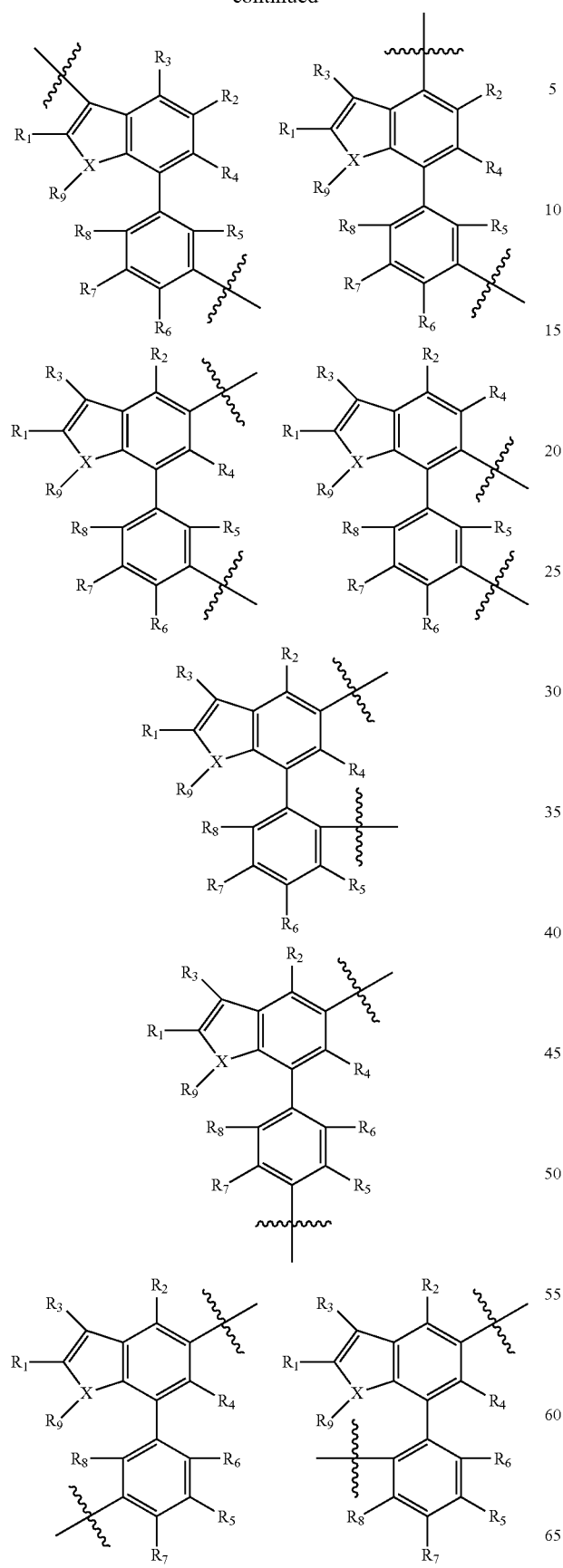
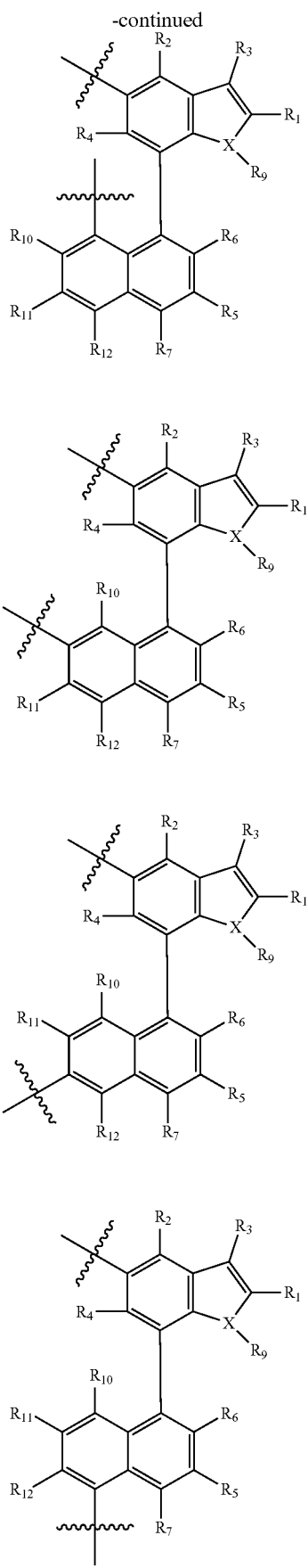

-continued

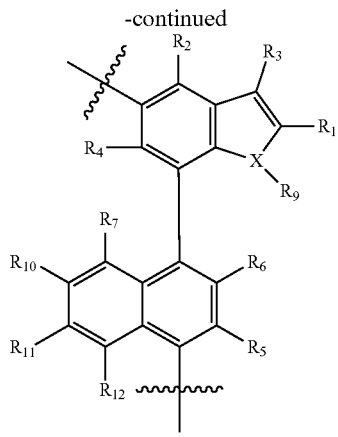

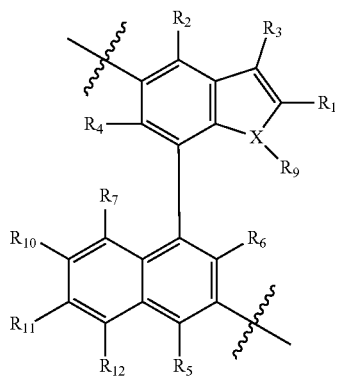

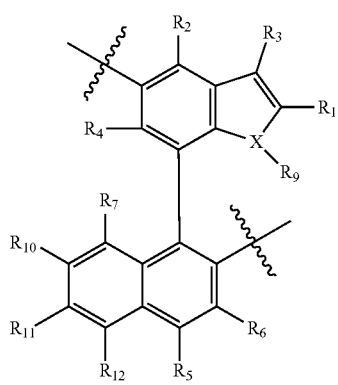

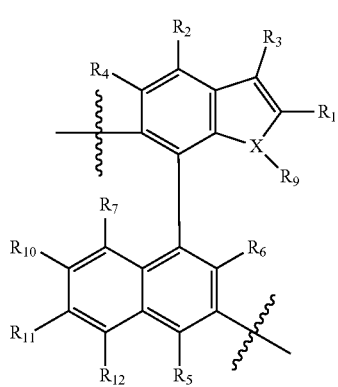

-continued

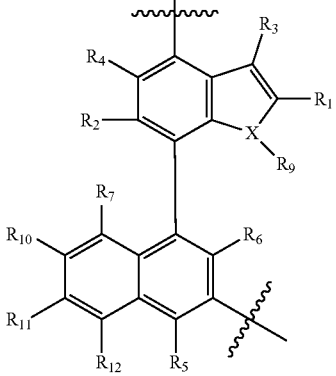

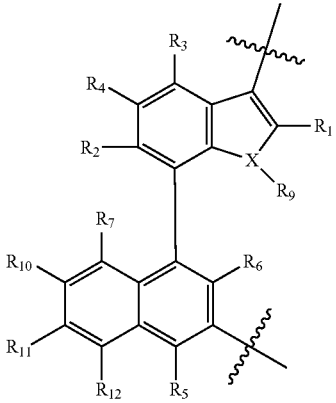

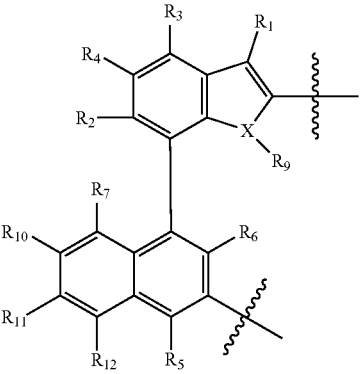

wherein X is S, Se, N, or O; $R_1$-$R_{12}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{15}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl; and the wavy lines represent the meta-positions.

The Ar may include, but is not limited to, any one of a thiophene-based unit, a furan-based unit, a selenophene-based unit, or a pyrrole-based unit respectively with a formula of

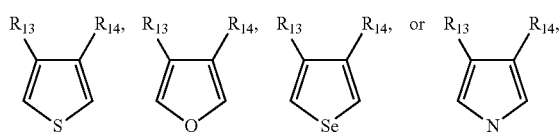

or any combination thereof.

In the structures above, each of $R_{13}$ and $R_{14}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{15}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

An example thiophene-based unit may include, but is not limited to, the formula of

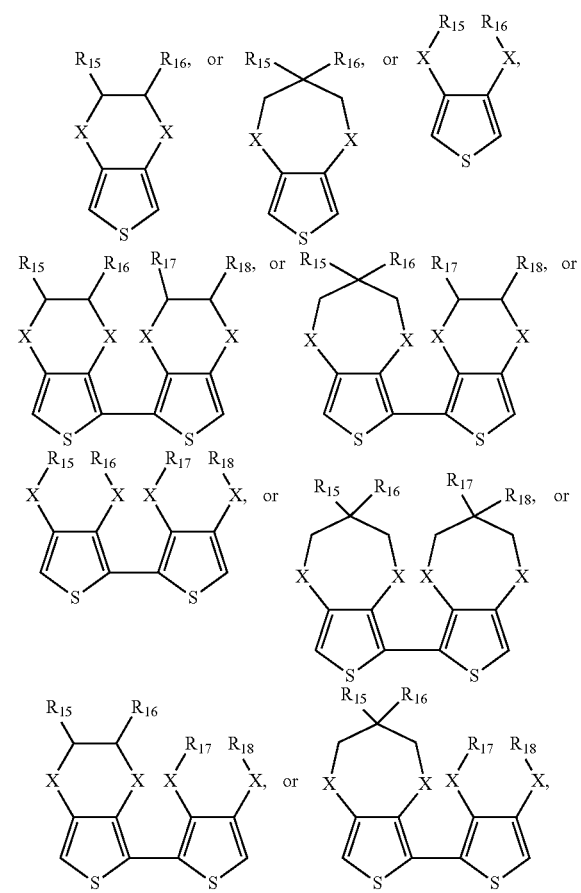

or any combination thereof.

In the structures above, X is S, Se, N, or O; each of $R_{15}$-$R_{18}$ is independently selected from the following substituents, including, but not limited to, hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

In some embodiments, the X in the thiophene-based unit is O.

By introducing meta-conjugation into the ECP polymer backbone, the electronic conjugation along the polymer backbone is interrupted and leads to a high bandgap (>2.0 eV). Thus, the disclosed ECP appears highly transmissive (or even transparent) in the neutral state. Oxidation of the ECP results in a lower bandgap (<1.5 eV), and the absorbance of the polymer is red-shifted from UV region to visible and near-IR region. Thus, the polymer becomes highly colored.

The Ar might include one or more aromatic ring structures or fused aromatic ring structures. By controlling the types and amounts of the Ar, the redox potentials of the disclosed ECP can be easily tuned while maintaining its high transparency within the visible light range in the neutral state. For example, more electron-rich units (e.g., dioxythiophenes) can be introduced onto the backbone to make the polymer more favorable to be oxidized, thereby decreasing its onset potential and improving its electrochemical stability and electrochromic cycling stability. The redox potentials of the disclosed ECP can also be adjusted by varying substituents on MCLs (e.g., introducing alkoxy side chains).

The disclosed ECPs can be dissolved in a solvent, for example, toluene or p-xylene, which can be used for solution-processable film casting processes. By controlling the concentration of the polymer solution, a polymer thin film with a controllable thickness can be obtained. Furthermore, the excellent solubility makes the disclosed ECPs compatible with various casting methods, for example, spin-coating, spray-coating, and drop-casting. Manufacturing friendly process makes its extended applications feasible.

Examples are shown in the following.

EMBODIMENTS

Example 1 ECP-1

In some embodiments, the disclosed ECP-1 comprises a formula of

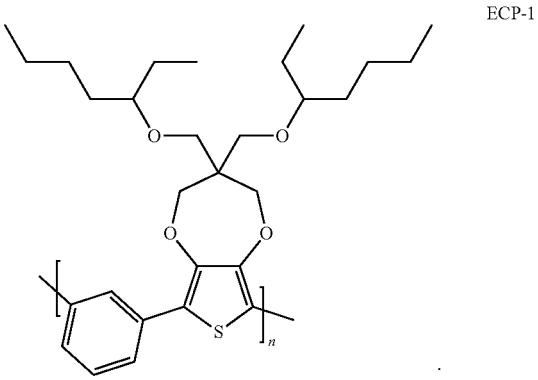

ECP-1 is synthesized by first preparing a benzene reaction unit and then polymerizing the benzene reaction unit with a ProDOT unit. The detail method includes the following steps:

Step 1-1: preparing a benzene reaction unit (compound 1)

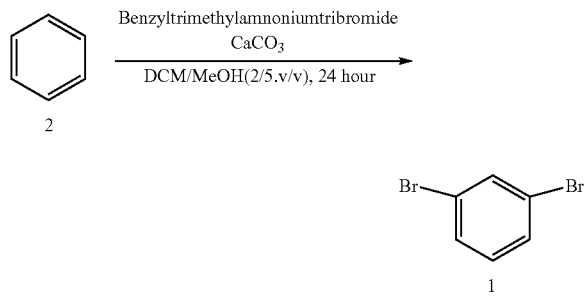

Compound 2, benzyltrimethylammonium tribromide, and $CaCO_3$ are dissolved in methanol/dichloromethane (2/5, v/v). The mixture is stirred at room temperature for 24 hours. The reaction mixture is concentrated under reduced pressure, and the residue is dissolved in chloroform. The solution is washed with deionized water, dried over sodium sulfate, and the solvent is removed in vacuum.

Step 1-2: Polymerization

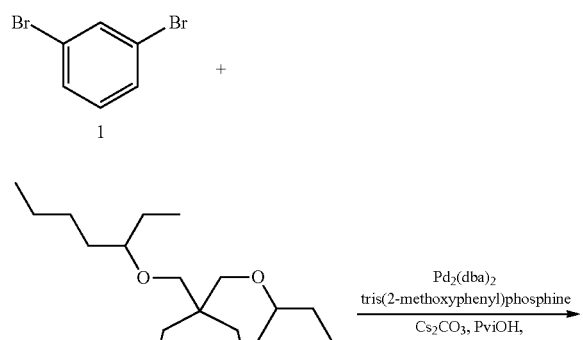

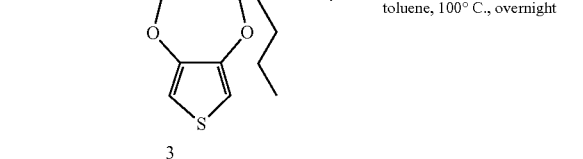

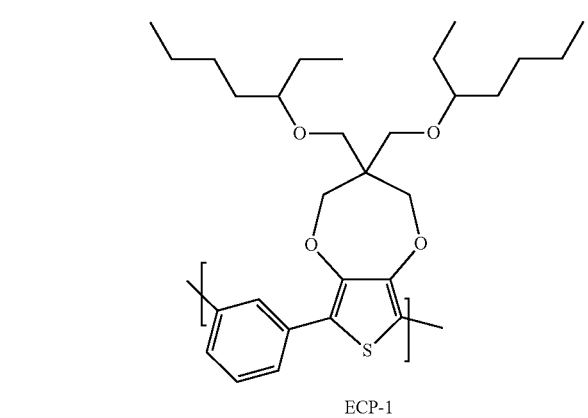

ECP-1

The benzene reaction unit (compound 1), ProDOT(compound 3), and Pd2(dba)2, tris(2-methoxyphenyl)phosphine, $Cs_2CO_3$, and PviOH are added in a dry Schlenk tube under $N_2$. The Schlenk tube is then put under high vacuum followed by backfilling with nitrogen twice. Toluene is added to the solvent, and the reaction mixture is subjected to three-pump-thaw cycle backfilling with nitrogen. The reaction mixture is heated at 100° C. for one day. Stop the reaction and add chloroform. Wash the reaction mixture with deionized water and extract the aqueous with chloroform. The combined organic phase is dried over anhydrous sodium sulfate, and then it is filtered and dried in vacuum. The solid is dissolved in chloroform, and the solution is poured into vigorously stirred methanol for precipitation. Filter to obtain the polymer.

Figure 2:
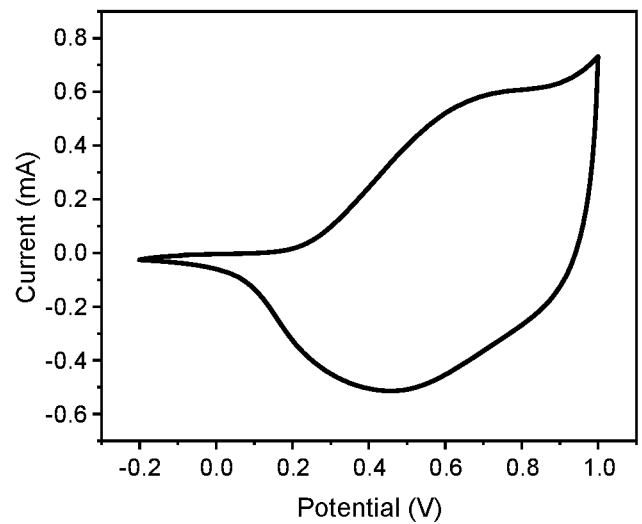
FIG. 2 is the CV data of an exemplary solid-state device using an example ECP-1, according to one embodiment.
Figure 3:
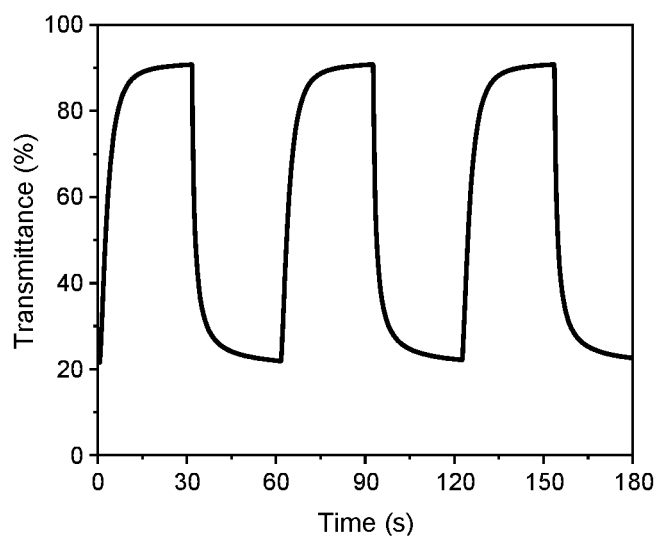
FIG. 3 is the switching kinetics of the exemplary solid-state device using the example ECP-1 at 483 nm, according to one embodiment.
Figure 4:
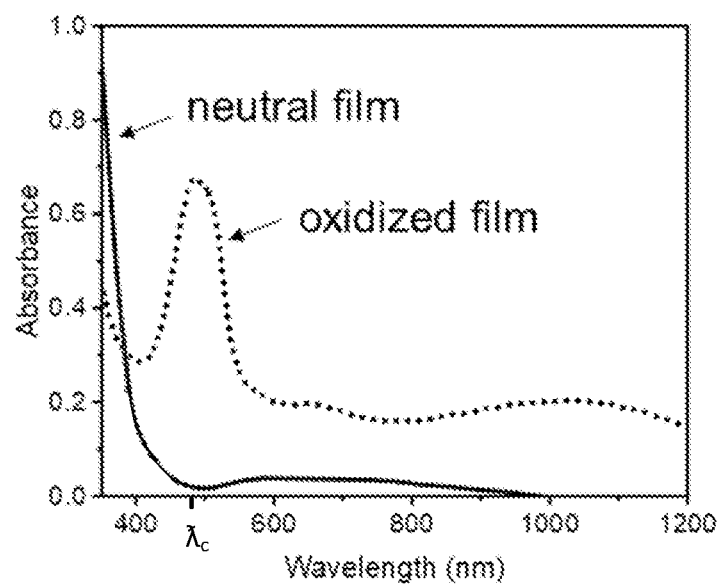
FIG. 4 are the absorbance spectra of the exemplary ECP-1 thin film at different voltages, according to one embodiment.
Figure 11:
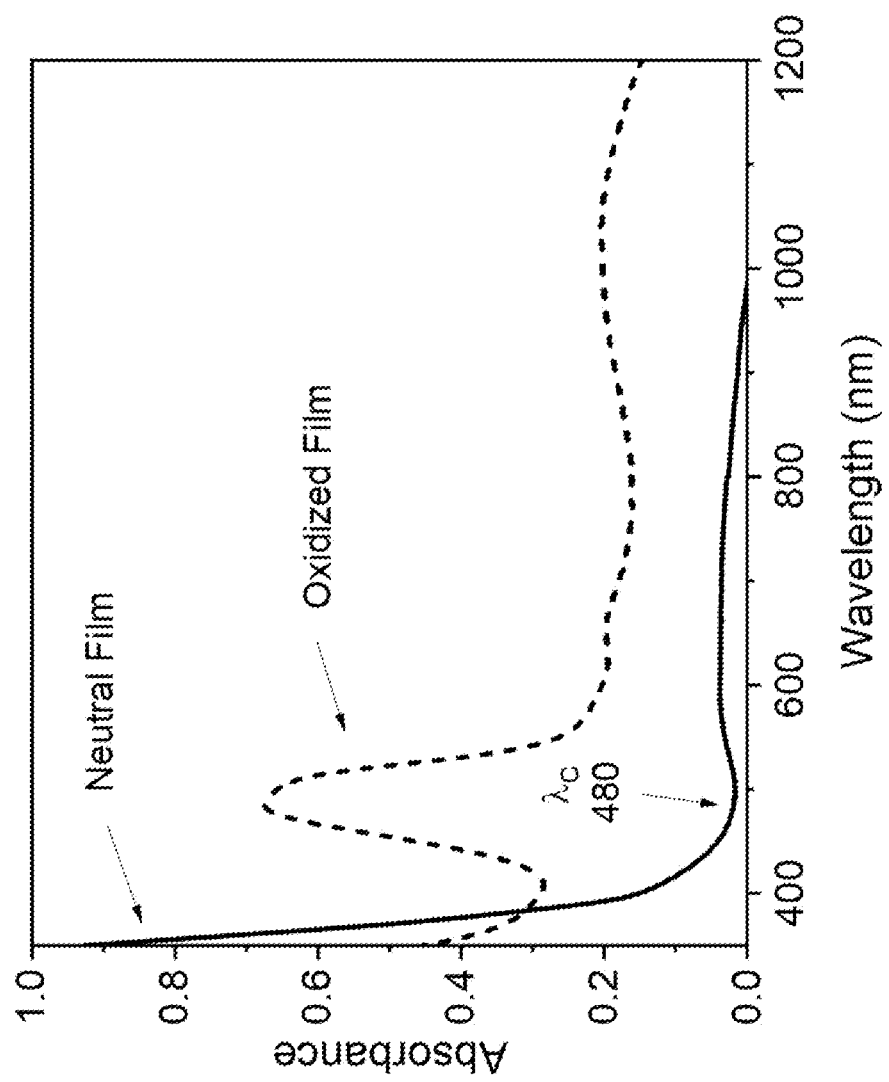
FIG. 11 shows the absorbance spectra of the exemplary ECP-1 thin film at different voltages, according to one embodiment.

The obtained ECP-1 has an oxidation potential of around 0.6 V (vs. Ag/AgCl) and an energy bandgap higher than 2.8 eV. It is fabricated into a solid-state electrochromic device (ECD) with ECP-1 used as the electrochromic layer, 1M of $LiPF_6$ in PEGMEA as the electrolyte, and $VO_x$ as the ion storage layer. The solid-state ECD can be stably switched between −0.2 V to 1.0 V (FIG. 2). The neutral state and oxidized state absorption spectra of the ECP-1 thin film are shown in FIG. 4 with $\lambda_c$ of 400 nm when the absorption onset is "defined as the x-intercept of the tangent line on the inflection point for the absorption peak of the neutral state spectra". Referring to FIG. 11, the absorption onset is 480 nm when the absorption onset is defined as "the wavelength at higher than which the polymer has no photon absorption." The solid-state ECD is highly transparent with a transmittance up to 90% in neutral state at around 550 nm (−0.2 V) (FIG. 3), and displays a bright red color when the ECP-1 is oxidized with one absorption peak at around 487 nm and elevated absorption spectra at IR range, around 900 to 1100 nm (FIG. 4). The optical contrast of the solid-state ECD is about 69% (as shown in FIG. 3).

Example 2 ECP-2

In some embodiments, the disclosed ECP-2 has a formula of

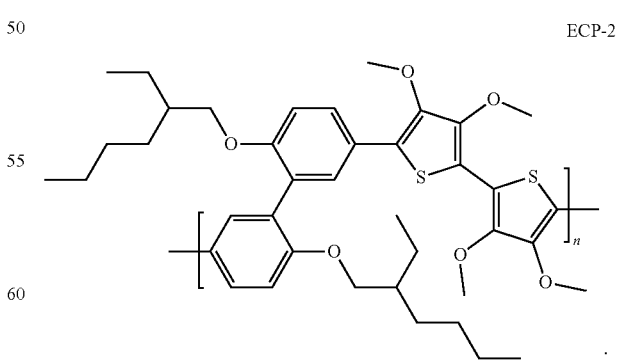

ECP-2

The ECP-2 is synthesized by preparing a benzene-containing reaction unit and then polymerizing it with a dimer unit. The detail method includes the following steps:

Step 2-1: preparing a benzene-containing reaction unit (compound 4) by two steps.

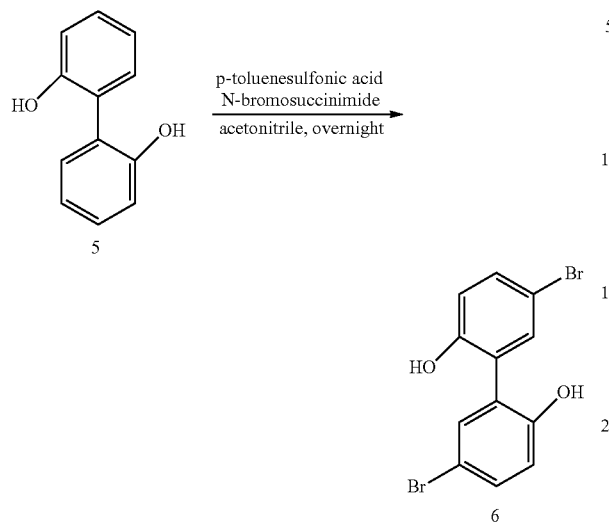

Compound 5 and p-toluenesulfonic acid are dissolved in acetonitrile. Subsequently, N-bromosuccinimide is added, and the mixture is agitated overnight. The suspension is filtered to get the desired product. The product compound 6 is a white solid.

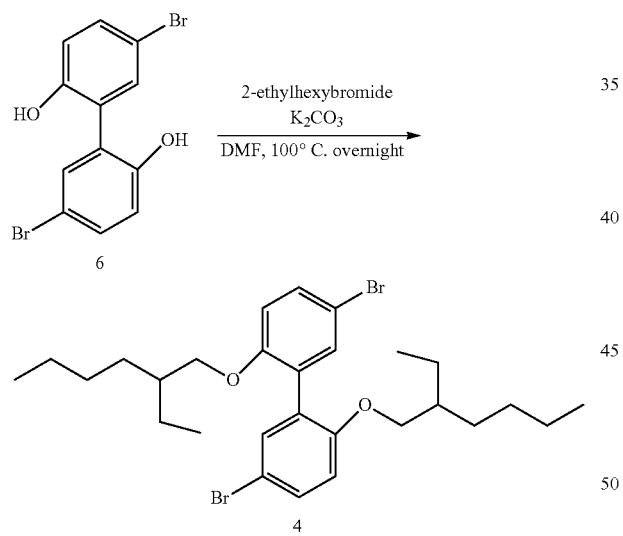

Compound 6 is dissolved in DMF under $N_2$. $K_2CO_3$ is added to the solution, and the reaction mixture is stirred for 15 mins, after which 2-ethylhexyl bromide is added. The reaction mixture is stirred at 100° C. overnight. The reaction is stopped and cooled down to room temperature. The solvent is removed in vacuum, and the residue is dissolved in diethyl ether. The organic phase is washed with water, and the aqueous phases are extracted with ethyl acetate. The combined organic phases are dried, and the volatiles is removed by vacuum. The crude is passed through a small silica column, and the solvent is dried in vacuum to get the compound 4 as a yellow oil.

Step 2-2: polymerization: The polymerization method is similar to that in step 1-1, only differs on the reaction units.

The reaction units here are the benzene-containing reaction unit (compound 4) and a dimer unit (compound 7) with a structure of

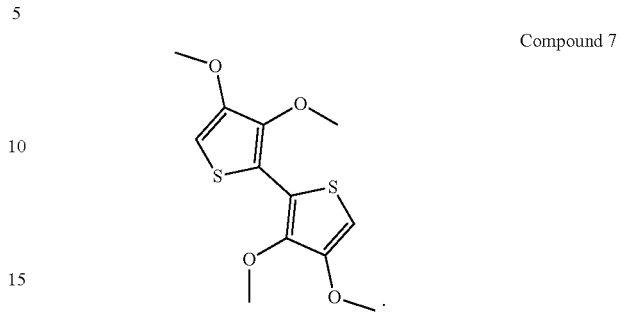

Figure 5:
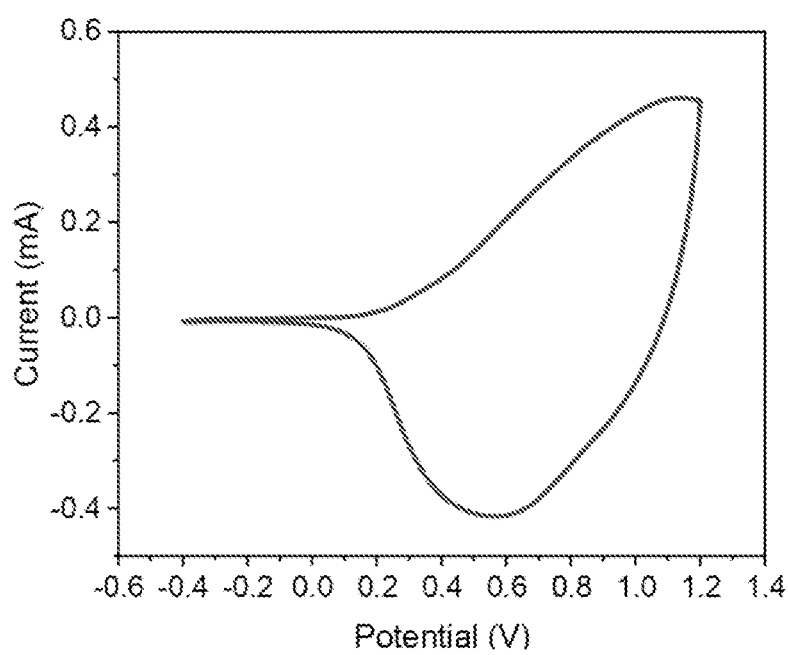
FIG. 5 is the CV data of an exemplary solid-state device using another example ECP-2, according to one embodiment.
Figure 6:
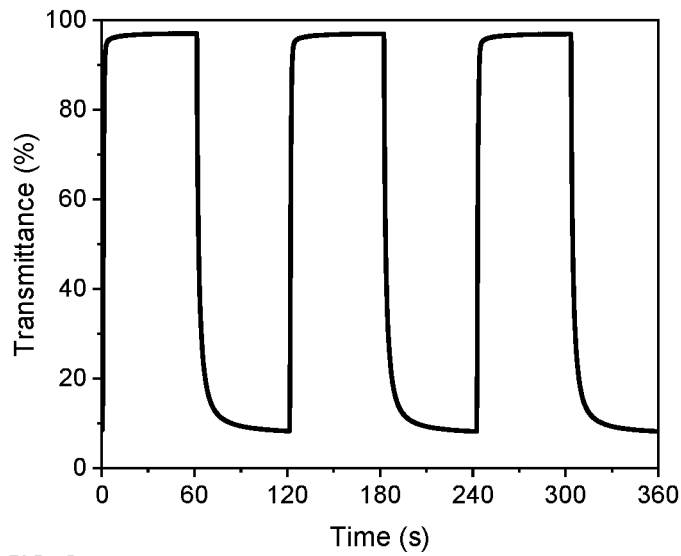
FIG. 6 is the switching kinetics of the exemplary solid-state device using the example ECP-2 at 550 nm, according to one embodiment.
Figure 7:
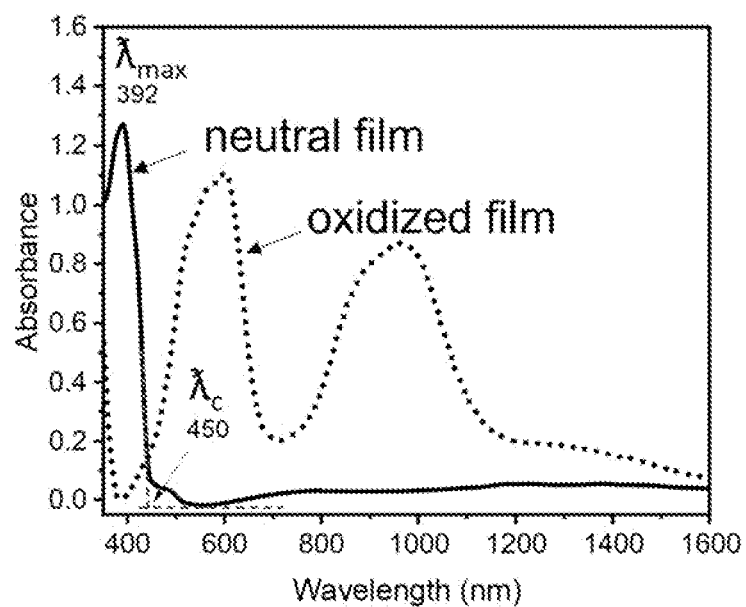
FIG. 7 are the absorbance spectra of the exemplary ECP-2 thin film at different voltages, according to one embodiment.
Figure 12:
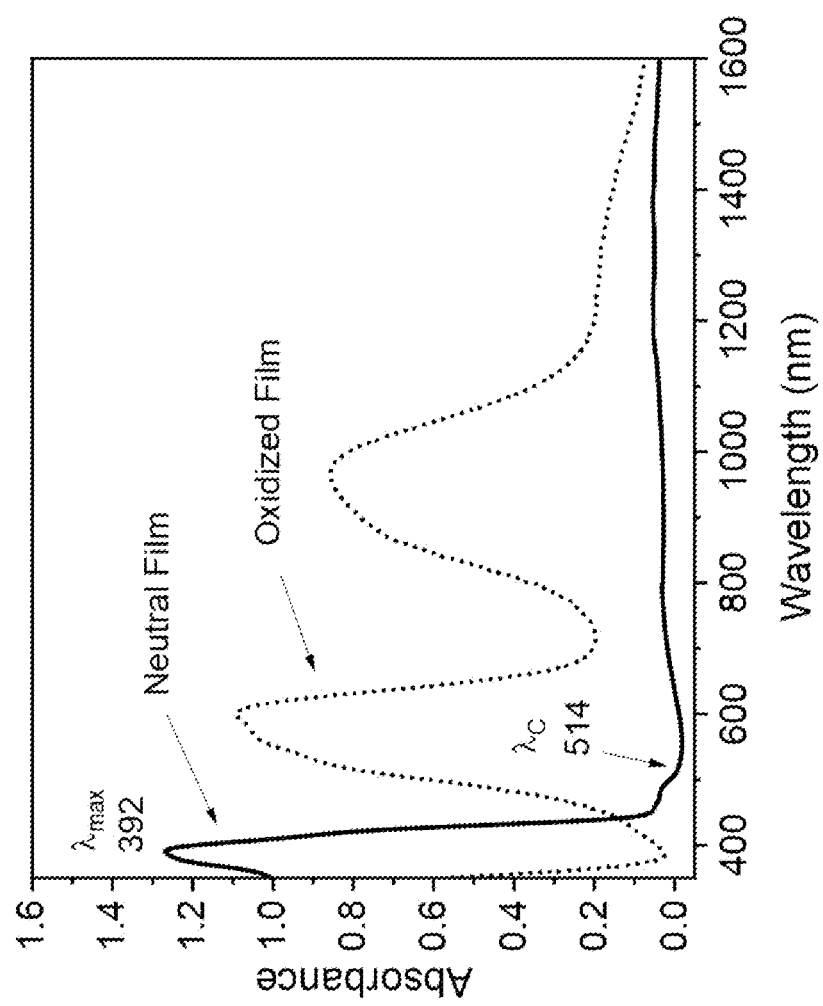
FIG. 12 shows the absorbance spectra of the exemplary ECP-2 thin film at different voltages, according to one embodiment.

The obtained ECP-2 has an oxidation potential of around 1.0 V (vs. Ag/AgCl) and an energy bandgap of higher than 2.8 eV. The ECP-2 is fabricated into a solid-state ECD with ECP-2 used as the electrochromic layer, 1M of $LiPF_6$ in PEGMEA as the electrolyte, and $VO_x$ as the ion storage layer. The solid-state ECD can be stably switched between −0.4 V to 1.2 V (FIG. 5). The neutral state and oxidized absorbance spectra of the ECP-2 are shown in FIG. 7 with $\lambda_c$ of 450 nm when the absorption onset is "defined as the x-intercept of the tangent line on the inflection point for the absorption peak of the neutral state spectra" and $\lambda_{max}$ of 392 nm. Referring to FIG. 12, the absorption onset is 514 nm when the absorption onset is defined as "the wavelength at higher than which the polymer has no photon absorption." The solid-state ECD shows a high transparency with transmittance as high as 96% in the neutral state (FIG. 6), and switches to a bright blue color when ECP-2 is oxidized with one absorption peak at about 600 nm and another boarder absorption band at the near-IR region, around 900-1100 nm (FIG. 7). The optical contrast of the solid-state ECD is about 89% (FIG. 6).

Example 3 ECP-3

In some embodiments, the disclosed ECP-3 has a formula of

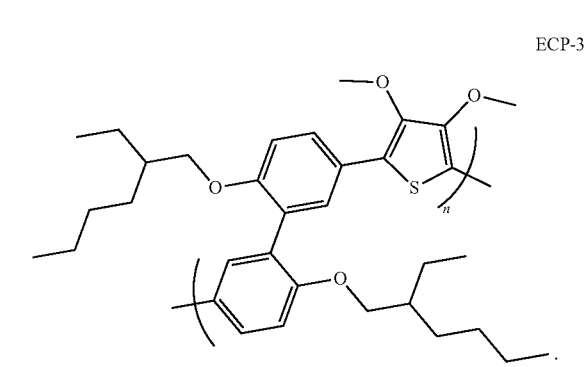

The ECP-3 is synthesized by first preparing a substituted benzene reaction unit and then polymerizing it with an acyclic dioxythiophene (AcDOT) unit. The detail method includes the following steps:

Step 3-1: same as step 2-1.
Step 3-2: polymerization: The polymerization method is similar to that in step 1-1, only differs on the reaction units.

The reaction units here are the substituted benzene reaction unit (compound 4) and AcDOT (compound 8) with a structure of

Compound 8

Figure 8:
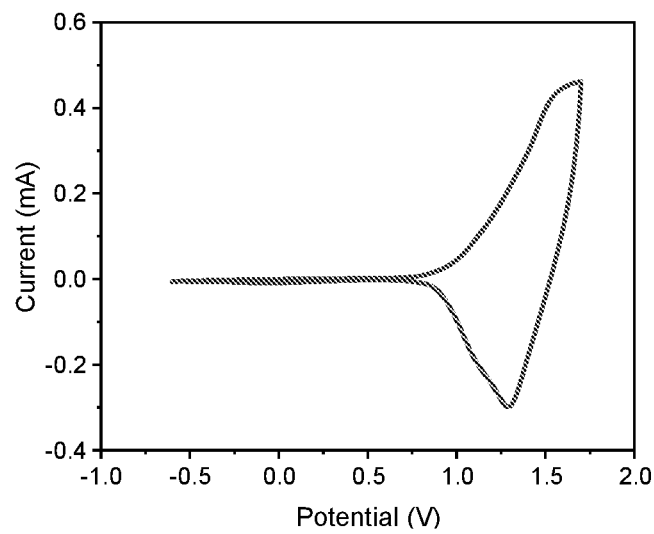
FIG. 8 is the CV data of an exemplary solid-state device using yet another example ECP-3, according to one embodiment.
Figure 9:
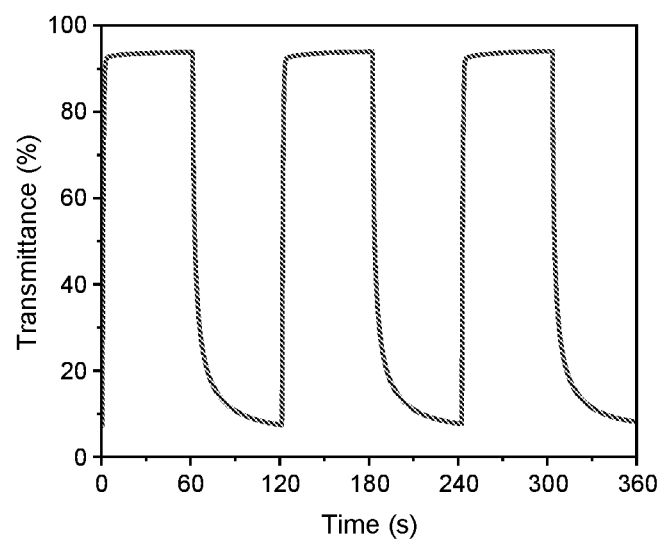
FIG. 9 is the switching kinetics of the exemplary solid-state device using the example ECP-3 at 550 nm, according to one embodiment.
Figure 10:
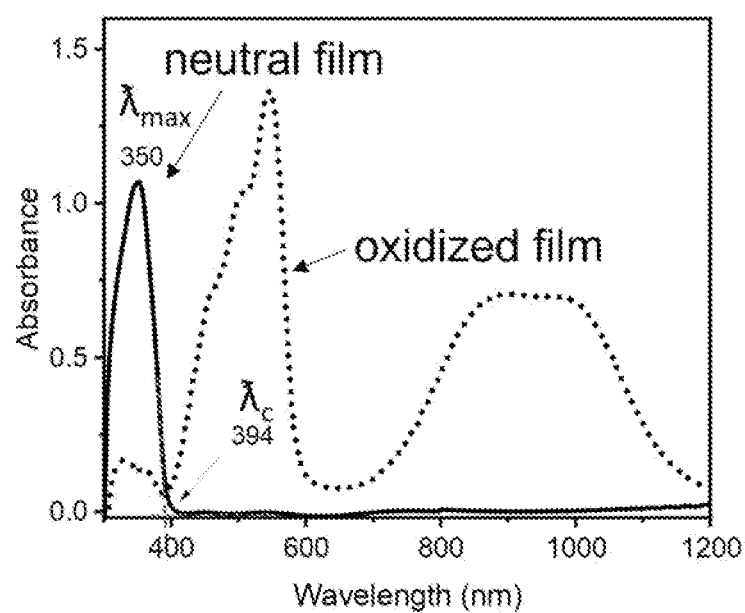
FIG. 10 are the absorbance spectra of the exemplary ECP-3 thin film at different voltages, according to one embodiment.
Figure 13:
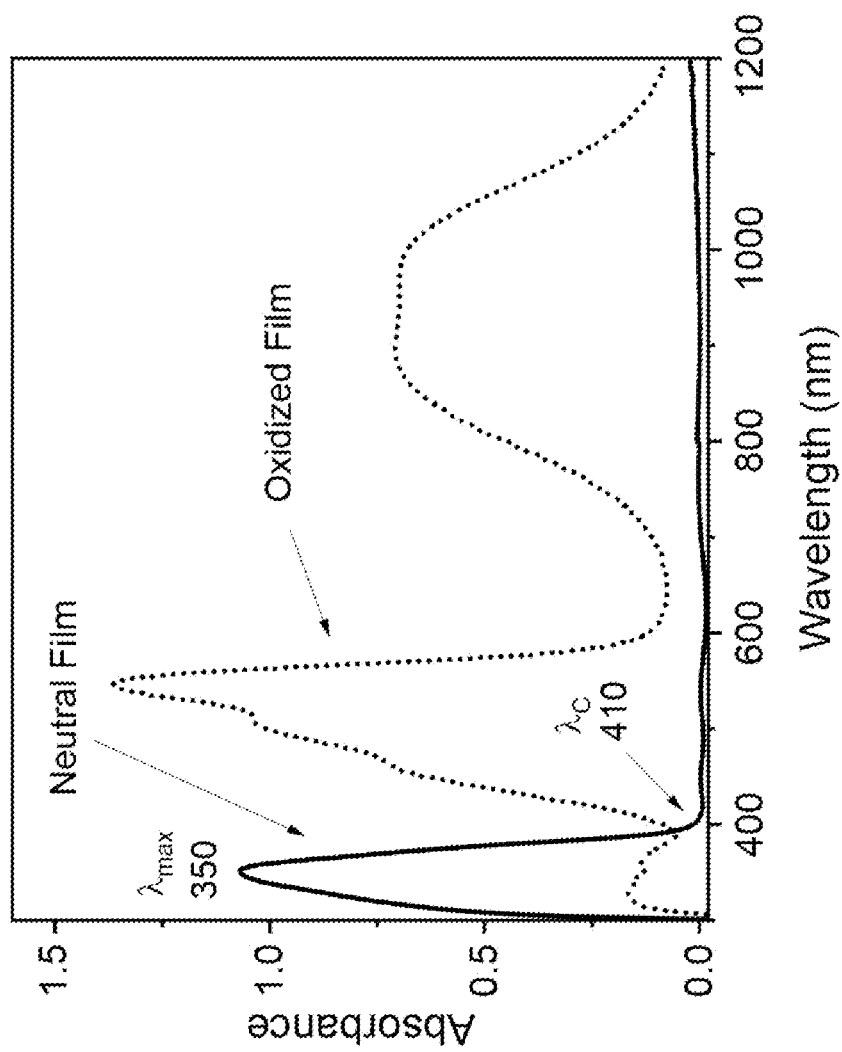
FIG. 13 shows the absorbance spectra of the exemplary ECP-3 thin film at different voltages, according to one embodiment.

The obtained ECP-3 has a oxidation potential around 0.95 V (vs. Ag/AgCl) and an energy bandgap higher than 3.1 eV. The ECP-3 is fabricated into a solid-state ECD with ECP-3 used as the electrochromic layer, 1M of $LiPF_6$ in PEGMEA as the electrolyte, and $VO_x$ as the ion storage layer. The solid-state ECD can be stably switched between −0.6 V to 1.7 V (FIG. 8). The neutral state and oxidized state absorbance spectra of the ECP-3 are shown in FIG. 10 with kc of 394 nm when the absorption onset is "defined as the x-intercept of the tangent line on the inflection point for the absorption peak of the neutral state spectra" and $\lambda_{max}$ of 350 nm. Referring to FIG. 13, the absorption onset is 410 nm when the absorption onset is defined as "the wavelength at higher than which the polymer has no photon absorption." The solid-state ECD shows high transparency with transmittance as high as 94% at neutral state at 550 nm (FIG. 9), and switches to bright red color when ECP-3 is oxidized with one absorption peak at around 546 nm and another broader absorption band at the wavelength around 800-1100 nm (FIG. 10). The optical contrast of the solid-state ECD is 87% (FIG. 9).

Example 4 ECP-4

In some embodiments, the disclosed ECP-4 has a formula of

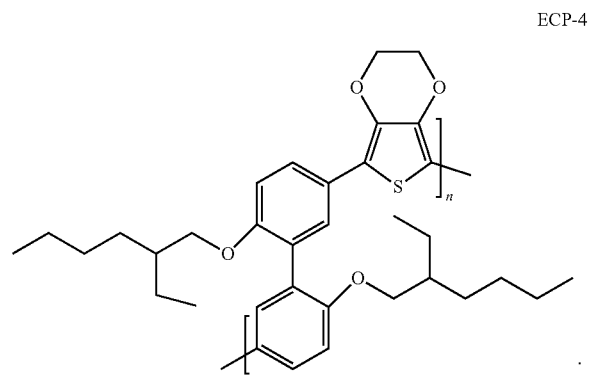

ECP-4

ECP-4 is synthesized by preparing a benzene-containing reaction unit and polymerizing it with a ProDot unit. The detail method includes the following steps:

Step 4-1: the same as Step 2-1

Step 4-2: polymerization: The polymerization method is similar to that in step 1-1, only differs on the reaction units. The reaction units here are benzene-containing reaction unit (compound 4) and 3, 4-Ethylenedioxythiophene (EDOT, compound 9) with a structure of

Compound 9

Example 5 ECP-5

In some embodiments, the disclosed ECP has a formula of

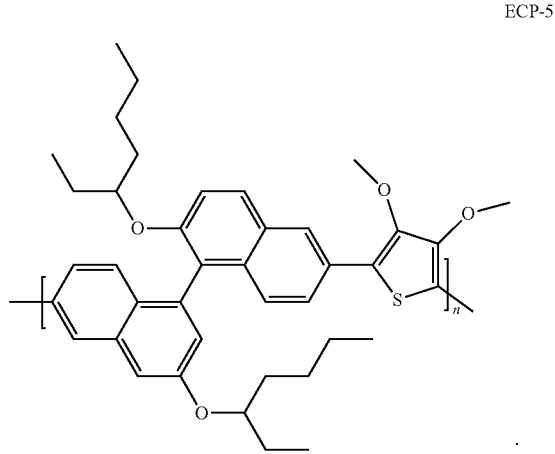

ECP-5

The ECP-5 is synthesized by preparing a naphthalene-containing reaction unit and then polymerizing it with an AcDOT unit. The detail method includes the following steps:

Step 5-1: preparing naphthalene-containing reaction unit (compound 10) by two steps.

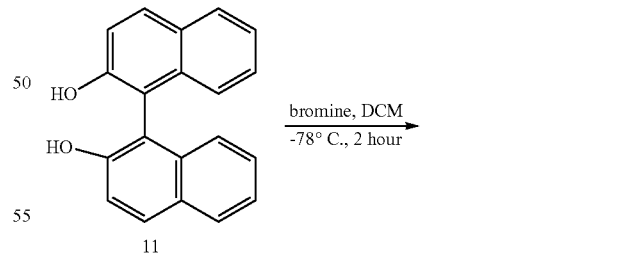

11

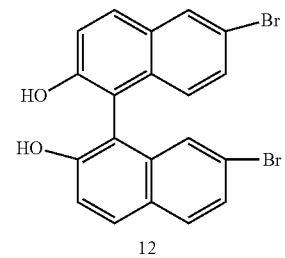

12

41

To a solution of compound 11 in dichloromethane was added dropwise a solution of bromine in dichloromethane over 15 minutes at −78° C. The reaction mixture is stirred for 2 hours at −78° C. and then warmed gradually to room temperature and stay at room temperature for an additional 2 hours. The excess bromine was quenched by saturated aqueous sodium sulfite solution and stirred for 2 hours at room temperature. After extraction with dichloromethane, the combined organic layer was washed with brine, dried over sodium sulfate, and concentrated in vacuum.

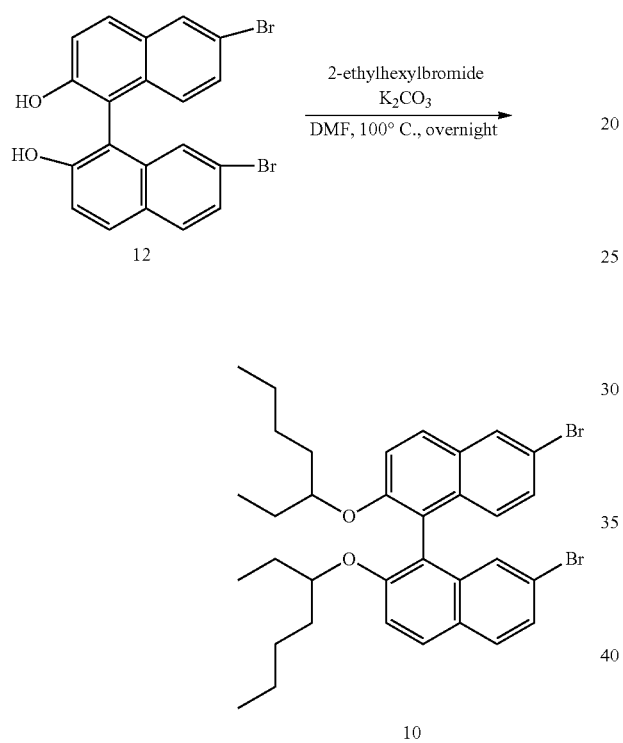

Compound 12 is dissolved in DMF under $N_2$, $K_2CO_3$ is added to the solution, and the reaction mixture is stirred for 15 minutes, after which 2-ethylexyl bromide is added. The reaction mixture is stirred at 100° C. overnight. The reaction is stopped and cooled down to room temperature. The solvent is removed in vacuum, and the residue is dissolved in diethyl ether. The organic phase is washed with water, and the aqueous phases are extracted with ethyl acetate. The combined organic phases are dried by vacuum.

Step 5-2: polymerization: The polymerization method is similar to that in step 1-1, only differs on the reaction units. The reaction units here are the naphthalene-containing reaction unit (compound 10) and AcDOT (compound 8).

42

Example 6 ECP-6

In some embodiments, the disclosed ECP has a formula of

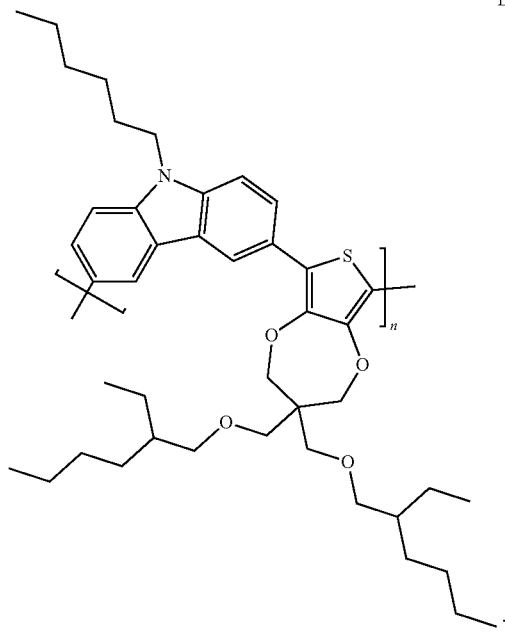

ECP-6

The ECP-6 is synthesized by a carbazole reaction unit polymerized with a ProDot unit. The detail method includes the following step:

Step 6-1: polymerization: polymerization method is similar to that in step 1-1, only differs on the reaction units. The reaction units here are the carbazole reaction unit (compound 13) with a structure of

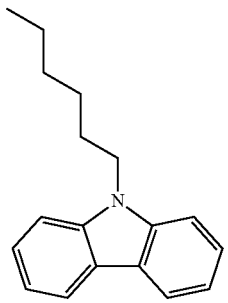

Compound 13 and a ProDOT (compound 3).

In some embodiments, the disclosed ECP has a formula of
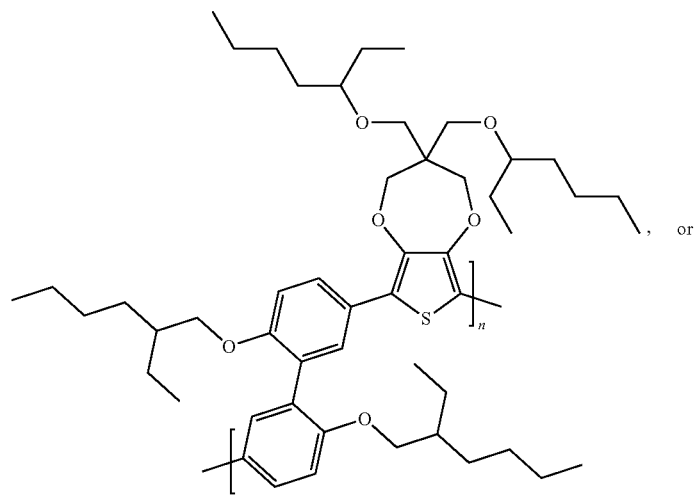
ECP-7
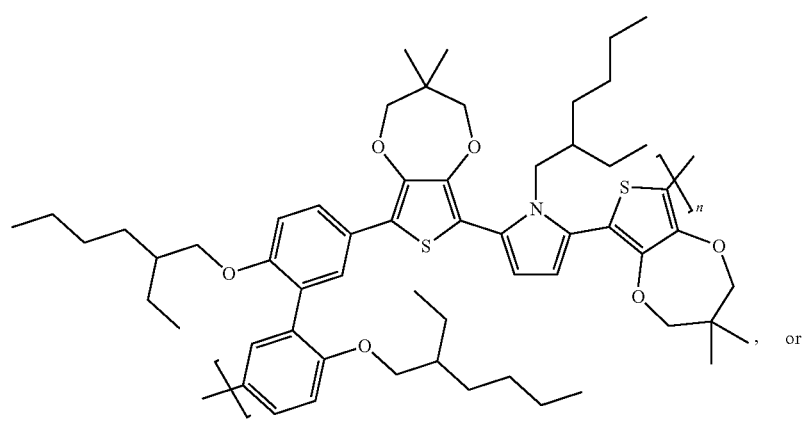
ECP-8
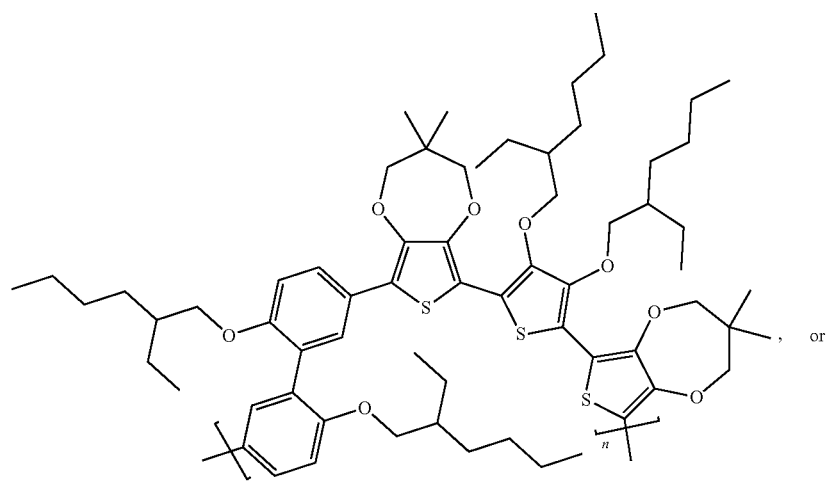
ECP-9

-continued

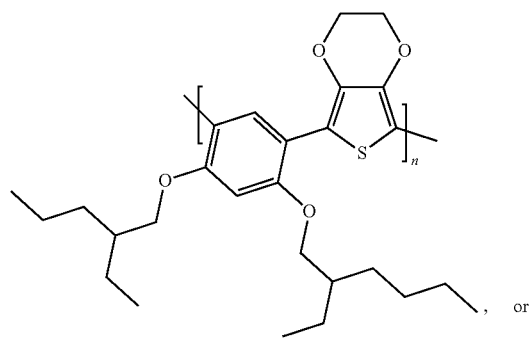

ECP-10

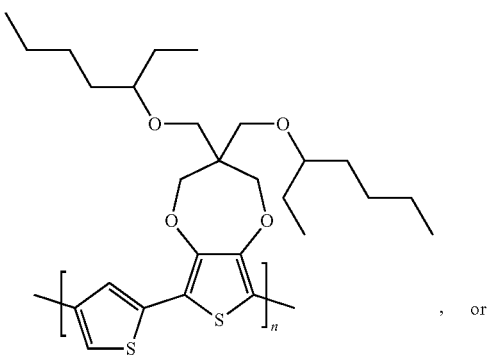

ECP-11, or

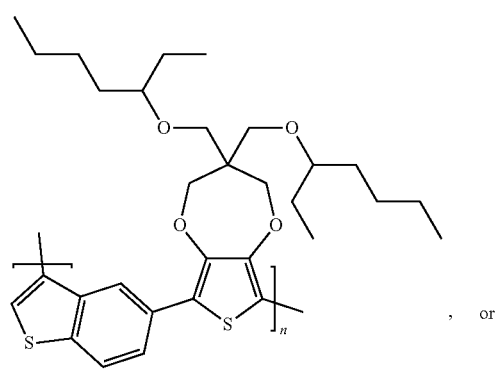

ECP-12, or

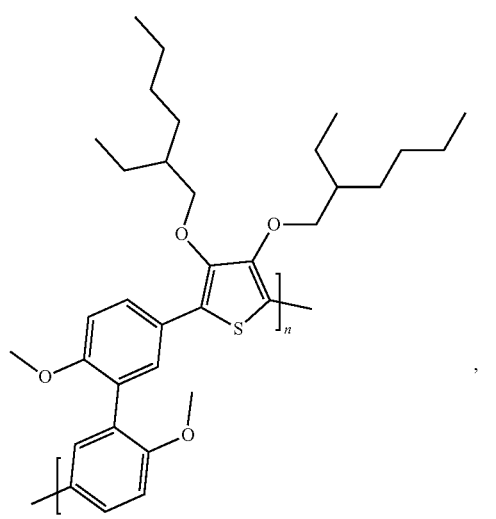

ECP-13, or

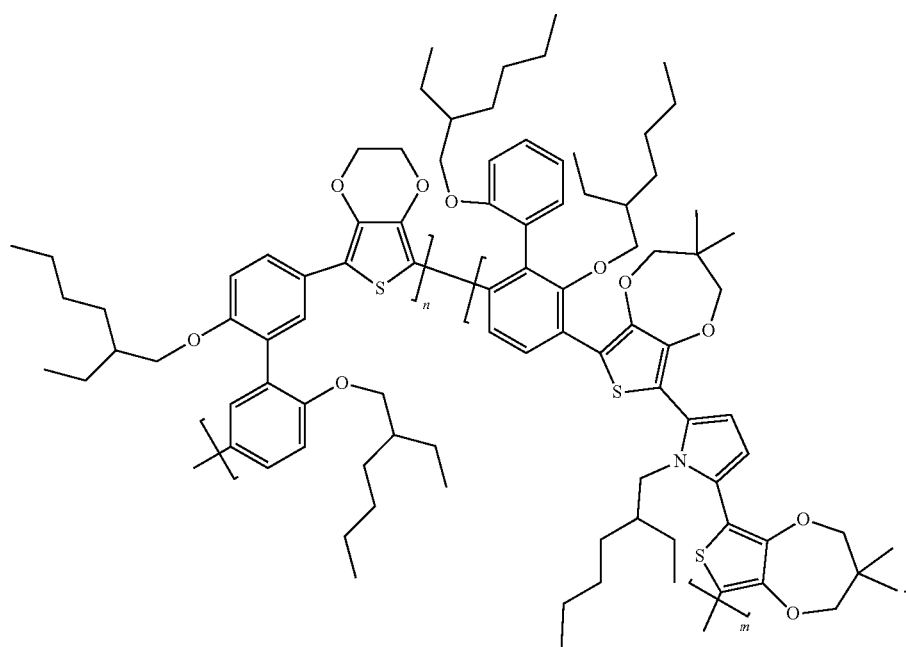

ECP-14

In another aspect, the disclosed polymers can have fluorescent emission and can be applied to fluorescent products.

The foregoing description of the present disclosure has been provided for the purposes of illustration and description. It is not intended to be exhaustive or to limit the disclosure to the precise forms disclosed. The breadth and scope of the present disclosure should not be limited by any of the above-described exemplary embodiments. Many modifications and variations will be apparent to the practitioner skilled in the art. The modifications and variations include any relevant combination of the disclosed features. The embodiments were chosen and described in order to best explain the principles of the disclosure and its practical application, thereby enabling others skilled in the art to understand the disclosure for various embodiments and with various modifications that are suited to the particular use contemplated. It is intended that the scope of the disclosure be defined by the following claims and their equivalence.

What is claimed is:

1. An electrochromic polymer, consisting of:
   a polymer backbone comprising one or more meta-conjugated linkers (MCLs) and one or more aromatic moieties (Ars), wherein each of the one or more MCLs is partially conjugated with the one or more Ars at meta positions of the one or more MCLs,
   wherein the electrochromic polymer is colorless in a neutral state, and the electrochromic polymer has absorption in visible and near-infrared wavelengths in an oxidized state,
   wherein each of the one or more MCLs and corresponding meta positions comprise one of the following formulas:

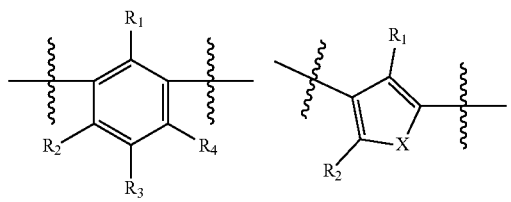

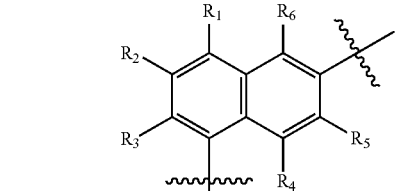

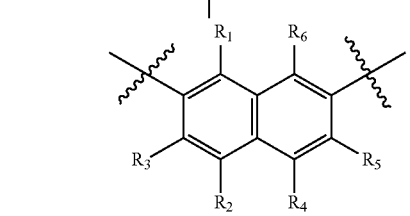

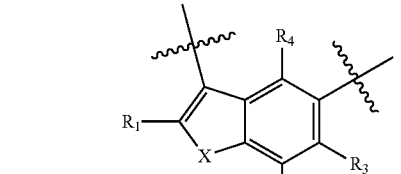

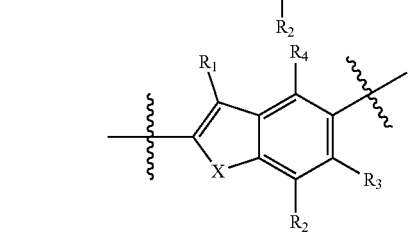

-continued

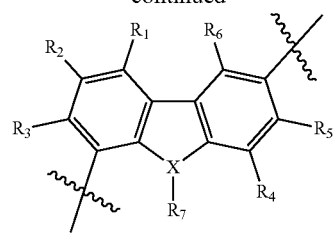

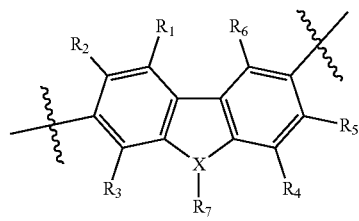

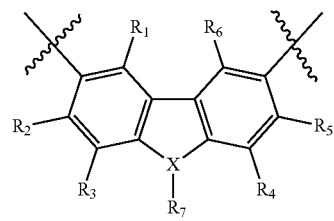

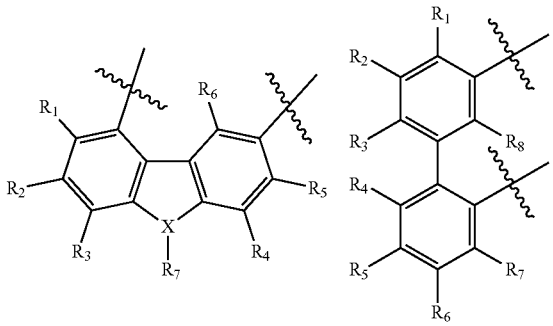

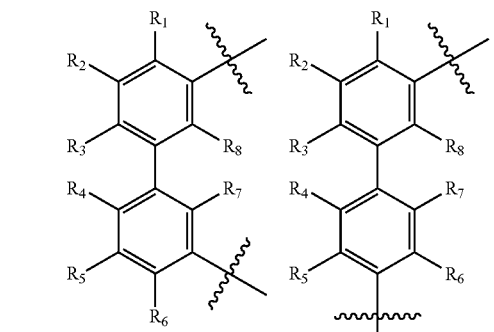

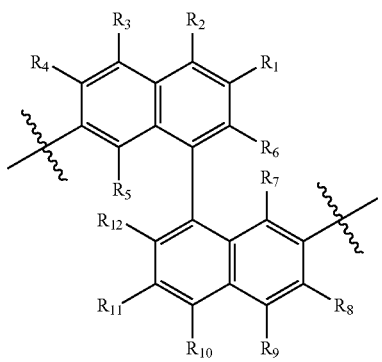

49
-continued
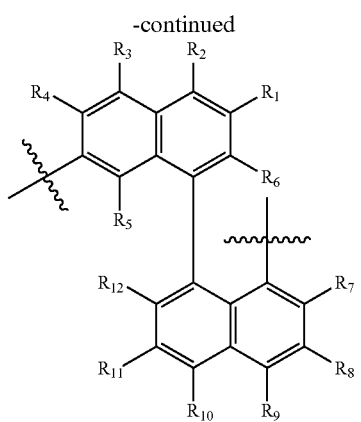
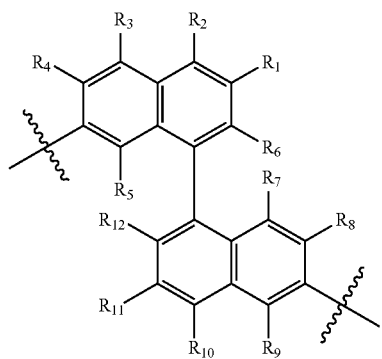
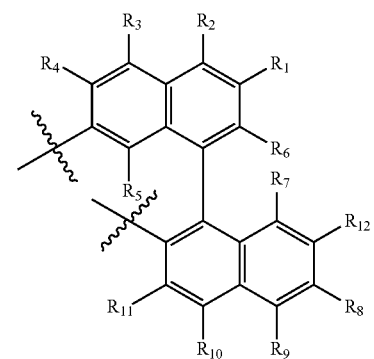
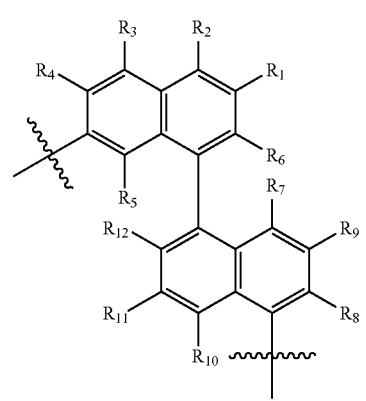
50
-continued
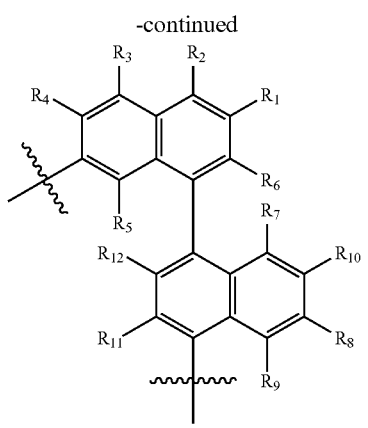
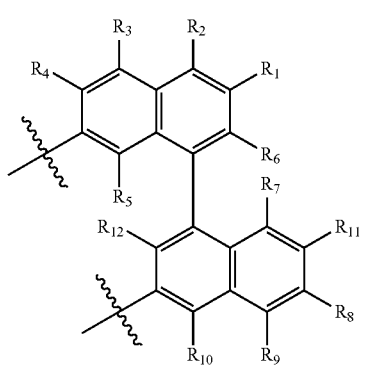
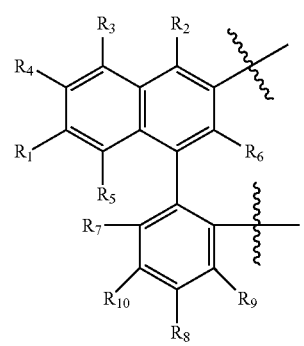
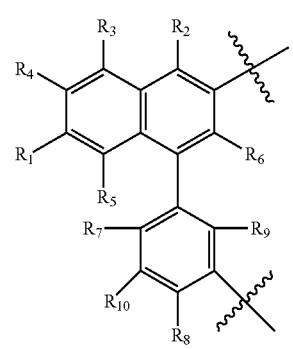

51
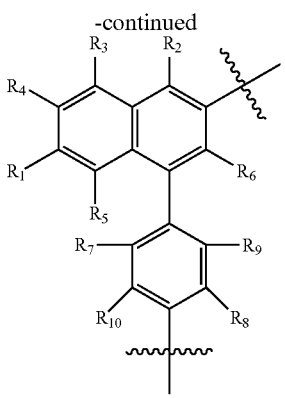
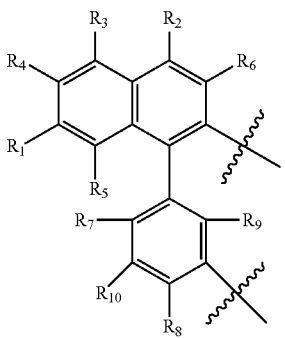
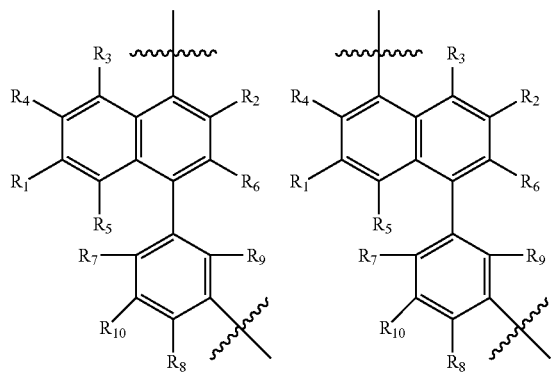
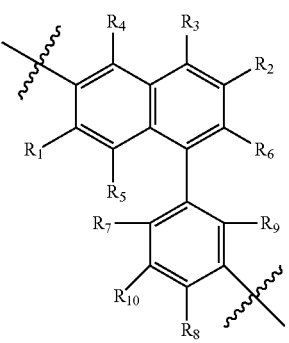
52
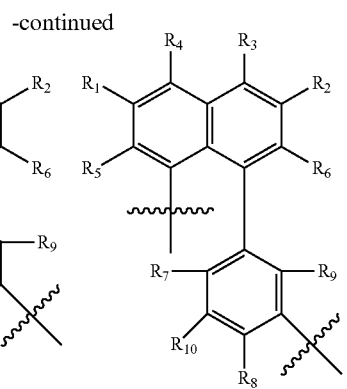
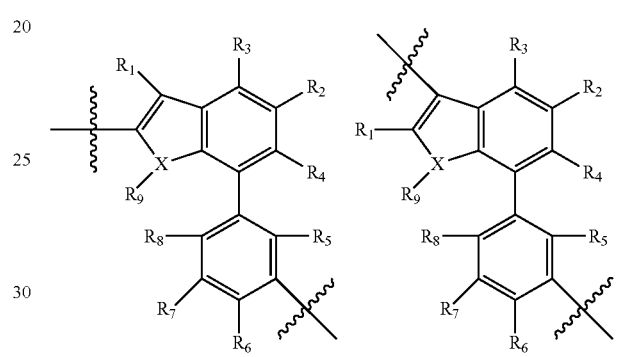
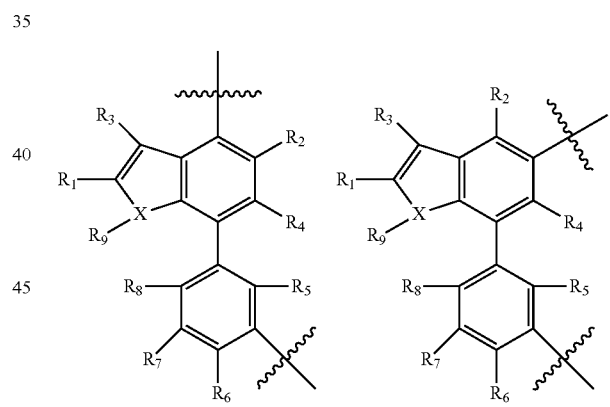
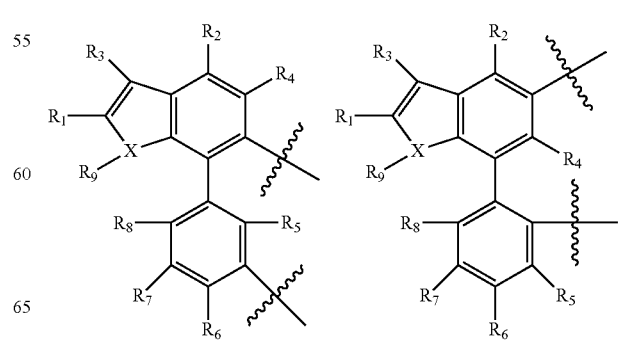

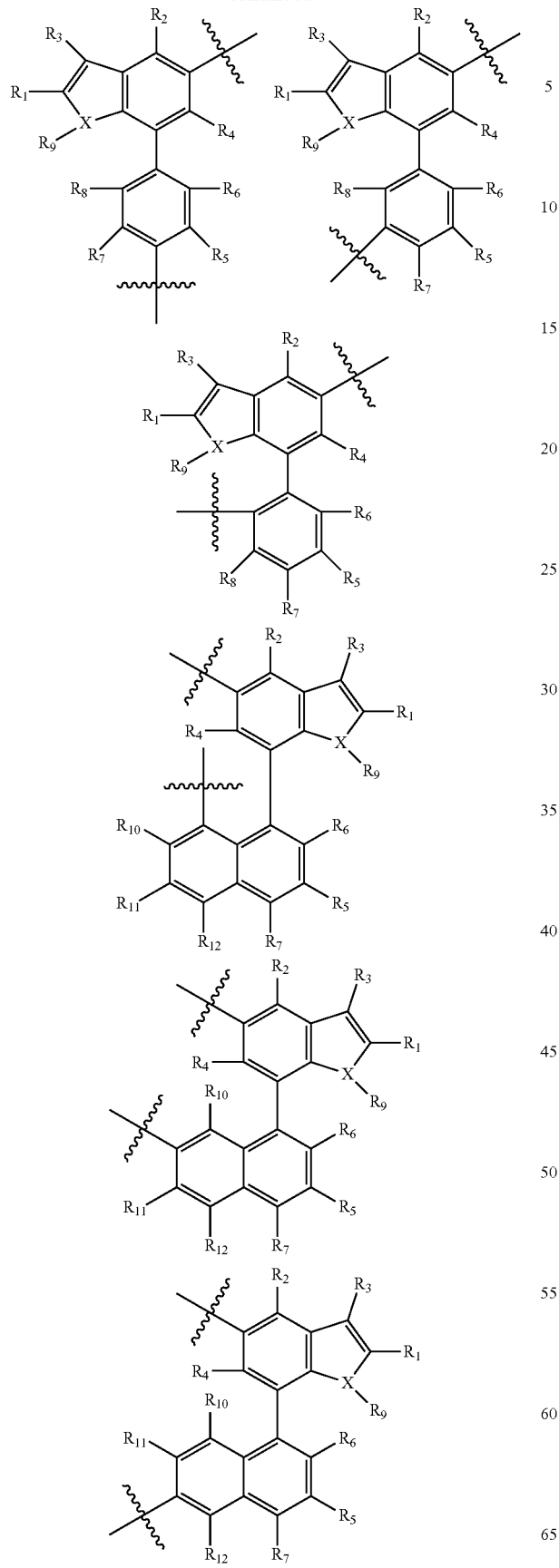
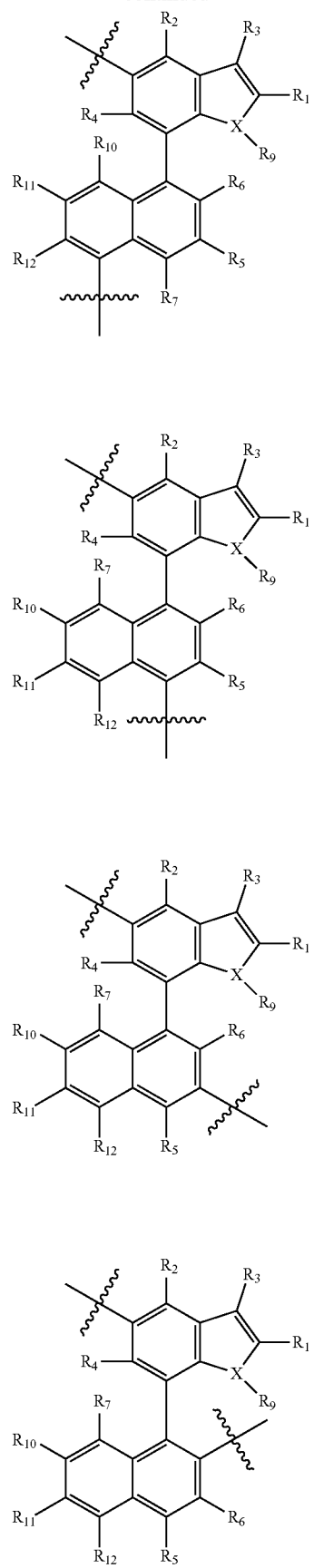

-continued

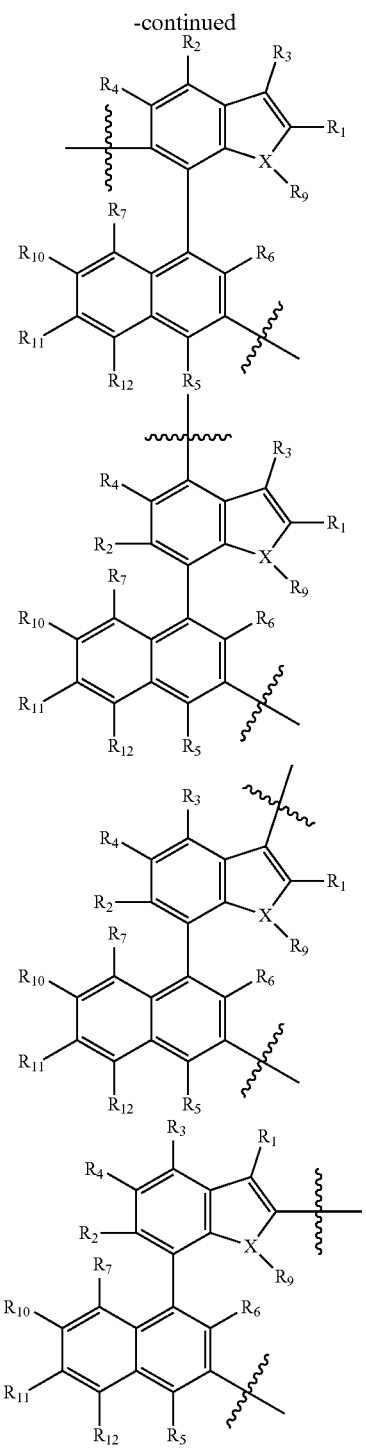

wherein X is S, Se, N, or O: each of $R_1$-$R_{12}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl; and each of the wavy lines represents one of the meta positions, and wherein each of the one or more Ars comprises one of a thiophene-based unit, a furan-based unit, a selenophene-based unit, or a pyrrole-based unit respectively with a formula of:

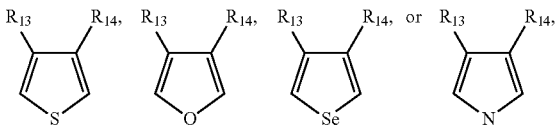

or a combination thereof, wherein each of $R_{13}$ and $R_{14}$ is independently selected from one of hydrogen, $C_1$-$C_{30}$alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

2. An electrochromic polymer, consisting of:

a polymer backbone comprising one or more meta-conjugated linkers (MCLs) and one or more aromatic moieties (Ars), wherein each of the one or more MCLs is partially conjugated with the one or more Ars at meta positions of the one or more MCLs, wherein the electrochromic polymer is colorless in a neutral state, and the electrochromic polymer has a peak absorption coefficient larger than $10^4$ cm$^{-1}$ at 360 nm-1600 nm in an oxidized state, wherein each of the one or more MCLs and corresponding meta positions comprise one of the following formulas:

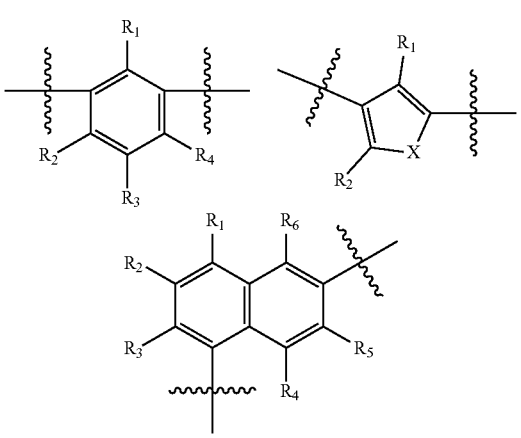

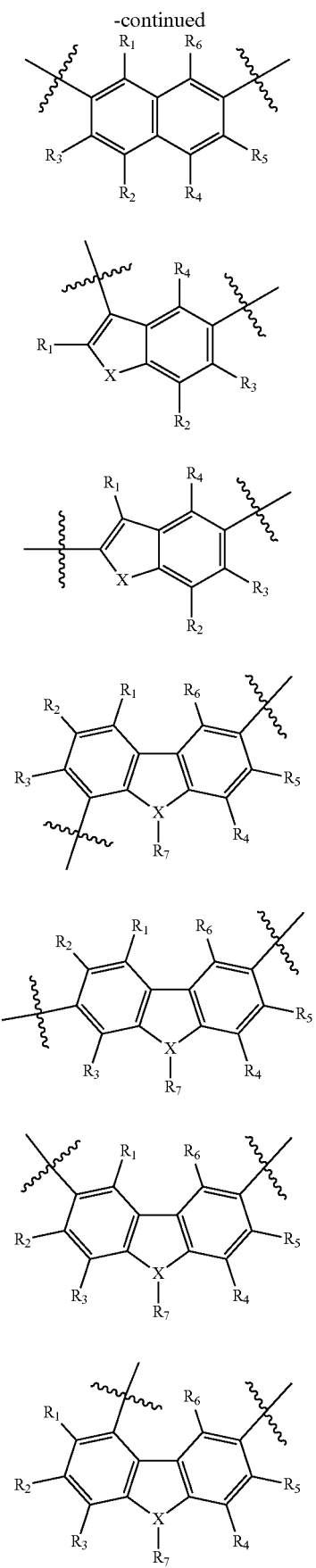
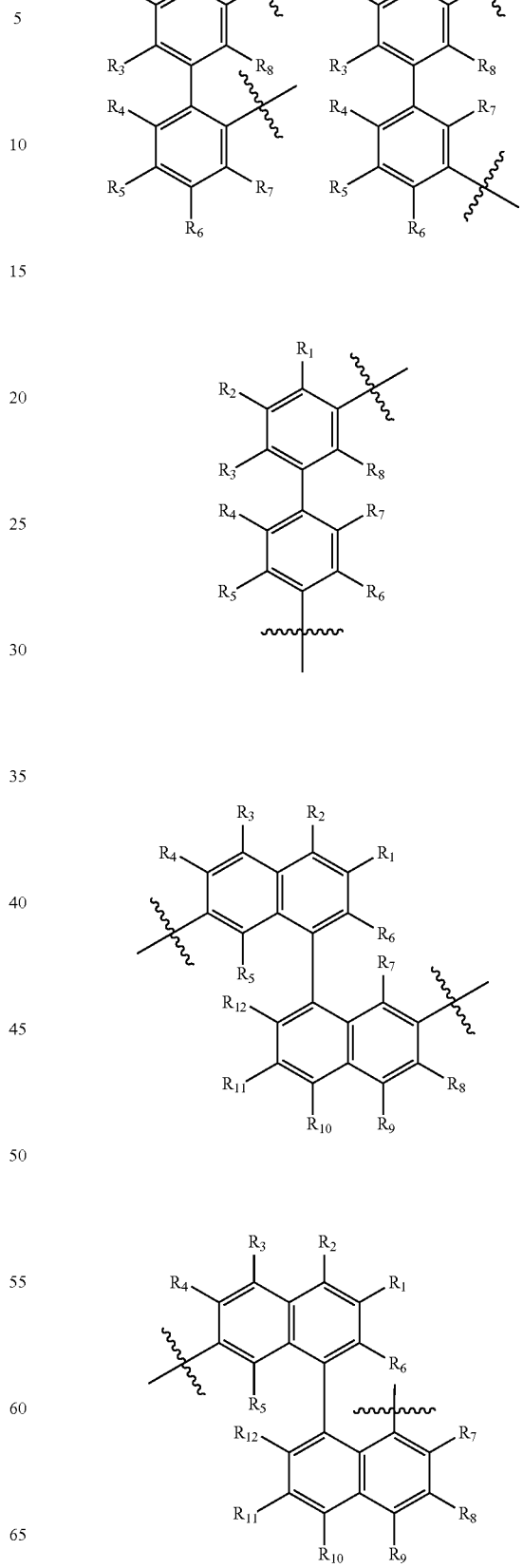

-continued
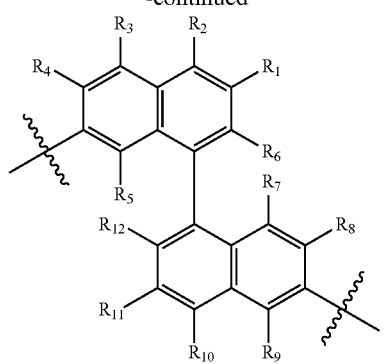
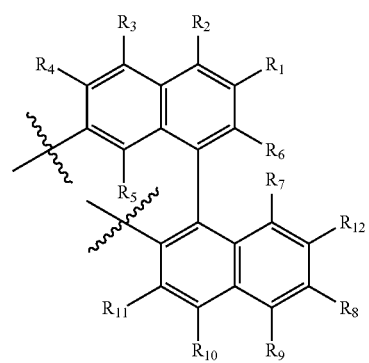
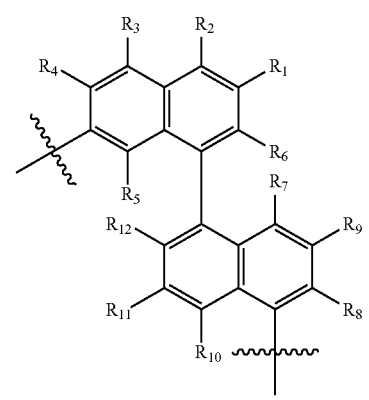
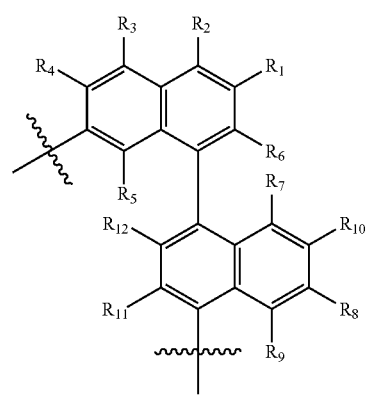
-continued
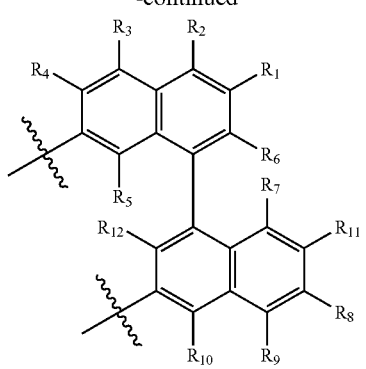
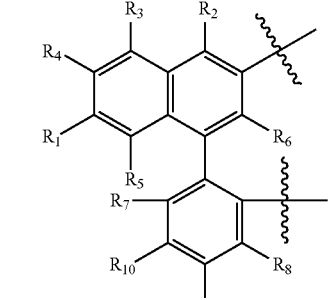
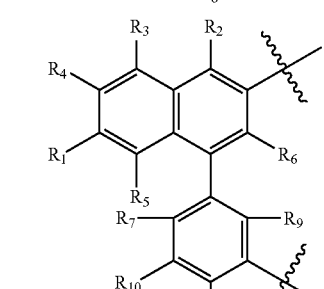
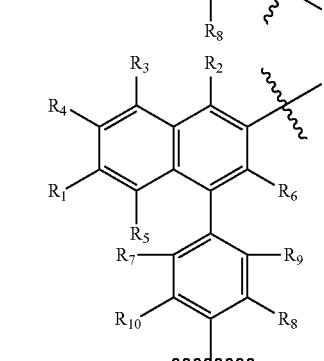
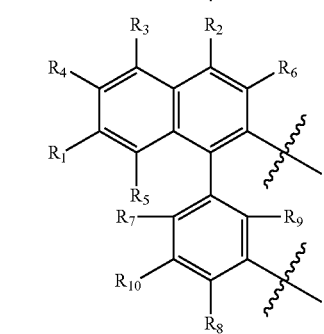

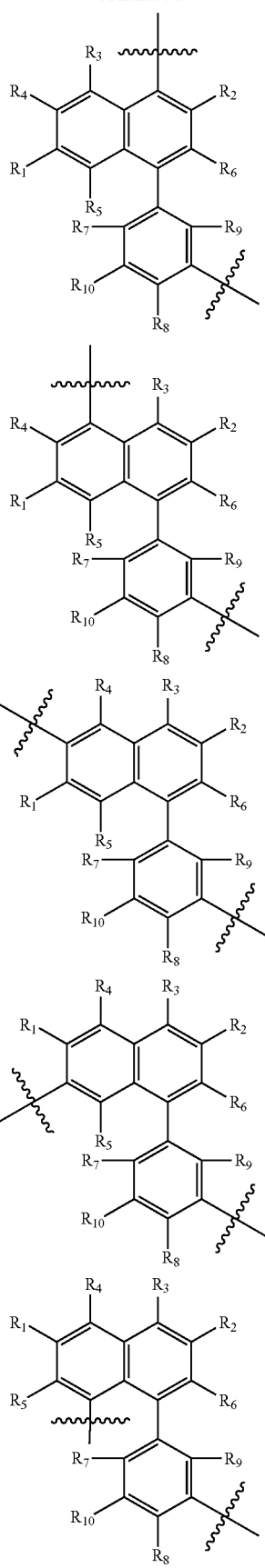
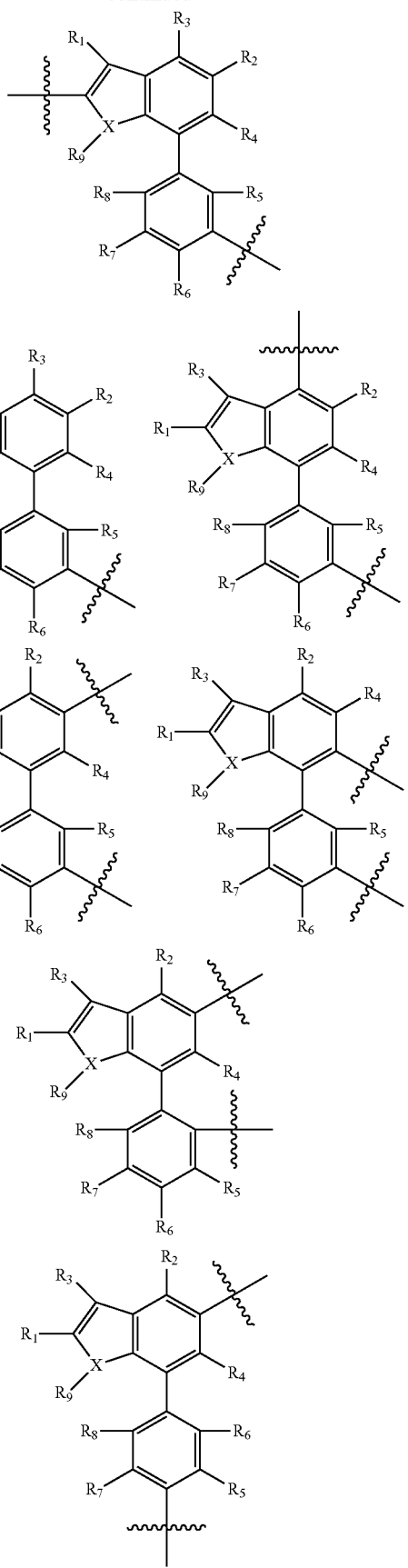

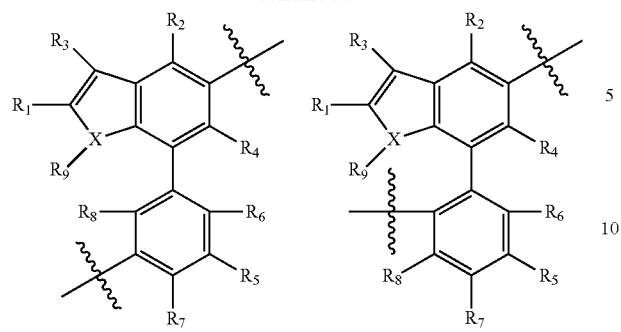
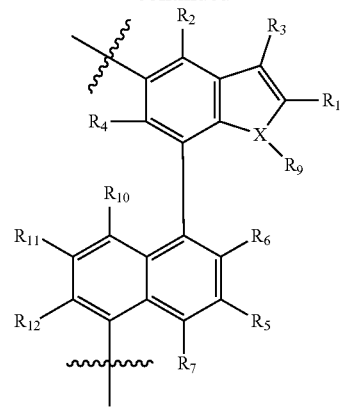
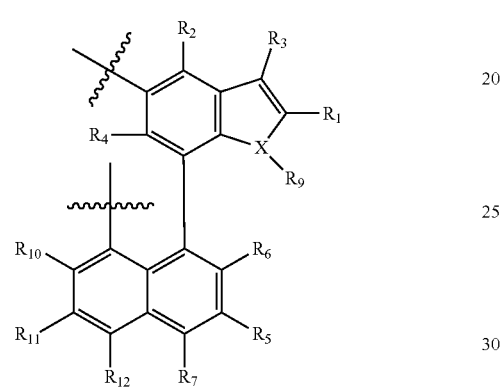
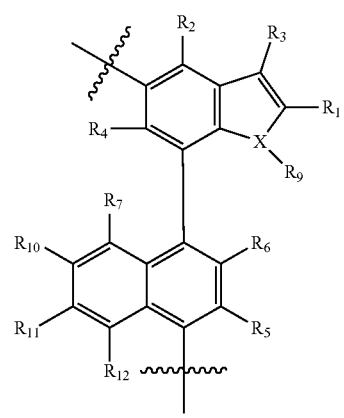
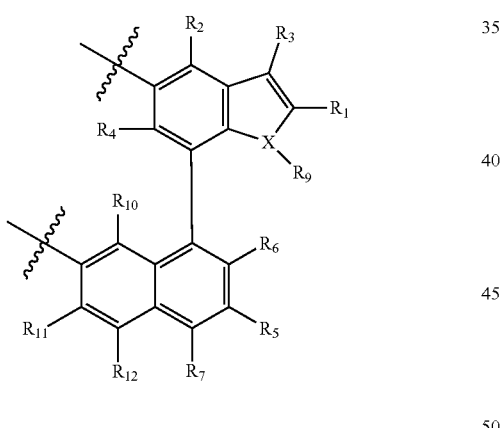
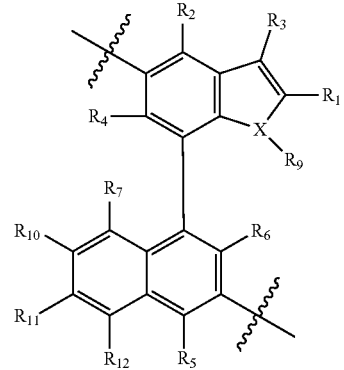
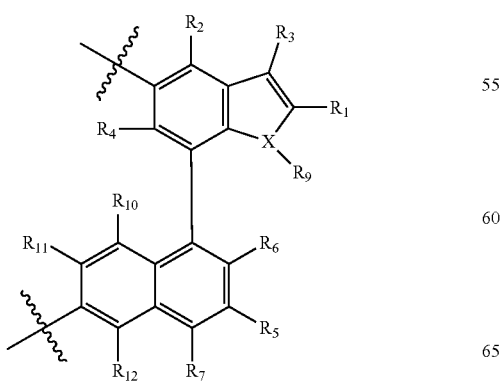
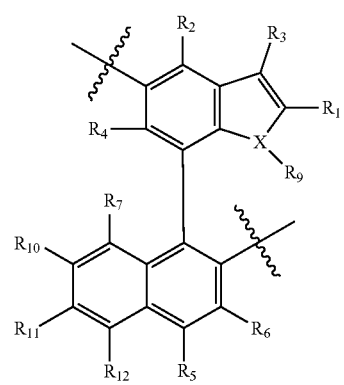

-continued

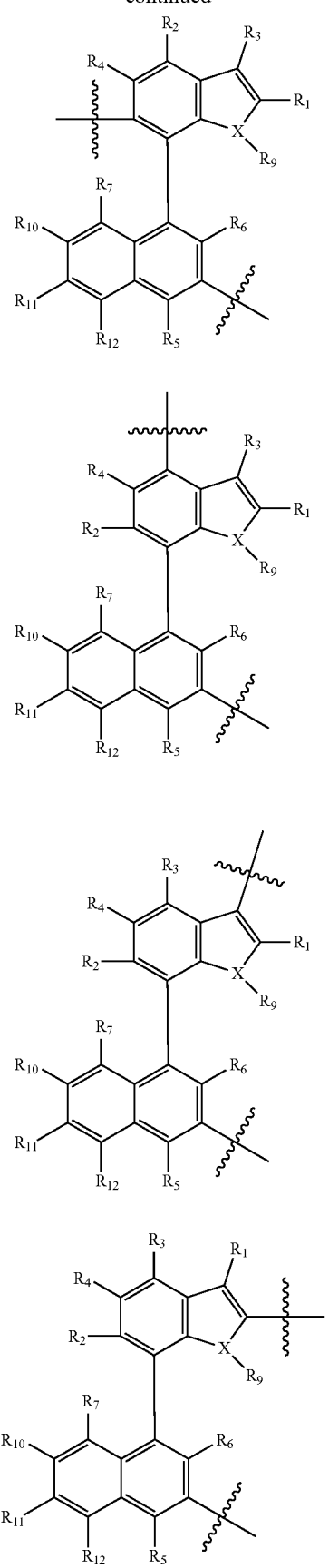

wherein X is S, Se, N, or O: each of $R_1$-$R_{12}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-Cis aryl, $C_3$-Cis cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl; and each of the wavy lines represents one of the meta positions, and wherein each of the one or more Ars comprises one of a thiophene-based unit, a furan-based unit, a selenophene-based unit, or a pyrrole-based unit respectively with a formula of:

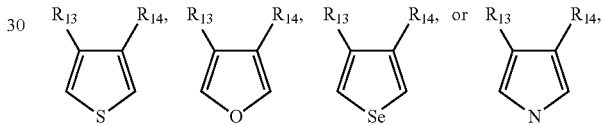

or a combination thereof, wherein each of $R_{13}$ and $R_{14}$ is independently selected from one of hydrogen, $C_1$-$C_{30}$alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-Cis aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

3. The electrochromic polymer of claim 1, wherein the one or more MCLs and the one or more Ars are arranged in an alternative fashion with a formula of

wherein each of n and $m_1, m_2, \ldots, m_n$ is an integer greater than 0.

4. The electrochromic polymer of claim 1, wherein the thiophene-based unit comprises a formula of

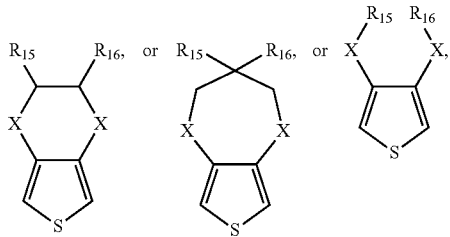

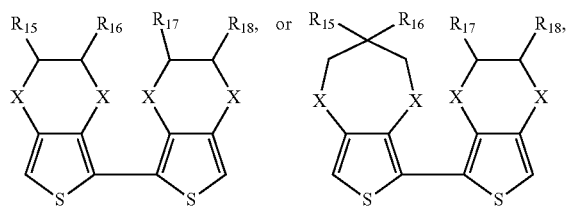

or

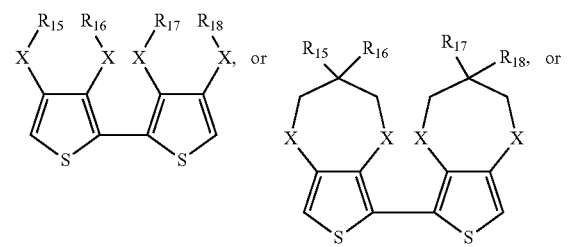

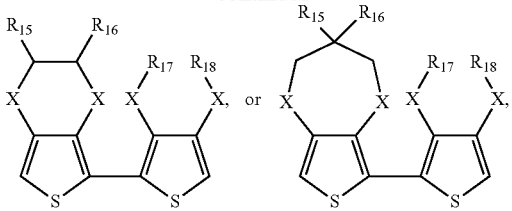

or a combination thereof, wherein X is S, Se, N, or O; each of $R_{15}$-$R_{18}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

5. The electrochromic polymer of claim 4, wherein X in the thiophene-based unit is O.

6. The electrochromic polymer of claim 1, wherein the electrochromic polymer comprises a formula of

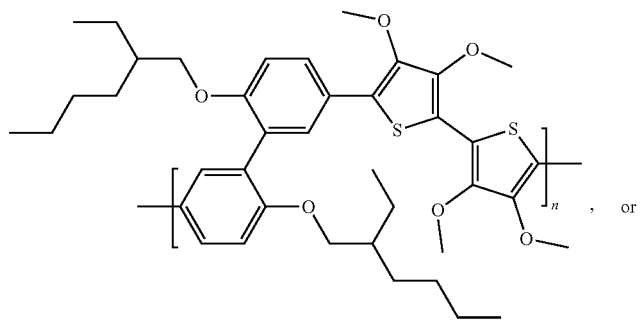, or

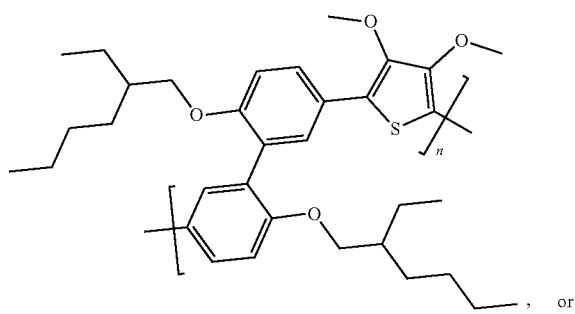, or

-continued
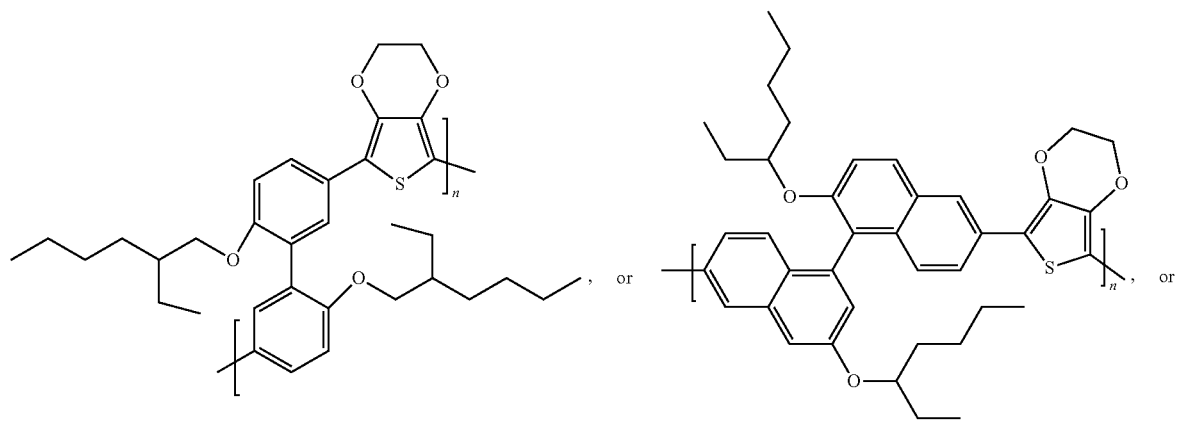
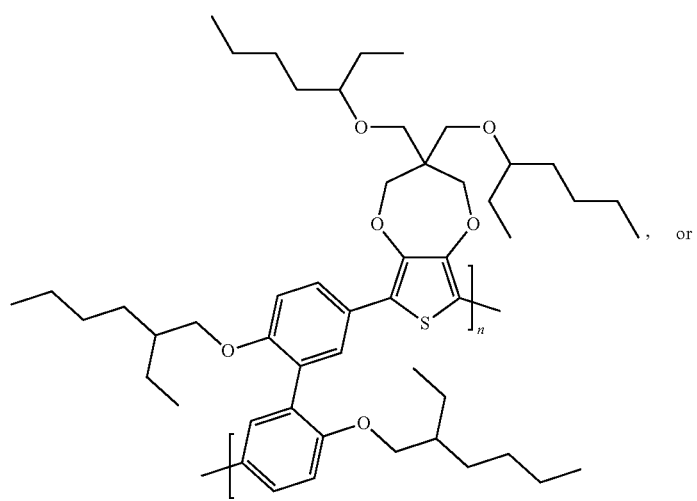
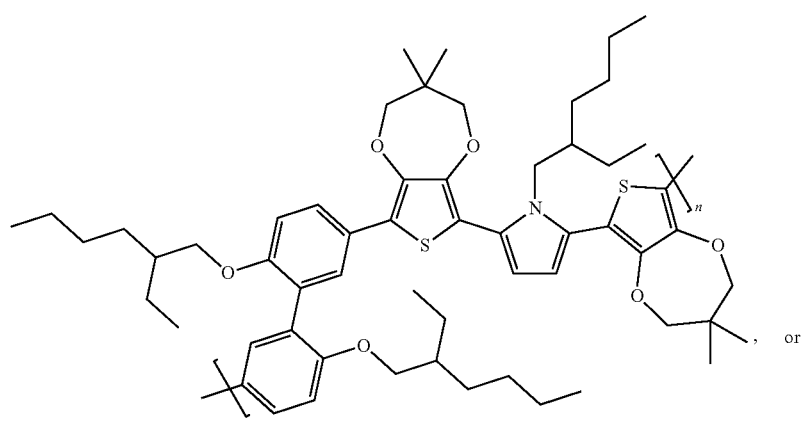

-continued
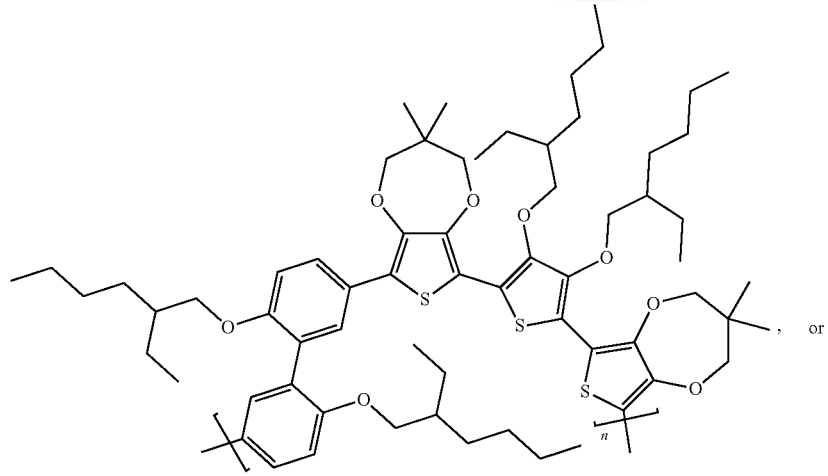
, or
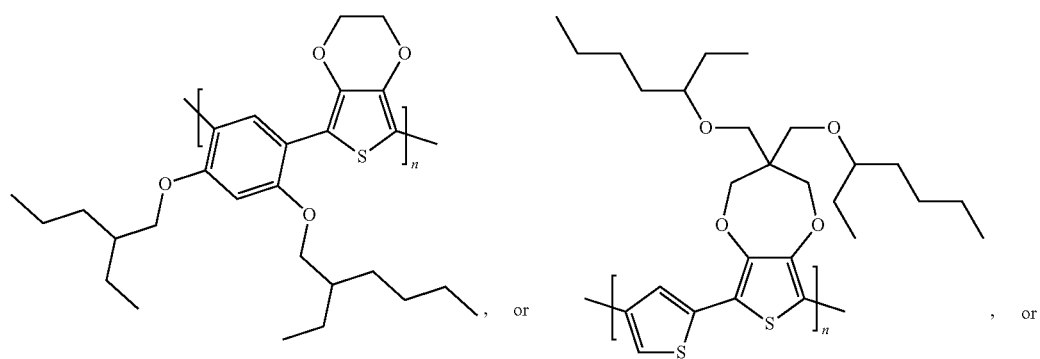
, or
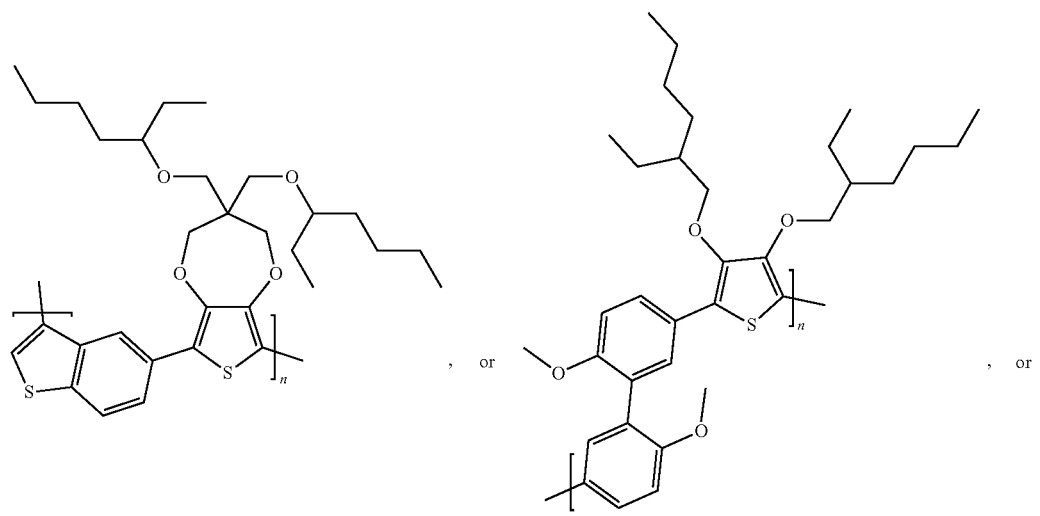
, or

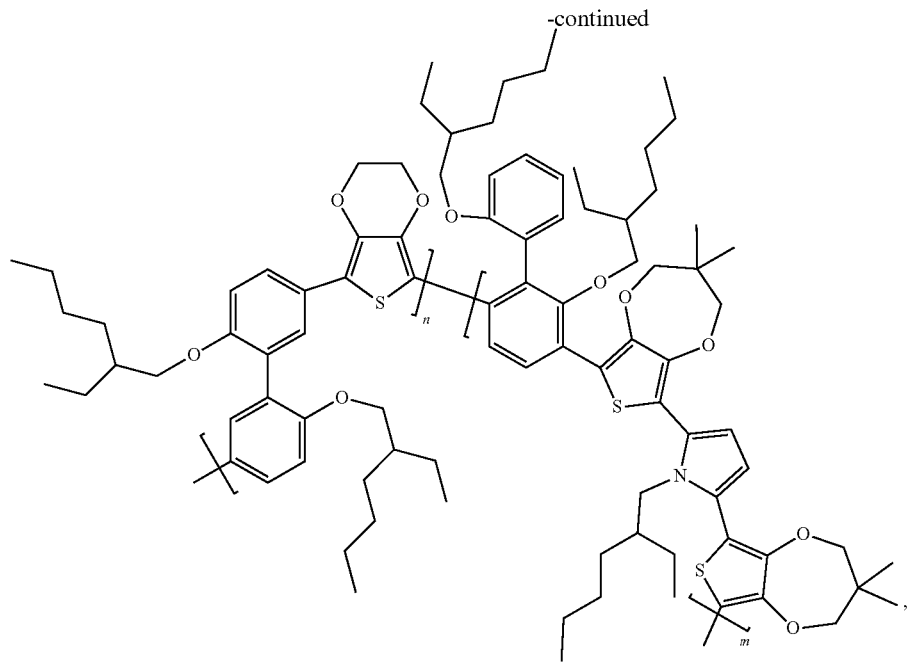

wherein n and m are integers greater than 0.

7. The electrochromic polymer of claim 3, wherein the thiophene-based unit comprises a formula of

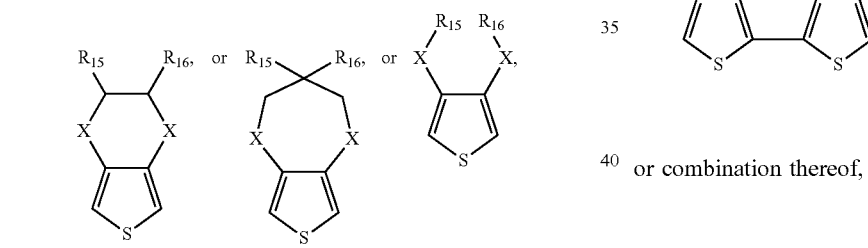

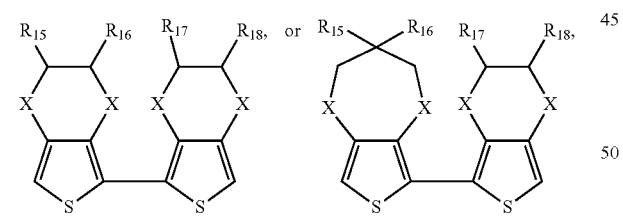

or

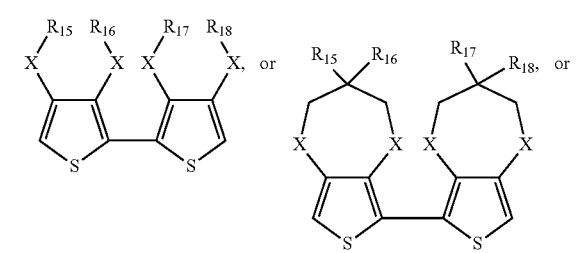

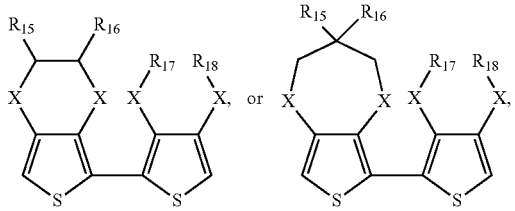

or combination thereof, wherein X is S, Se, N, or O; each of $R_{15}$-$R_{18}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

8. The electrochromic polymer of claim 2, wherein the electrochromic polymer comprises a formula of
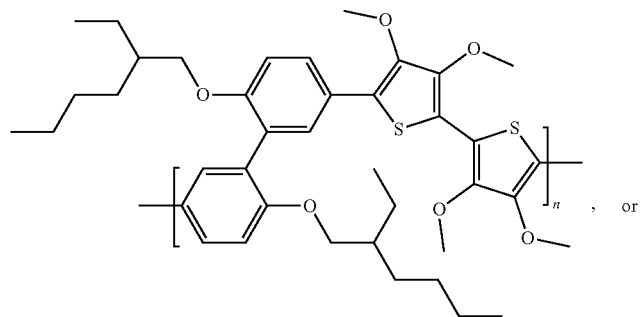
, or
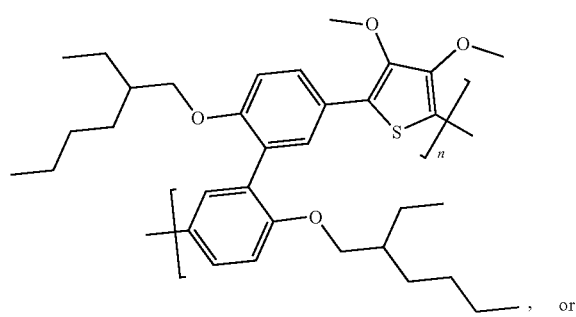
, or
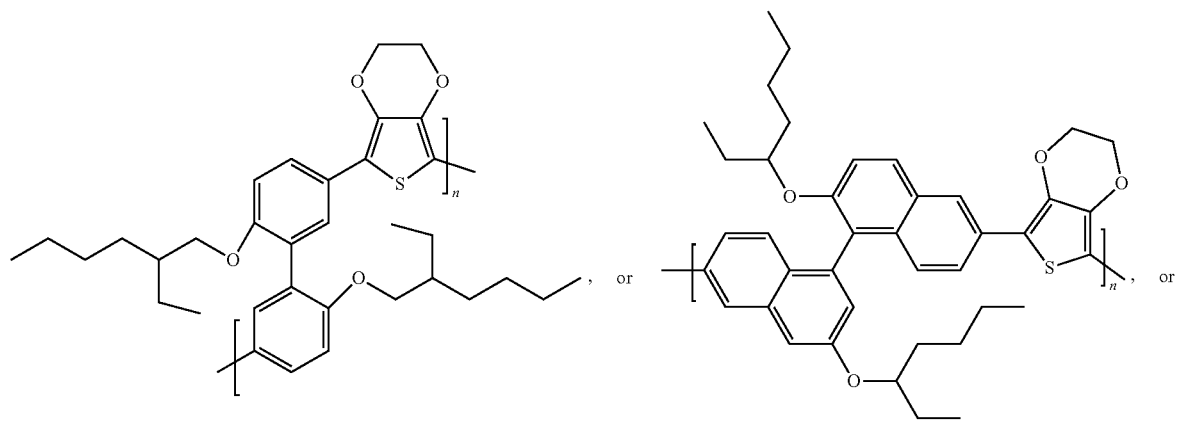
, or
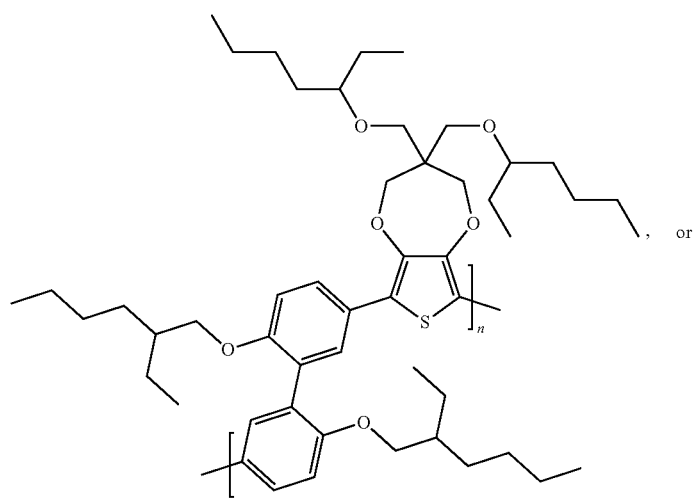
, or

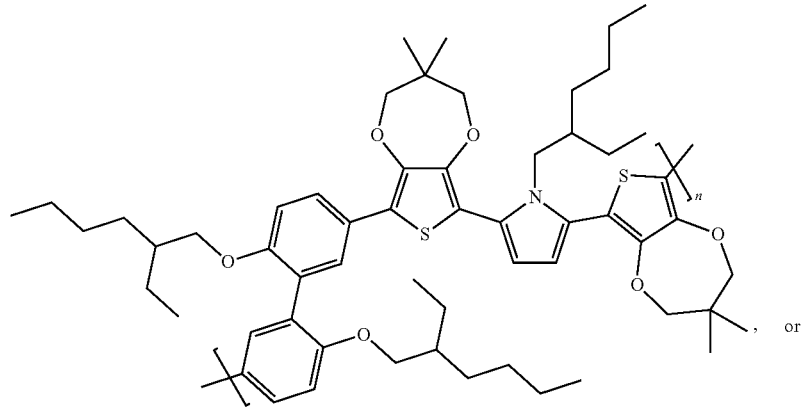
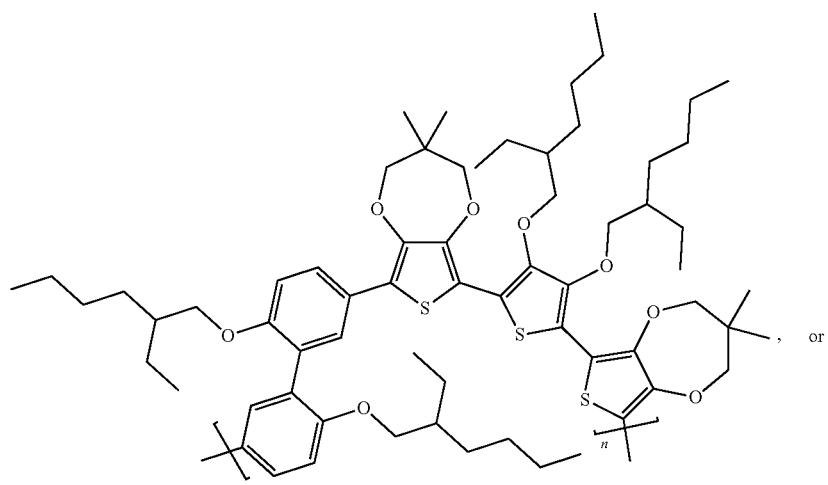
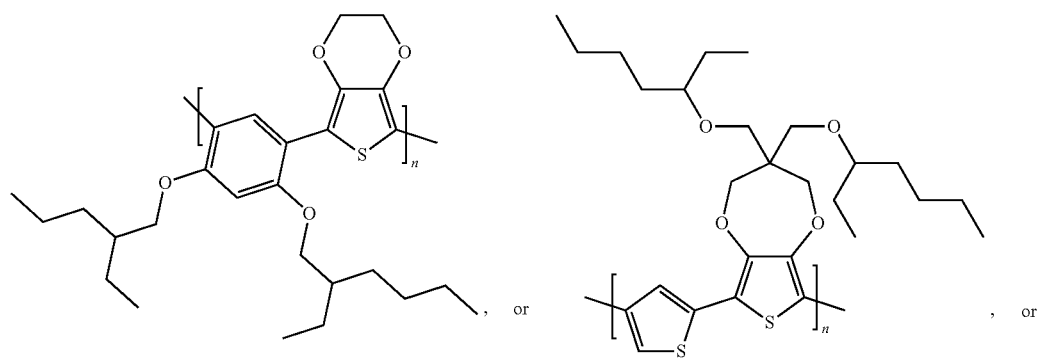

-continued

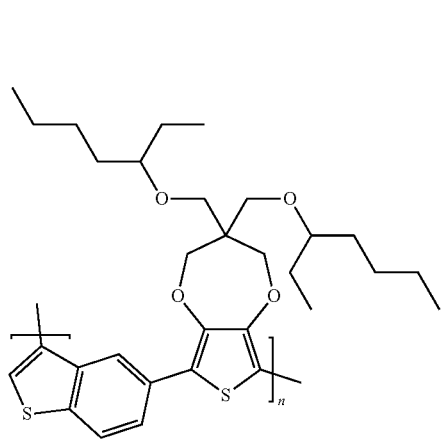
, or
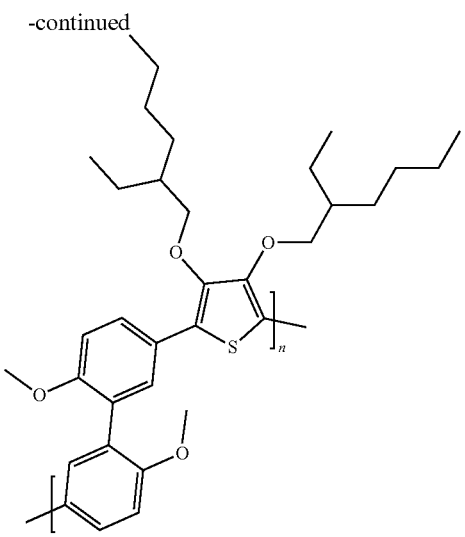
, or

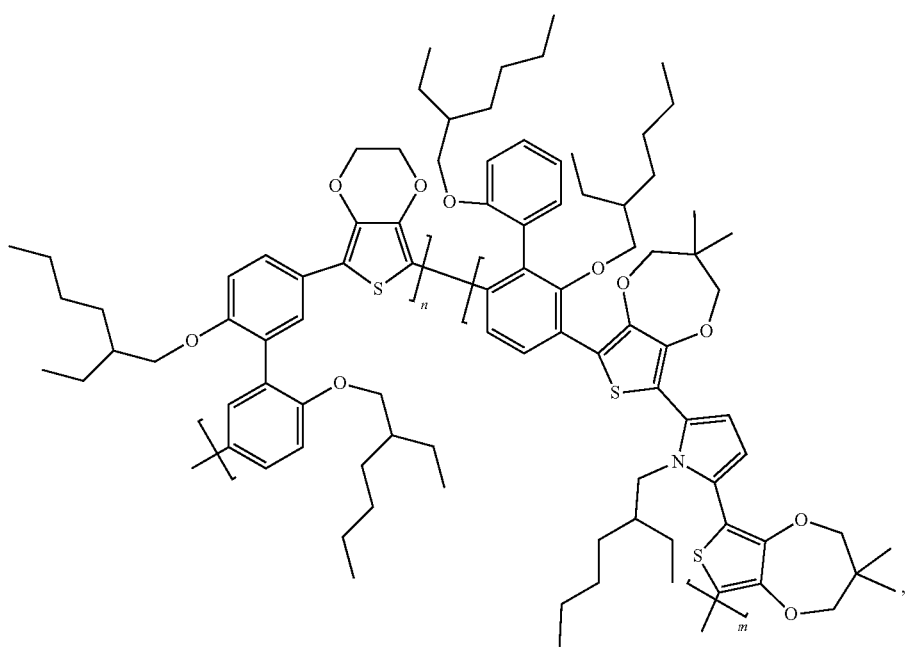

wherein n and m are integers greater than 0.

9. An electrochromic polymer, consisting of:

a polymer backbone comprising one or more meta-conjugated linkers (MCLs) and one or more aromatic moieties (Ars), wherein each of the one or more MCLs is partially conjugated with the one or more Ars at meta positions of the one or more MCLs, wherein the electrochromic polymer has an absorption onset at 410 nm or less in a neutral state, wherein the absorption onset indicates a wavelength at higher than which the electrochromic polymer has no photon absorption, and the electrochromic polymer has absorption in visible and near-infrared wavelengths in an oxidized state, wherein each of the one or more MCLs and corresponding meta positions comprise one of the following formulas:

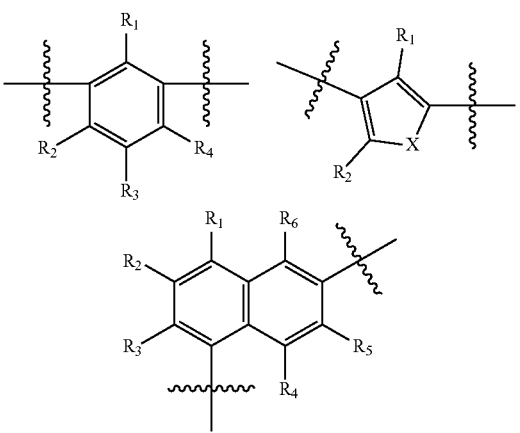

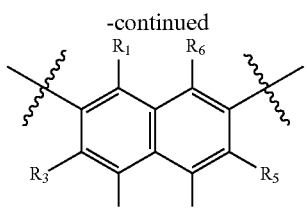
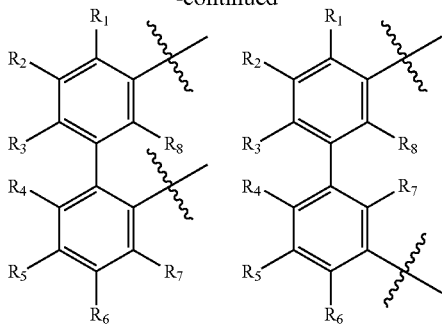
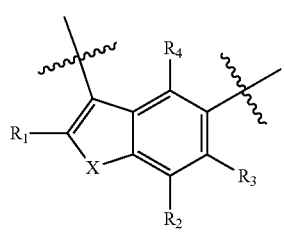
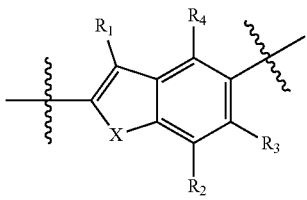
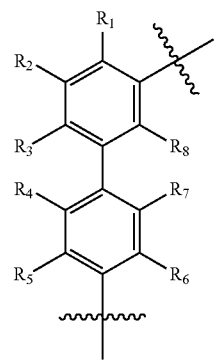
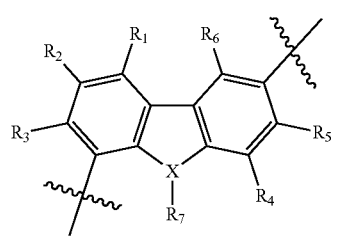
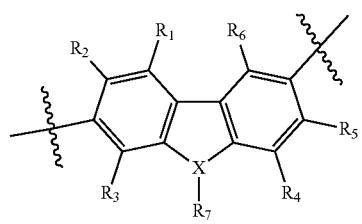
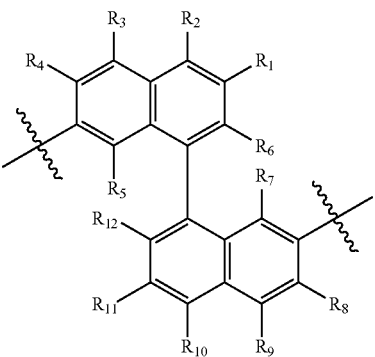
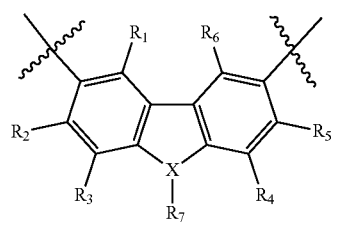
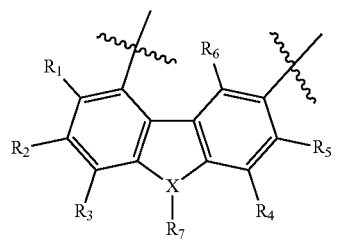
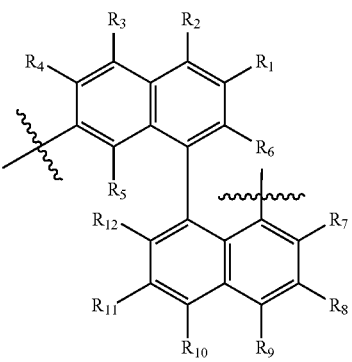

-continued
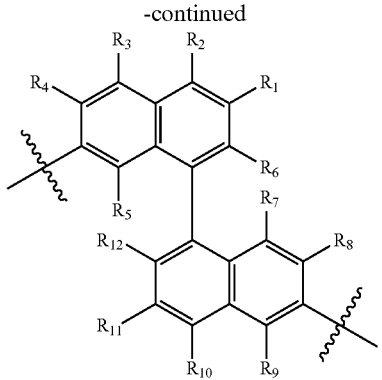
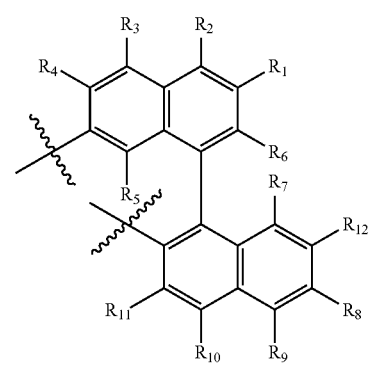
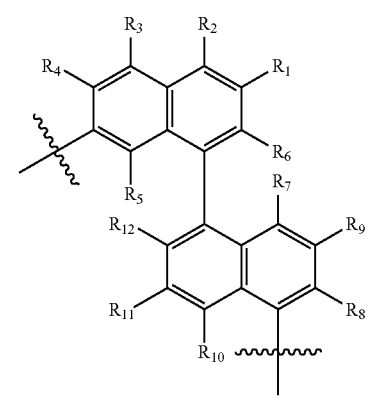
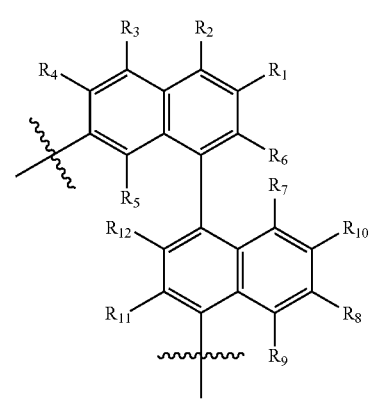
-continued
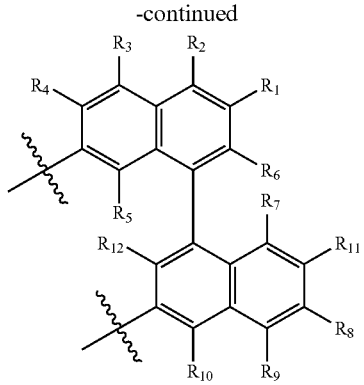
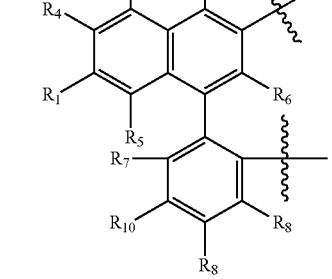
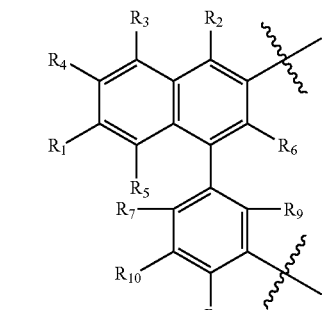
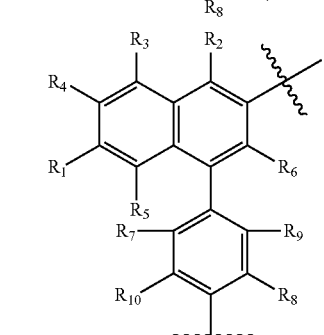
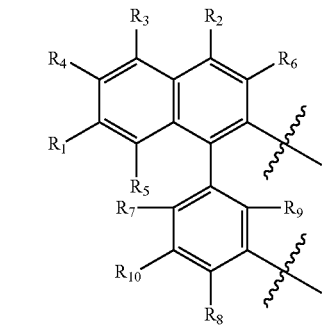

-continued
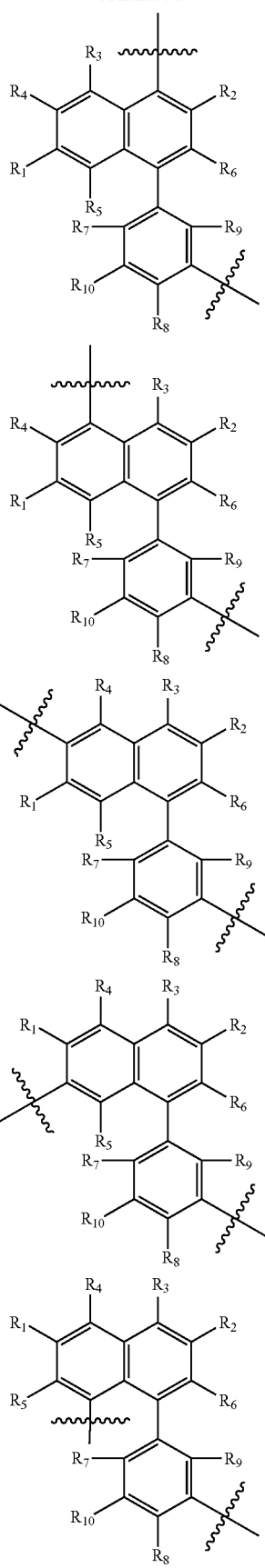
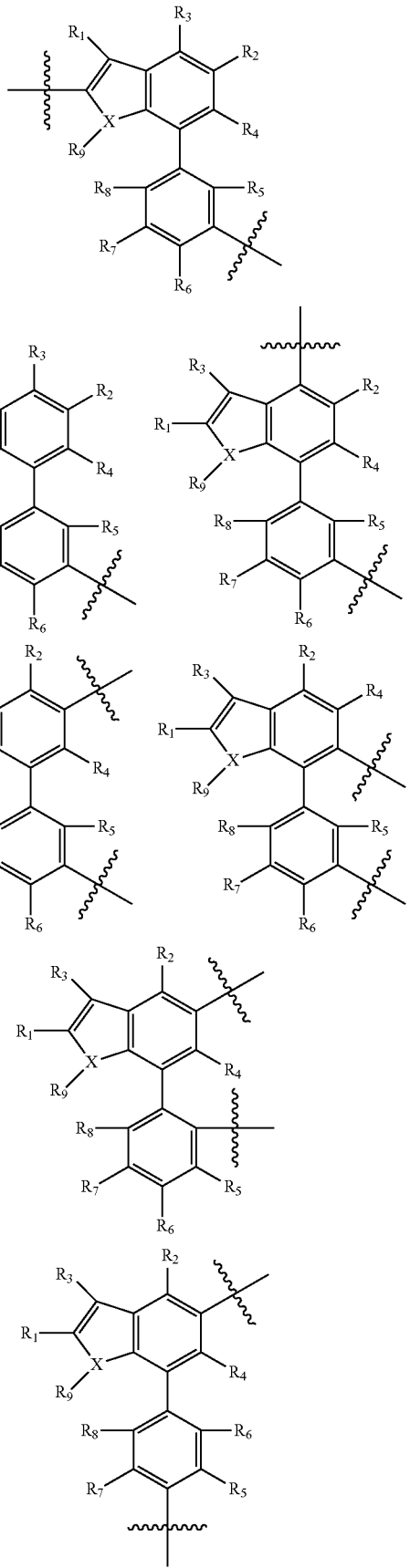

-continued
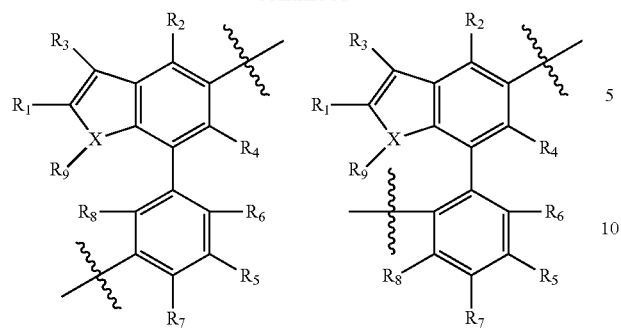
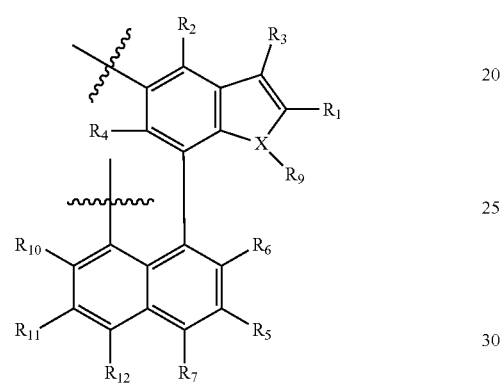
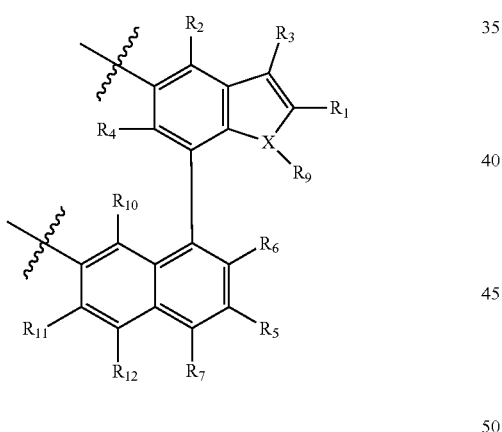
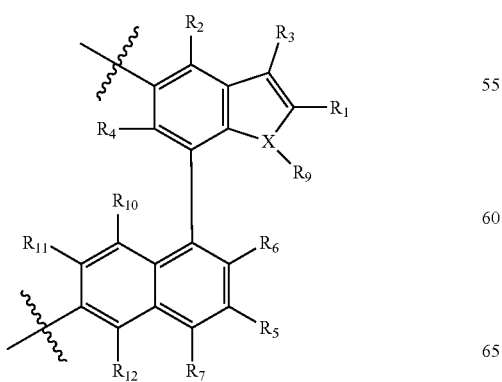
-continued
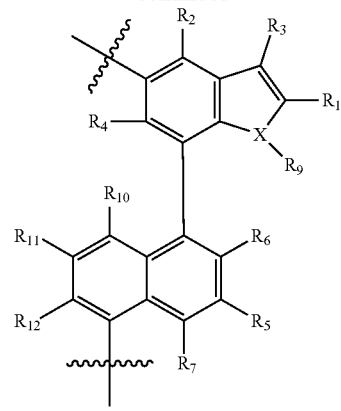
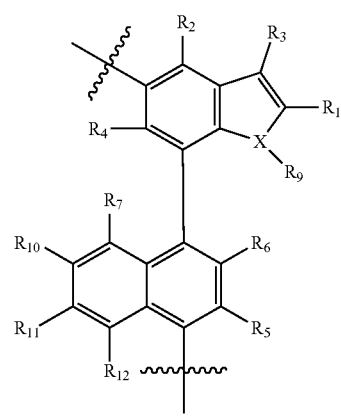
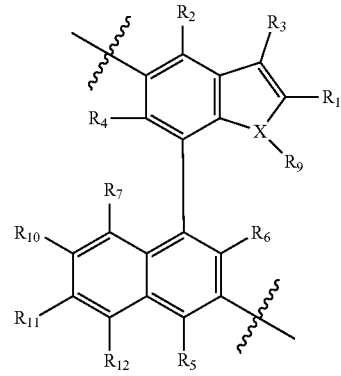
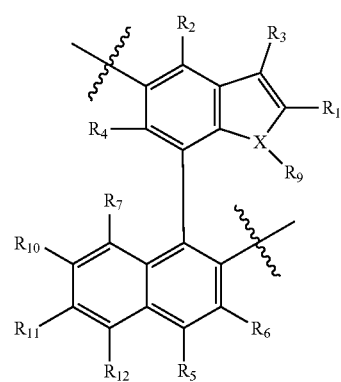

-continued

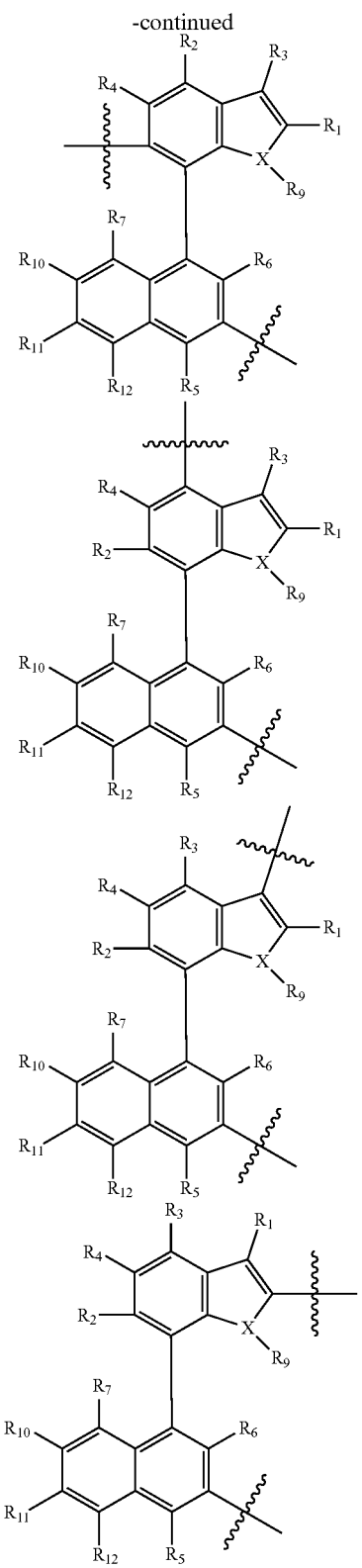

wherein X is S, Se, N, or O; each of $R_1$-$R_{12}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$ cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl; and each of the wavy lines represents one of the meta positions, and wherein each of the one or more Ars comprises one of a thiophene-based unit, a furan-based unit, a selenophene-based unit, or a pyrrole-based unit respectively with a formula of:

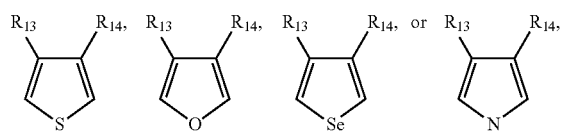

or a combination thereof, wherein each of $R_{13}$ and $R_{14}$ is independently selected from one of hydrogen, $C_1$-$C_{30}$alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

10. The electrochromic polymer of claim 9, wherein the one or more MCLs and the one or more Ars are arranged in an alternative fashion with a formula of

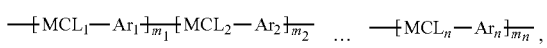

wherein each of n and $m_1, m_2, \ldots, m_n$ is an integer greater than 0.

11. The electrochromic polymer of claim 9, wherein the thiophene-based unit comprises a formula of

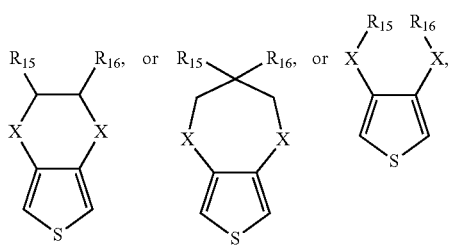

-continued

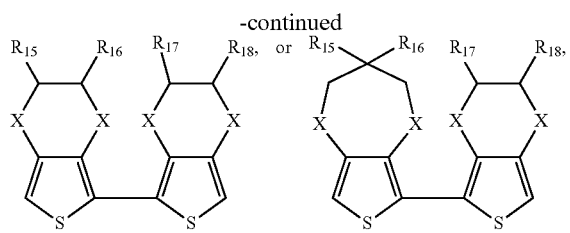

or

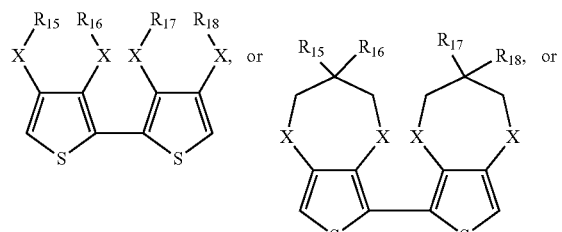

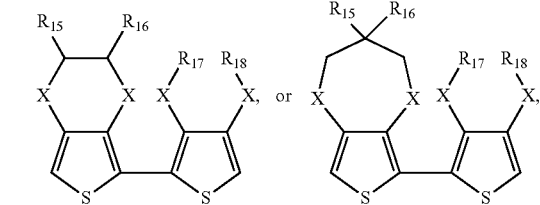

or a combination thereof,
wherein X is S, Se, N, or O; each of $R_{15}$-$R_{18}$ is independently selected from one of hydrogen, $C_1$-$C_{30}$ alkyl, $C_2$-$C_{30}$ alkenyl, $C_2$-$C_{30}$ alkynyl, $C_2$-$C_{30}$ alkylcarbonyl, $C_1$-$C_{30}$ alkoxy, $C_3$-$C_{30}$ alkoxyalkyl, $C_2$-$C_{30}$ alkoxycarbonyl, $C_4$-$C_{30}$ alkoxycarbonylalkyl, $C_1$-$C_{30}$ alkylthio, $C_1$-$C_{30}$ aminylcarbonyl, $C_4$-$C_{30}$ aminylalkyl, $C_1$-$C_{30}$ alkylaminyl, $C_1$-$C_{30}$ alkylsulfonyl, $C_3$-$C_{30}$ alkylsulfonylalkyl, $C_6$-$C_{18}$ aryl, $C_3$-$C_{15}$ cycloalkyl, $C_3$-$C_{30}$ cycloalkylaminyl, $C_5$-$C_{30}$cycloalkylalkylaminyl, $C_5$-$C_{30}$ cycloalkylalkyl, $C_5$-$C_{30}$ cycloalkylalkyloxy, $C_1$-$C_{12}$ heterocyclyl, $C_1$-$C_{12}$ heterocyclyloxy, $C_3$-$C_{30}$ heterocyclylalkyloxy, $C_1$-$C_{30}$ heterocyclylalkyloxy, $C_1$-$C_{30}$ heterocyclylaminyl, $C_5$-$C_{30}$ heterocyclylalkylaminyl, $C_2$-$C_{12}$ heterocyclylcarbonyl, $C_3$-$C_{30}$ heterocyclylalkyl, $C_1$-$C_{13}$ heteroaryl, or $C_3$-$C_{30}$ heteroarylalkyl.

12. The electrochromic polymer of claim 11, wherein X in the thiophene-based unit is O.

13. The electrochromic polymer of claim 9, wherein the electrochromic polymer comprises a formula of

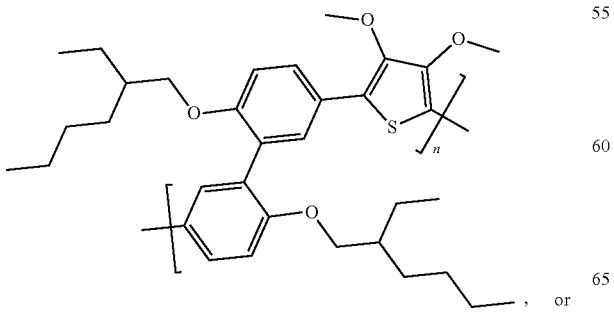

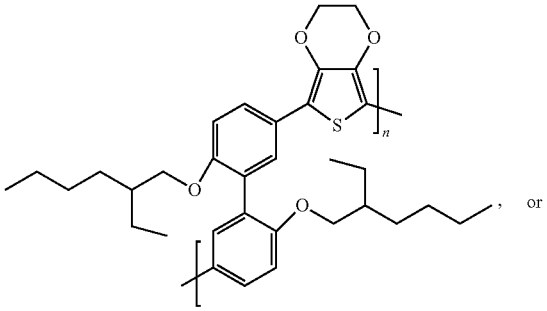

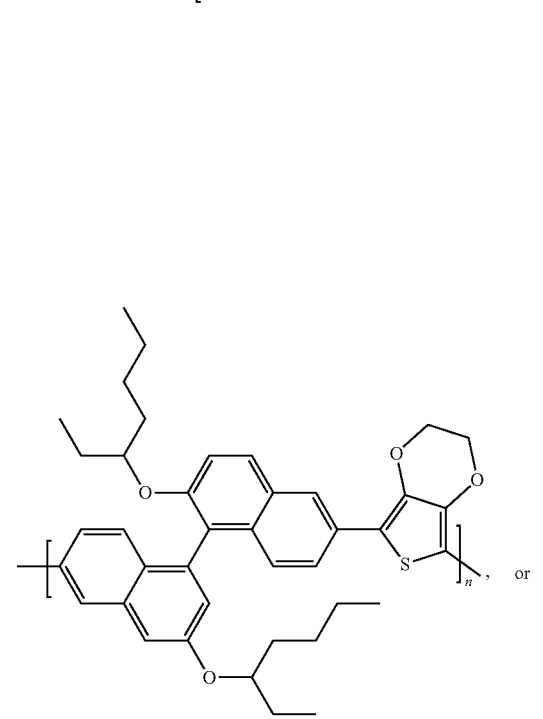

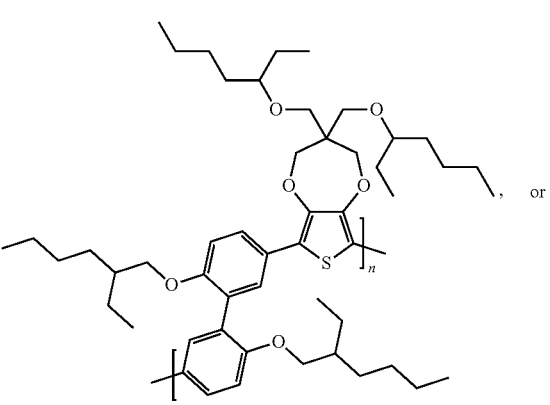

93
-continued
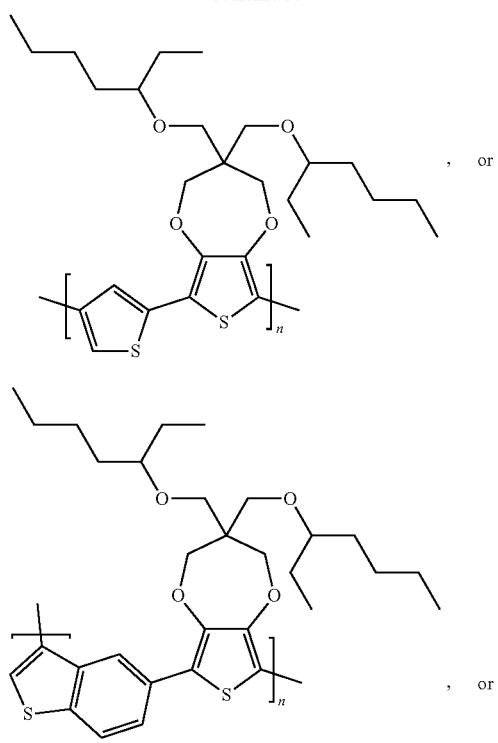
, or
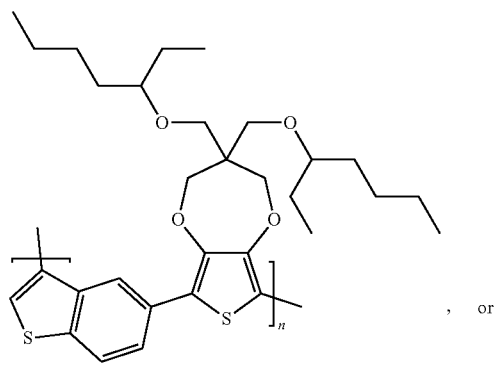
, or
94
-continued
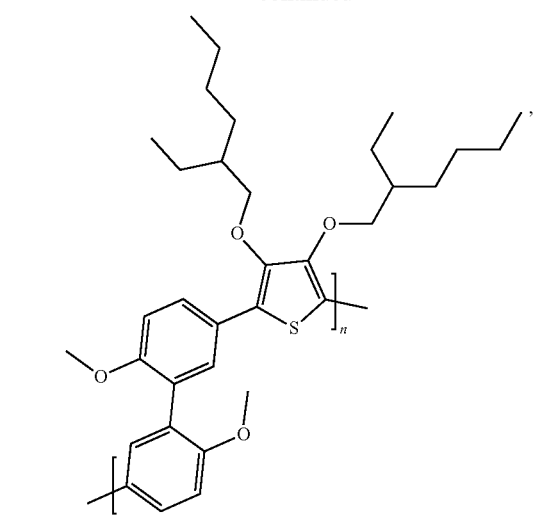
,
wherein n and m are integers greater than 0.
* * * * *